(12) United States Patent
Wiederin et al.

(10) Patent No.: US 10,545,160 B2
(45) Date of Patent: Jan. 28, 2020

(54) AUTOSAMPLER SAMPLE AND SAMPLE RACK IDENTIFICATION

(71) Applicant: Elemental Scientific, Inc., Omaha, NE (US)

(72) Inventors: Daniel R. Wiederin, Omaha, NE (US); Kevin Hahn, Omaha, NE (US); Connor Doolan, Omaha, NE (US); Karl Hauke, Queensland (AU); Guangwei Ji, Omaha, NE (US); Tyler Yost, Omaha, NE (US)

(73) Assignee: ELEMENTAL SCIENTIFIC, INC., Omaha, NE (US)

( * ) Notice: Subject to any disclaimer, the term of this patent is extended or adjusted under 35 U.S.C. 154(b) by 143 days.

(21) Appl. No.: 15/229,767

(22) Filed: Aug. 5, 2016

(65) Prior Publication Data
US 2017/0038402 A1   Feb. 9, 2017

Related U.S. Application Data

(60) Provisional application No. 62/201,722, filed on Aug. 6, 2015, provisional application No. 62/201,725, filed on Aug. 6, 2015.

(51) Int. Cl.
*G01N 35/00* (2006.01)

(52) U.S. Cl.
CPC .......... *G01N 35/00732* (2013.01); *G01N 2035/0091* (2013.01)

(58) Field of Classification Search
None
See application file for complete search history.

(56) References Cited

U.S. PATENT DOCUMENTS

| 4,810,096 A * | 3/1989 | Russell ............... G01N 21/253 356/400 |
|---|---|---|
| 5,663,545 A | 9/1997 | Marquiss |
| 2004/0014228 A1 | 1/2004 | Brignac, Jr. et al. |

(Continued)

FOREIGN PATENT DOCUMENTS

WO   9930824 A1   6/1999

OTHER PUBLICATIONS

International Preliminary Report on Patentability dated Feb. 6, 2018 for PCT/US2016/045826.

(Continued)

*Primary Examiner* — Xiaoyun R Xu
(74) *Attorney, Agent, or Firm* — Kevin E. West; Advent, LLP

(57) ABSTRACT

A sample identification system for an automated sampling device is described. A system embodiment includes, but is not limited to, a sample holder having a plurality of apertures configured to receive a plurality of sample vessels therein, the sample holder having one or more corresponding sample holder identifiers positioned proximate to the sample holder; and an identifier capture device configured to detect the one or more sample holder identifiers positioned proximate to the sample holder and generate a data signal in response thereto, the data signal corresponding to at least an orientation of the sample holder relative to a surface on which the sample holder is positioned.

14 Claims, 43 Drawing Sheets

(56) References Cited

U.S. PATENT DOCUMENTS

| | | | |
|---|---|---|---|
| 2004/0253148 A1* | 12/2004 | Leaton | B01L 3/02 |
| | | | 422/400 |
| 2006/0051239 A1 | 3/2006 | Massaro | |
| 2008/0241939 A1 | 10/2008 | Matsuo et al. | |
| 2009/0134069 A1* | 5/2009 | Handique | B01L 7/52 |
| | | | 209/11 |
| 2016/0025757 A1* | 1/2016 | Pollack | G01N 21/253 |
| | | | 348/143 |

OTHER PUBLICATIONS

International Search Report and Written Opinion dated Dec. 1, 2016 for PCT/US2016/045826.

\* cited by examiner

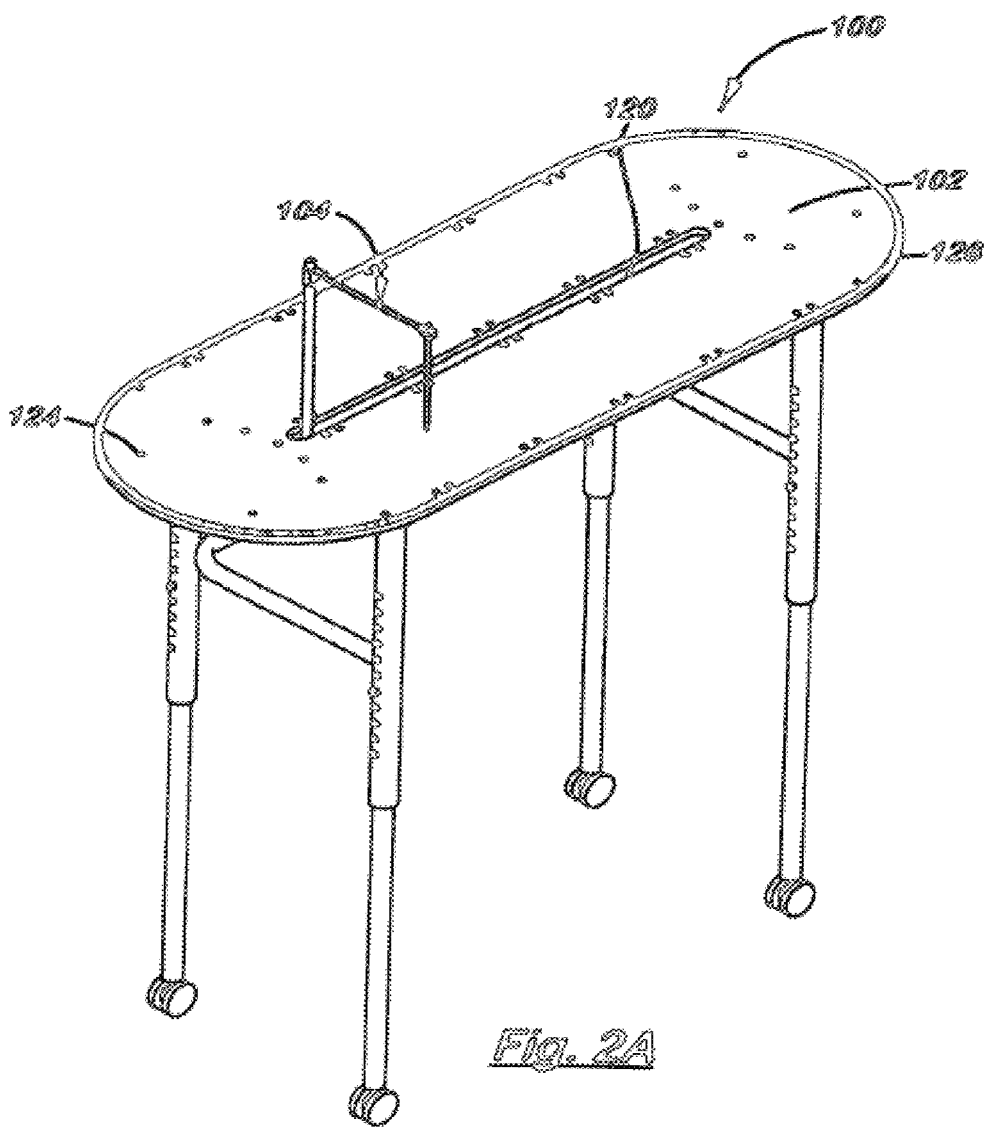

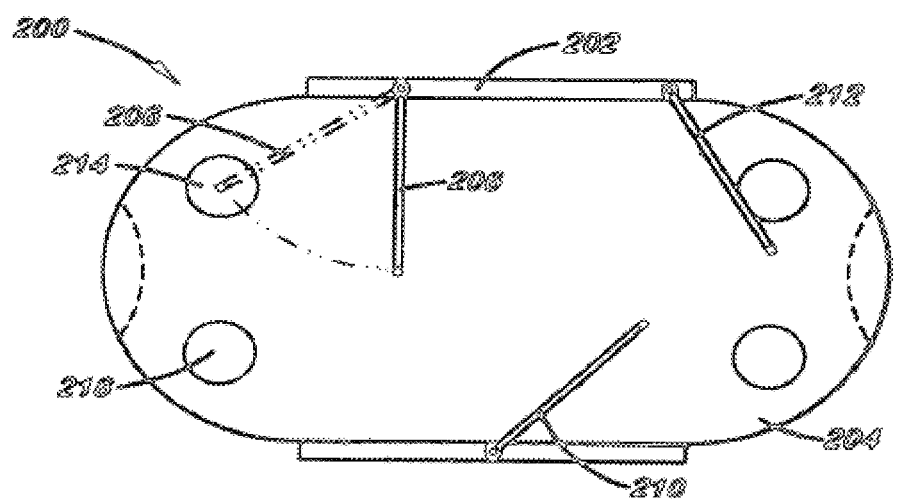

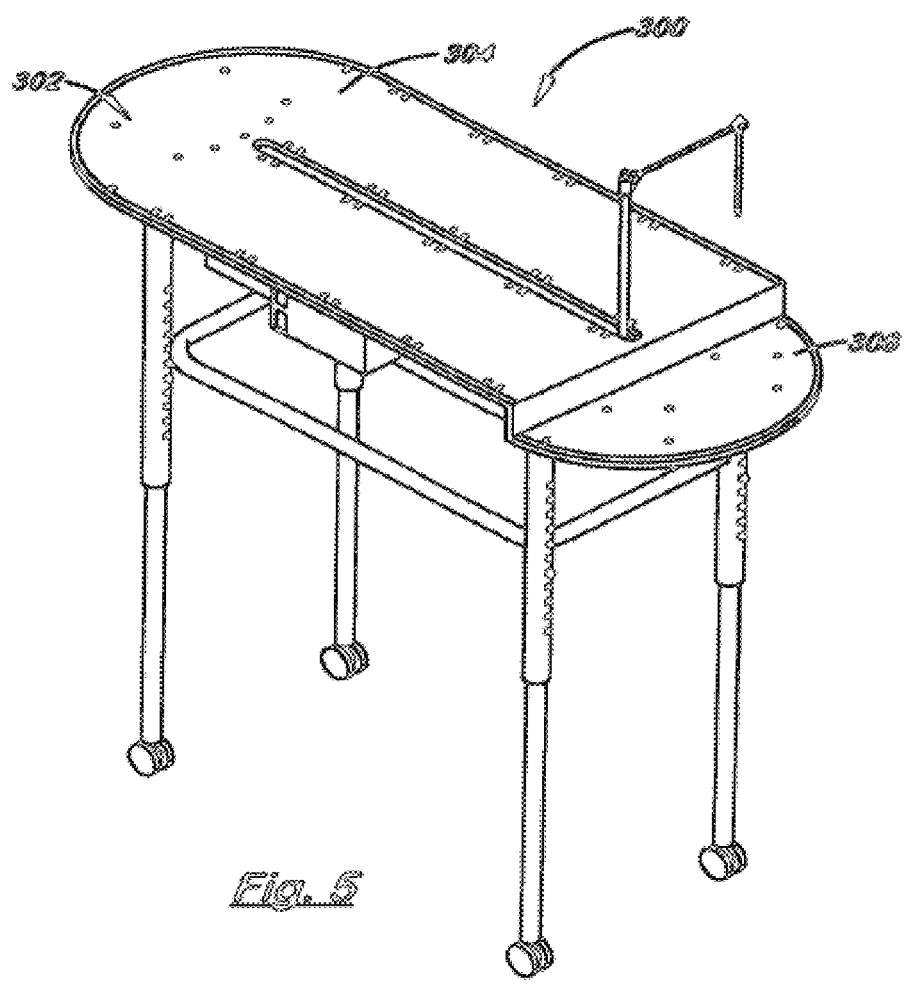

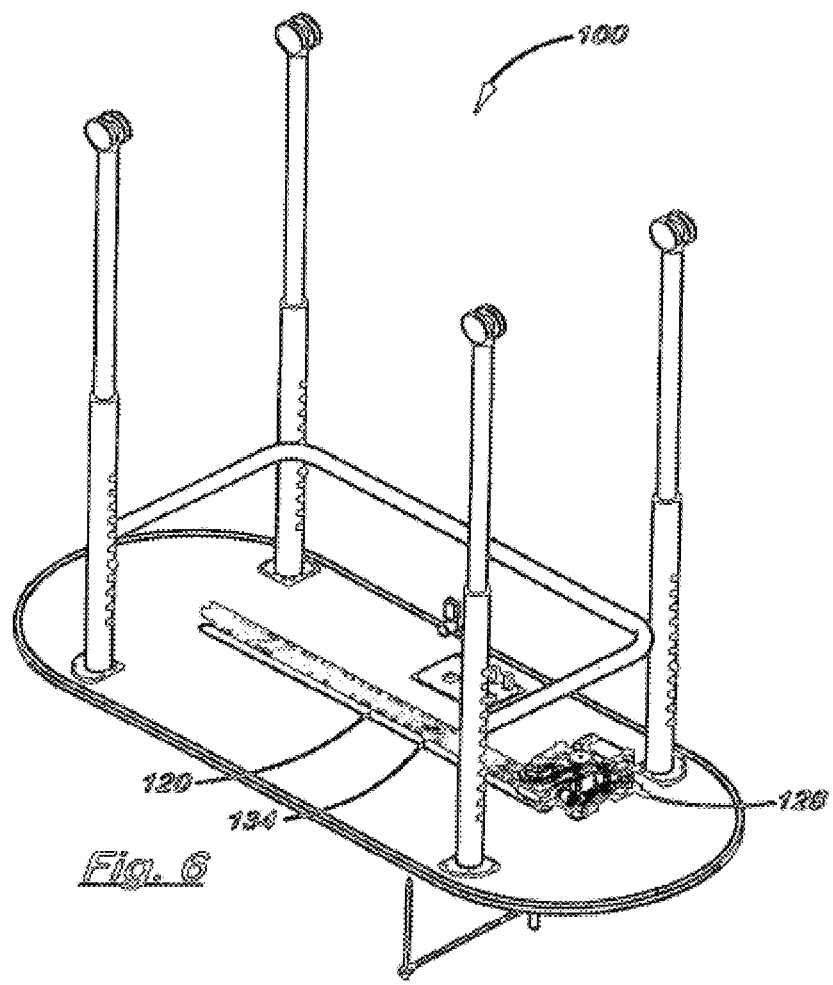

Standards

| Name | Rack | Vial | Matrix | Expiry Date | Serial Number | Elements/concentration | Units |
|---|---|---|---|---|---|---|---|
| Internal Standard 7 for EPA Method 200.8 | 0 | 1 | 2% HNO3 | 4/6/2016 | 31104061 | Bi, Ge, In, 6Li, Sc, Tb, Y | ug/mL |
| ICP-200.7-1 Solution A | 0 | 2 | 2% HNO3 | 8/15/2015 | 29908151 | Al: 1000, Ca: 1000, Cr: 500, Mg: 1000, Ni: 500, K: 1000, Na: 1000, Zn: 500 | ug/mL |
| ICP-200.7-2 | 0 | 3 | 2% HNO3 | Expired on 4/5/2015 — 1040 | 30104051 | Ba: 100, Be: 100, Co: 200, Cu: 100, Fe: 1000, Mn: 100, Sr: 1000, V: 100 | ug/mL |

AUTOSAMPLER SAMPLE AND SAMPLE RACK IDENTIFICATION

CROSS-REFERENCE TO RELATED APPLICATIONS

The present application claims the benefit under 35 U.S.C. § 119(e) of U.S. Provisional Application Ser. No. 62/201,725, filed Aug. 6, 2015, and titled "AUTOSAMPLER SAMPLE RACK IDENTIFICATION," and of U.S. Provisional Application Ser. No. 62/201,722, filed Aug. 6, 2015, and titled "AUTOMATIC DETECTION OF EXPIRED STANDARD SOLUTIONS," each of which is herein incorporated by reference in its entirety.

BACKGROUND

In many laboratory settings, it is often necessary to analyze a large number of chemical or biochemical samples at one time. In order to stream-line such processes, the manipulation of samples has been mechanized. Such mechanized sampling is commonly referred to as autosampling and is performed using an automated sampling device or autosampler.

SUMMARY

A sample identification system for an automated sampling device is described. A system embodiment includes, but is not limited to, a sample holder having a plurality of apertures configured to receive a plurality of sample vessels therein, the sample holder having one or more corresponding sample holder identifiers positioned proximate to the sample holder; and an identifier capture device configured to detect the one or more sample holder identifiers positioned proximate to the sample holder and generate a data signal in response thereto, the data signal corresponding to at least an orientation of the sample holder relative to a surface on which the sample holder is positioned.

A method embodiment includes, but is not limited to, detecting a sample holder identifier positioned on a sample holder, the sample holder having a plurality of apertures configured to receive a plurality of sample vessels therein; and determining an orientation of the sample holder based upon the sample holder identifier detected, the orientation of the sample holder being relative to a surface on which the sample holder is positioned.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

FIGURES

The Detailed Description is described with reference to the accompanying figures. The use of the same reference numbers in different instances in the description and the figures may indicate similar or identical items.

FIG. 2A is a partial isometric view illustrating an automated sampling or dispensing device in accordance with example implementations of the present disclosure, where a center slot in the support surface is present allowing the sample arm assembly to be connected with the drive assembly.

FIG. 4B is a plan view illustrating an automated sampling or dispensing device in accordance with example implementations of the present disclosure, where multiple sample arm assemblies and rinse stations are present on one support surface.

FIG. 5 is an isometric view illustrating an automated sampling or dispensing device in accordance with example implementations of the present disclosure, where the support surface of the automatic sampling or dispensing device is provided with more than one plane.

FIG. 6 is an isometric view of the automated sampling or dispensing device shown in FIG. 1, further illustrating the drive assembly.

DETAILED DESCRIPTION

Overview

Often in laboratory settings, large numbers of samples are analyzed. Autosamplers are frequently used to test the composition of these samples. Using an autosampler allows more samples to be prepared and tested. During the sample preparation process, multiple samples may be prepared and placed in individual sample vessels at one time or over a period of time, which can lead to errors associated with sample identification. For example, laboratory personnel can place samples prepared for testing in sample vessels without labeling the vessels or identifying the sample vessels in some manner. This lack of labeling or identification may lead to errors (e.g., misplacement of samples, misidentification of samples, etc.) when arranging the samples for testing via autosampler or when entering the sample information into a computer system connected to an autosampler. For example, the sample rack itself could be placed in an orientation relative to the autosampler that would result in skewed data analysis even if the sample vessels were properly arranged within the sample rack.

Accordingly, a sample identification system for an automated sampling device is disclosed that includes a sample holder having one or more corresponding sample holder identifiers positioned proximate to the sample holder. The system also includes an identifier capture device configured to detect the one or more sample holder identifiers positioned proximate to the sample holder and generate a data signal in response thereto, the data signal corresponding to at least an orientation of the sample holder.

Example Implementations

Figure 1:
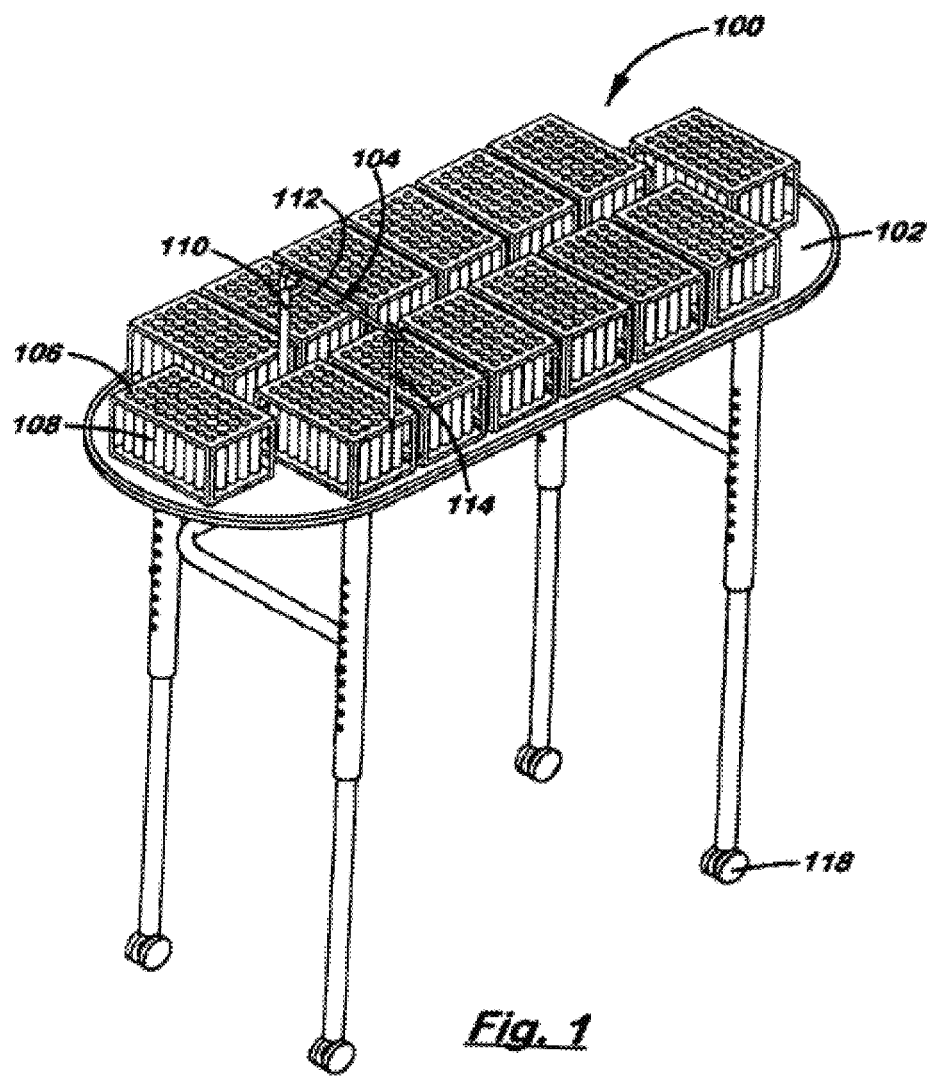
FIG. 1 is an isometric view illustrating an automated sampling or dispensing device in accordance with example implementations of the present disclosure.

FIG. 1 illustrates automated sampling device 100 in accordance with an example implementation of the present disclosure. Automated sampling device 100 includes table top 102 and sample arm assembly 104. Further, sample holders 106 holding multiple sample vessels 108 are present on table top 102 in preparation for sample assaying. It should be understood that automated sampling device 100 may assay from one to many hundreds of samples (e.g., greater than 1200 samples in the example implementation illustrated) in a given time depending upon test requirements. Verification of a sample identify of a sample to be analyzed is described with reference to FIGS. 20 through 29B.

In the implementation illustrated, sample arm assembly 104 includes a z-axis support 110 and a sample probe support arm 112 that supports a sample probe 114. As illustrated, the z-axis is aligned with gravity or a vertical axis. In use, sample probe 114 is mounted to sample probe support arm 112, which is moved through space in three dimensions, or about an axis having y-motion that is a substantially rotary motion and along an axis having x-motion which is at least substantially horizontal linear motion or translation, and along a z-axis that is at least substantially vertical, for linear motion or translation. In an implementation, the length of a sample probe support arm (the length of an arm extending from the y-rotary axis) is no more than one-half the length of a linear translation of the center slot (i.e., is no more than half of the length of x-axis linear motion). In an implementation, the length of the sample probe support arm is approximately equal to one-half the length of a linear translation of the center slot. Such configuration allows nearly one hundred percent of the footprint of the table to be accessed by the sample probe. Footprint is defined as being substantially equivalent to an area encompassed by the area of the table top. In an additional implementation, the y-rotary axis of an automated sampling device allows for access to sample vessels on either side of the x-axis motion of linear travel (i.e., on either side of the center slot).

In an implementation, the components of sample arm assembly 104 are formed of carbon composite materials. Further, all exposed surfaces of the sample arm assembly 104 are made from inert or fluoropolymer-covered materials (i.e., Teflon®). It should be understood, however, that the sample arm assembly may be made with various materials, including aluminum, steel, plastic, and so forth.

In addition, sample arm assembly 104 is designed to attach to various surface supports including a table top. Such assembly may be attached to either side of the center slot. In an implementation, table top 102 may be mounted onto legs with casters 118, rollers and so forth. Such configuration increases the mobility of the automated sampling device, thereby facilitating preparation of samples at a location separate from the analytical instruments. Further, this configuration provides storage room underneath the table top which may be absent with bench-top automated sampling devices. The height of the table is adjustable to compensate for the effects of gravity on liquid flow rates when self-aspirating sampling devices are used. The ability to adjust table top height also allows the automated sampling device to accommodate various sized sample vessels.

Figure 2B:
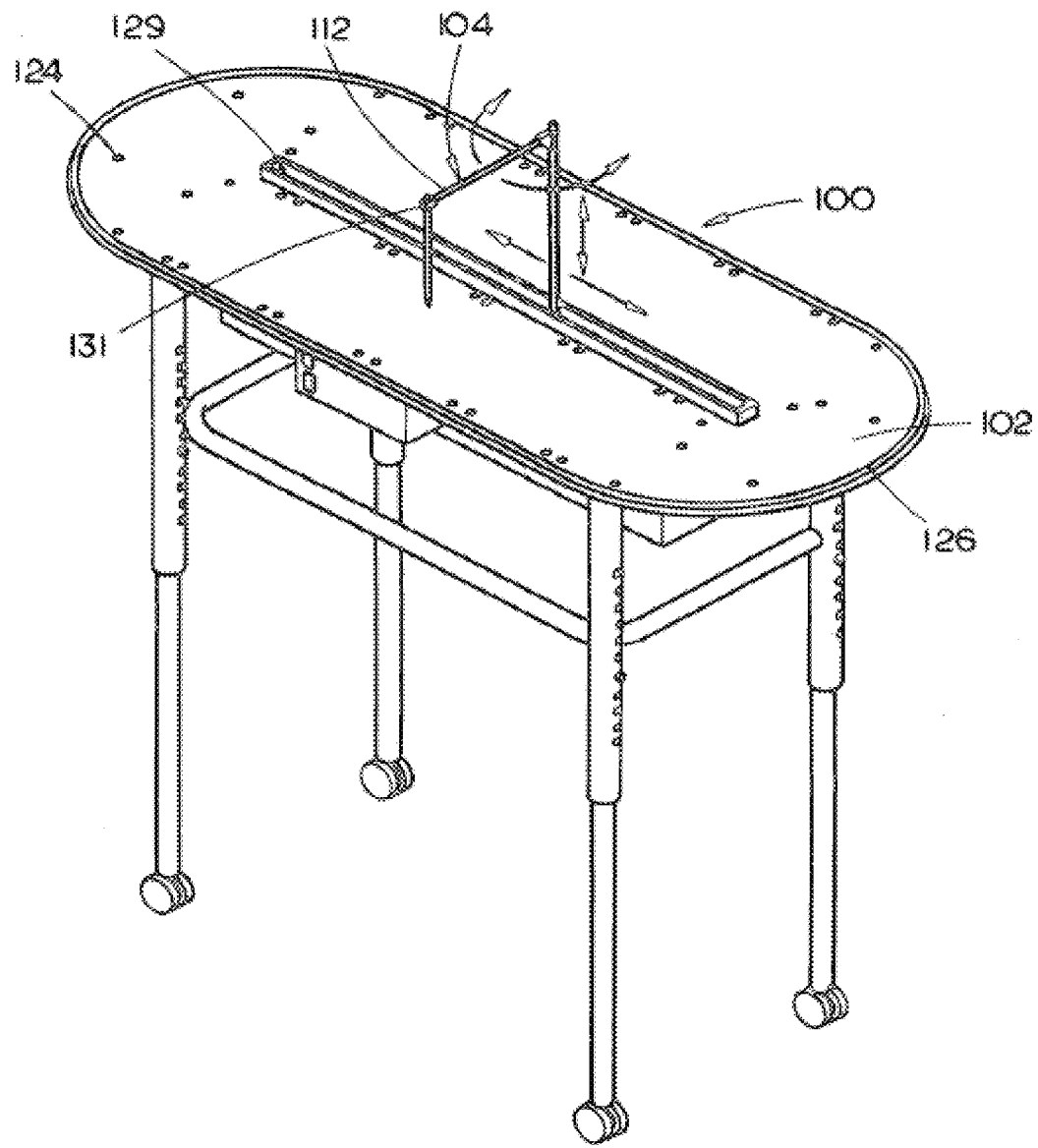
FIG. 2B is a partial isometric view illustrating an automated sampling or dispensing device in accordance with example implementations of the present disclosure, where a raised slot on the support surface is present to attach the sample arm assembly to the drive assembly.

FIGS. 2A and 2B are additional illustrations of automated sampling or dispensing devices in which the sample arm assembly is attached to the drive assembly via a center slot or a raised slot, respectively. In FIG. 2A, automated sampling device 100 is comprised of sample arm assembly 104 extending through center slot 120 and table top 102 including a plurality of recesses 124 and the channel 126. The sample arm assembly 104 is attached to the drive assembly (not shown) via center slot 120. In an implementation, the plurality of recesses is coupled with sensors for detecting the location of sample holders. The sample holder location information may then be transferred to a controller of a drive assembly controlling the sample arm assembly providing the alignment system. The previous configuration allows the sample arm assembly to detect the location of sample vessels on the table top at a given time. Channel 126 runs along the edge of table top 102 to collect possible sample spillage.

In addition to FIG. 2A, FIG. 2B demonstrates an automated sampling or dispensing device including a sample arm assembly 104 attached to the drive assembly 128 via a raised slot 129. In one implementation, a magnet 131 is attached to the end of the sample probe support arm 112 which allows detection of a three-dimensional position in space where the magnet 131 is embedded into the sample probe support arm 112 and is detected by a sensing means such as a Hall Effect sensor.

Figure 3:
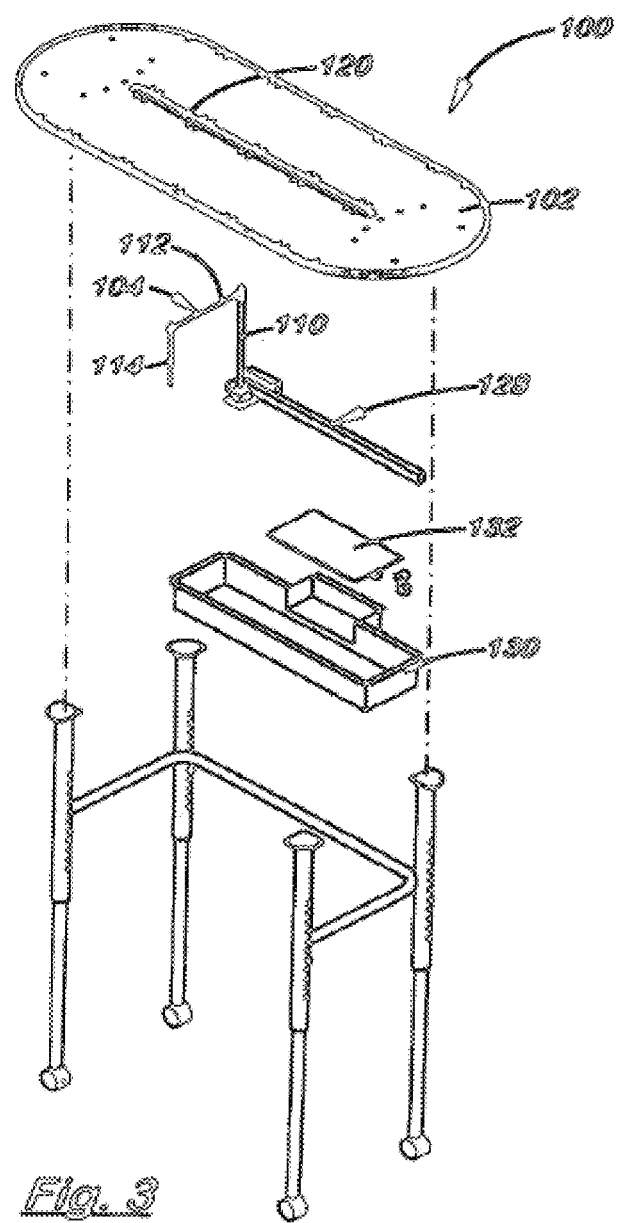
FIG. 3 is an exploded view of the automated sampling or dispensing device shown in FIG. 1, further illustrating components of the device.

Referring now to FIG. 3, an exploded view of the components comprising the automated sampling device 100 is provided. The automated sampling device 100 is comprised of a table top 102 with center slot 120, drive assembly 128, sample arm assembly 104, housing 130, and controller 132. Sample arm assembly 104 includes z-axis support 110 attached to drive assembly 128, sample probe support arm 112 attached to z-axis support 110, and sample probe 114 attached to sample probe support arm 112. Sample arm assembly 104 is controlled by drive assembly 128 and controller 132. In an implementation, drive assembly 128 causes sample arm assembly 104 to move along center slot 120, in translation along an axis coaxial to z-axis support 110, and radially about the z-axis for inserting sample probe 114 into a sample vessel. Further, sample arm assembly 104 is no more than one-half the length of a linear translation of the length of center slot 120. As previously mentioned, such configuration allows nearly one hundred percent of the footprint to be accessed by sample probe 114. In addition, automated sampling device 100 is capable of assaying hundreds of samples at a given time without operator assistance, thereby allowing the operator to perform other tasks. Moreover, it is possible to configure the automated sampling device to assay samples overnight, allowing work productivity to be increased.

To accommodate gross differences in sample vessel height, sample probe support arm 112 may be moved up or down z-axis support 110 as desired prior to sample assaying. Once the desired position is reached, sample probe support arm 112 is secured into a fixed position on z-axis support 110 and sample vessels containing samples may be loaded onto the table top. This feature allows the automated sampling device to be used on various sizes of sample vessels while still not having mechanical moving parts above stationary samples. Additionally, housing 130 encloses drive assembly 128 to protect the assembly from debris, dust, contaminates, and so forth. Housing 130 may be made of various materials, e.g., blow molded polyethylene, and so forth.

Figure 4A:
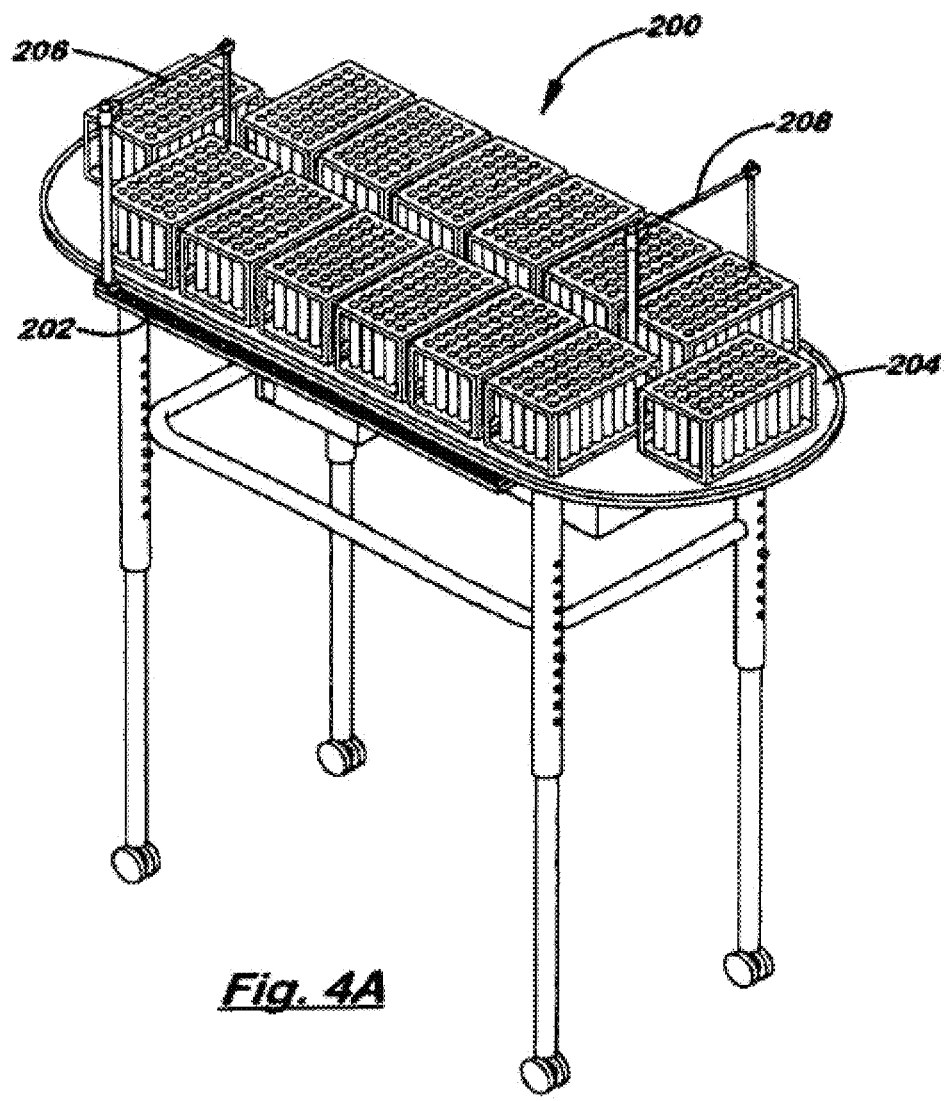
FIG. 4A is an isometric view illustrating an automated sampling or dispensing device in accordance with example implementations of the present disclosure where multiple sampling arm assemblies and drive assemblies are mounted to the top of the support surface of the automated sampling or dispensing device.

FIGS. 4A and 4B illustrate an automated sampling device 200 in accordance with another example implementation of the present disclosure, where multiple sampling arm assemblies (i.e., sample arm assembly 206, 208, and 210) are mounted to the table top of the automated sampling device. Automated sampling device 200 includes multiple automated sampling devices attached to a table top at one time. A rail 202 is attached to the edge of table top 204 to enable the attachment of additional sample arm assemblies (i.e., sample arm assembly 206 and 212). Utilization of additional sample arm assemblies allows multiple sample zones to be configured (i.e., a prep zone, an assaying zone, and so forth).

In additional implementations, various types of multiple rinse or eluent stations may be included in the automated sampling device. For instance, multiple rinse stations (i.e., 214 and 216) of the overflow type designed to reduce the chance of carry-over contamination may be present. Further, overflow rinse stations may contain a series of different chemical rinses to reduce contamination between sample analyses (e.g., surfactant, nitric acid, hydrofluoric acid, and/or deionized water). For multiple eluent stations, the automated sampling device may contain such stations for step elution from a chromatographic column.

Referring now to FIG. 5, an automated sampling device in accordance with another example implementation of the present disclosure is described, where a table top having more than one plane is provided. Automated sampling device 300 includes table top 302 which has more than one plane, plane one 304 and plane two 306. Such configuration allows table top 302 to accommodate various sizes of vessels. For instance, the height of vessels in plane two 306 may be taller than vessels in plane one 304 of table top 302.

Figure 7:
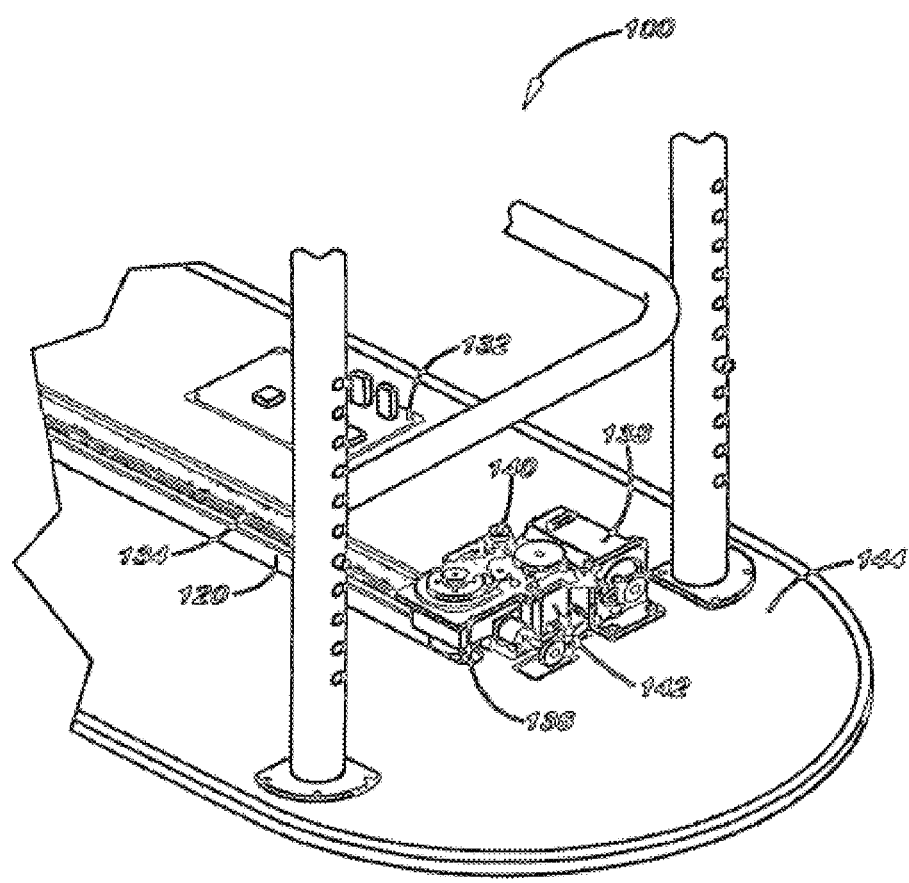
FIG. 7 is a partial isometric view of the drive assembly shown in FIG. 6, further illustrating components of the drive assembly.

FIGS. 6 and 7 further illustrate a drive assembly of automated sampling device 100 attached to a table top bottom. FIG. 6 provides an overview of a drive assembly in accordance with the present disclosure, depicting a linear drive 134 running parallel to center slot 120 and connected to sled 128. FIG. 7 is an enlarged view of the drive assembly illustrated in FIG. 6. Drive assembly 100 is comprised of motor one 138, motor two 140, motor three 142, sled 136, linear drive 134, and controller 132. Motor one 138 controls translation of a sample arm assembly's movements along the center slot 120 and is attached to table top bottom 144 and linear drive 134. Various stepper motors may be used to control translation of the sample arm assembly's movements along center slot 120. Moreover, it will be appreciated that various linear drives may be used including a worm drive. Motor two 140 controls angular rotation of a sample arm assembly and is connected to sled 136. In an implementation, motor two 140 is a radial motor. Motor three 142 controls vertical movement of a sample arm assembly and is attached to sled 136. Various stepper motors may be used for controlling vertical movement of the sample arm assembly. In an additional implementation, motor three 142 comprises a slip-clutch system. Further, in accordance with the present disclosure, the drive assembly may be hard-wired or, in another implementation, controlled via wireless communication. Thus, wireless communications may be used to connect controller 132 with the desired analytical instrument (not shown). Utilization of wireless communications allows sample assaying to occur without requiring physical connection with a controller computer increasing mobility of the automated sampling device.

Figure 8:
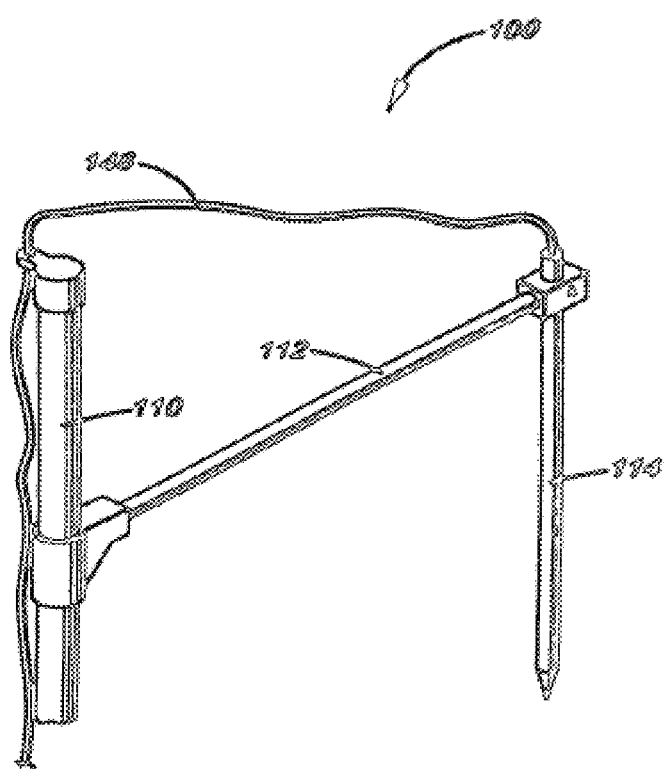
FIG. 8 is a partial isometric view illustrating a sample arm assembly for an automated sampling or dispensing device in accordance with example implementations of the present disclosure.

FIG. 8 provides a detailed depiction of a sample arm assembly of an automated sampling device in accordance with the first example implementation of the present disclosure. As previously described, the sample arm assembly includes z-axis support 110 attached to a drive assembly (see FIGS. 6 and 7), sample probe support arm 112 attached to z-axis support 110, and sample probe 114 attached to sample probe support arm 112. In an implementation, the sample arm assembly is attached to the drive assembly via the z-axis support extending through a center slot in the table top; in such implementation, the drive assembly is attached to a table top bottom. However, it should be understood that the drive assembly may be disposed in a variety of locations including on top of the table top without departing from the scope of the present disclosure.

In an additional implementation in accordance with the present disclosure, sample tubing 146 is present to allow sample removal or reagent delivery as desired. Further, a slip bearing is built into sample probe 114 to prevent winding of sample tubing 146. It is contemplated that the sample may be delivered to various types of scientific instrumentation (e.g., an inductively couple plasma system, a mass spectrometer, and so forth) or a number of other types of vessels (e.g., a waste collecting bucket following a wash step). It is further contemplated that the sample tubing may be flexible (as shown) or rigid, e.g., comprised of plastic, metal, and so forth. In another implementation, the automated sampling device may be equipped with one or more independent components for the purpose of sample preparation, sample dilution, addition of standards to samples or sample acidification.

Figure 9A:
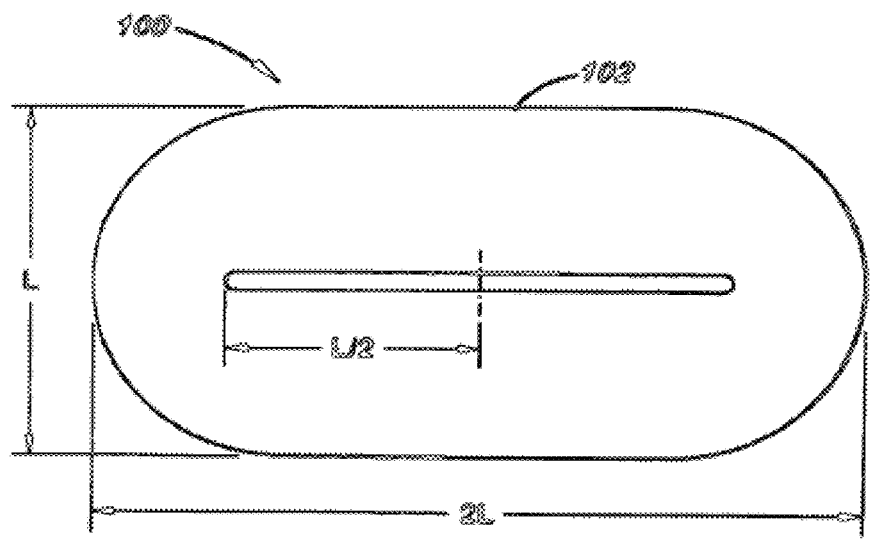
FIG. 9A is a plan view illustrating a support surface for use with an automated sampling or dispensing device, where the support surface includes a slot and has a footprint in accordance with example implementations of the present disclosure.
Figure 9B:
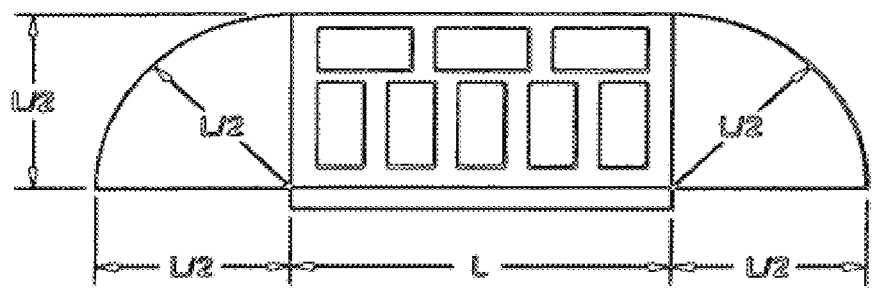
FIG. 9B is a plan view illustrating a support surface for use with an automated sampling or dispensing device, in accordance with example implementations of the present disclosure.

Referring to FIGS. 9A and 9B, tables for use with an automated sampling device are described in accordance with example implementations of the present disclosure. First, the table 102 includes a slot of length L providing for translation of the sample arm assembly along the length of the table. Further, the table 102 has a footprint for maximizing the usable area of the table 102. As illustrated in FIG. 9A, the table 102 has a width L substantially equal to the length of the slot L. Moreover, the table 102 is twice as long as the slot, having a length of 2 L. Further, the arm length of a sample probe assembly (as shown in FIGS. 1, 2, and 3) is half the length of the slot, having length L/2. This configuration allows for approximately one hundred percent of the footprint of the table to be accessed. In contrast, FIG. 9B illustrates an additional implementation in accordance with the present disclosure whereby the table is the shape of a semi-circle and a non-centered slot system is employed.

Figure 10:
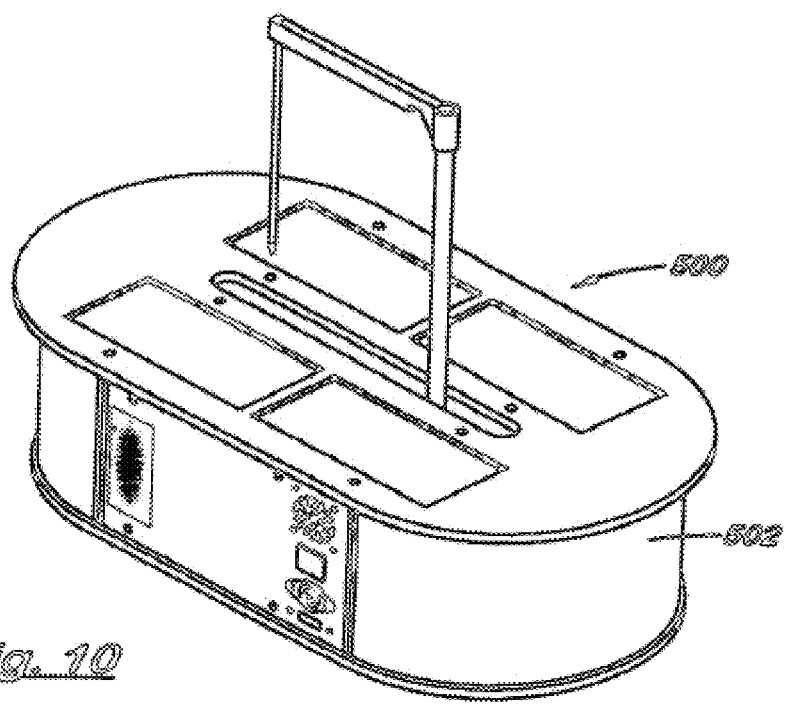
FIG. 10 is an isometric view illustrating an automated sampling or dispensing device in accordance with example implementations of the present disclosure, where the device includes a shroud.

Referring to FIG. 10, automated sampling or dispensing device 500 includes a shroud 502. In an example implementation, the shroud 502 substantially encloses the drive assembly 128 (FIG. 3) for protecting the drive assembly from dust and debris, and/or preventing dust and debris from the drive assembly from contaminating samples during assaying.

Figure 11:
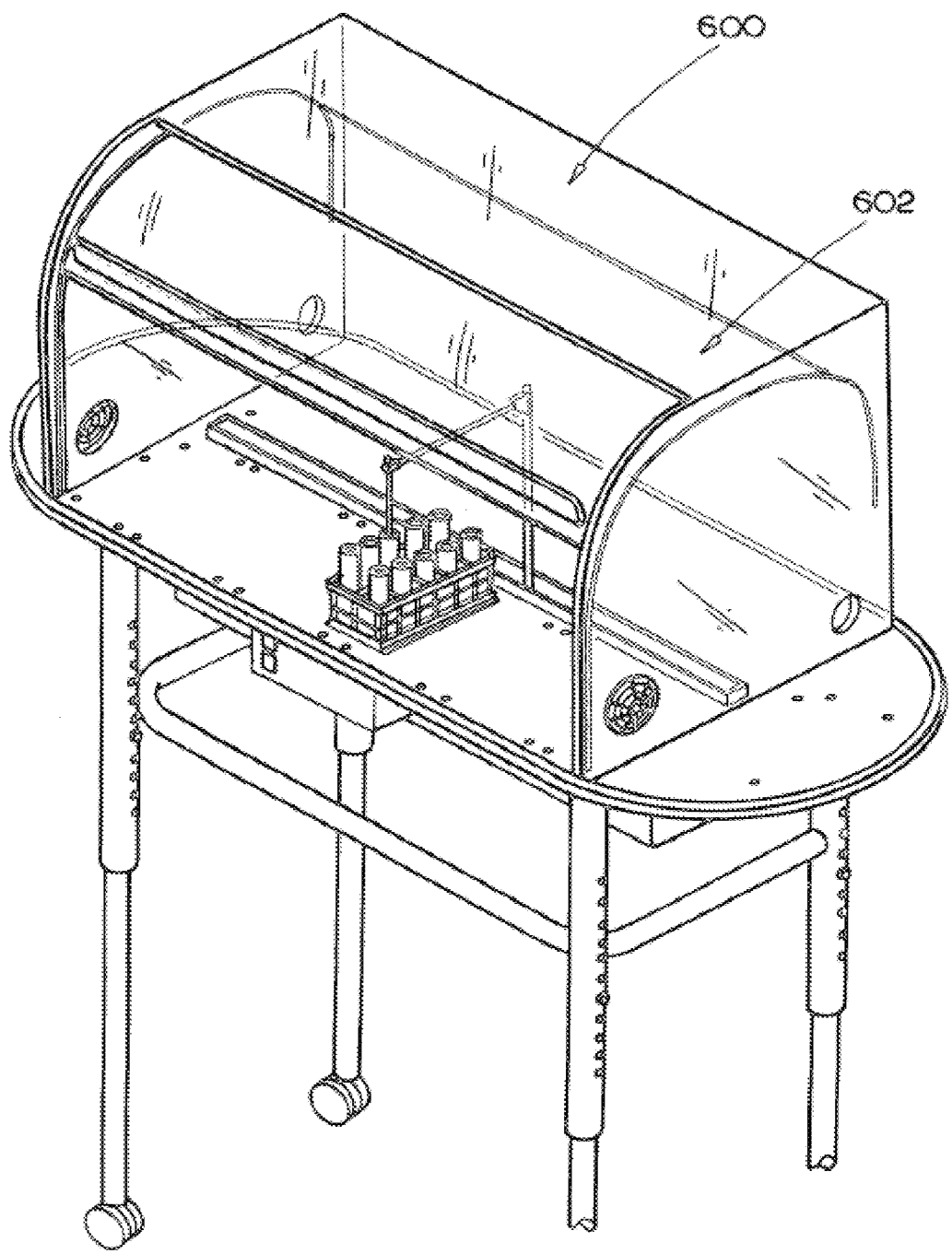
FIG. 11 is an isometric view illustrating an automated sampling or dispensing device in accordance with example implementations of the present disclosure, where the device is contained within a hood.

FIG. 11 illustrates automated sampling device 600 completely enclosed within a hood 602. Use of the hood allows the operations inside the hood to be isolated from the outside environment. The area within the hood may be ventilated to prevent the entry of contaminates such as bacteria or airborne substances. In one specific implementation, the air drawn into the enclosure is passed through a high efficiency particulate air (HEPA) filter. Further, processing of samples which contain hazardous chemicals within a hood allows such samples to be processed without further exposing the user to such chemicals during processing.

Referring generally to FIGS. 12 through 19, various implementations of an enclosure for an automated sampling/dispensing device are provided. In general, the enclosure includes at least one support member. The support member is generally perpendicular to a support surface on which the automated sampling/dispensing device is mounted. Further, a lid is mechanically coupled to the at least one support member for covering the support surface on which the automated sampling/dispensing device is mounted. Additionally, at least one flexible sheet is operationally coupled to at least one of the lid or the at least one support member. The at least one support member may provide support to both the lid as well as the at least one flexible sheet. The at least one support member, lid, and at least one flexible sheet enclose the automated sampling device while allowing access to the device by retracting the at least one flexible sheet.

The presently described example enclosures may minimize user exposure to the enclosed samples by allowing the containment of potentially hazardous chemicals within such enclosure. Further, the use of at least one flexible panel allows the enclosure to be shipped efficiently, as the enclosure may be disassembled into smaller pieces and thus be shipped in a smaller box when compared to enclosures with non-flexible panels/doors. Moreover, the use of the at least one flexible panel allows the enclosure to be shaped to accommodate varying shaped automated sampling and or dispensing devices and assemblies.

Figure 12:
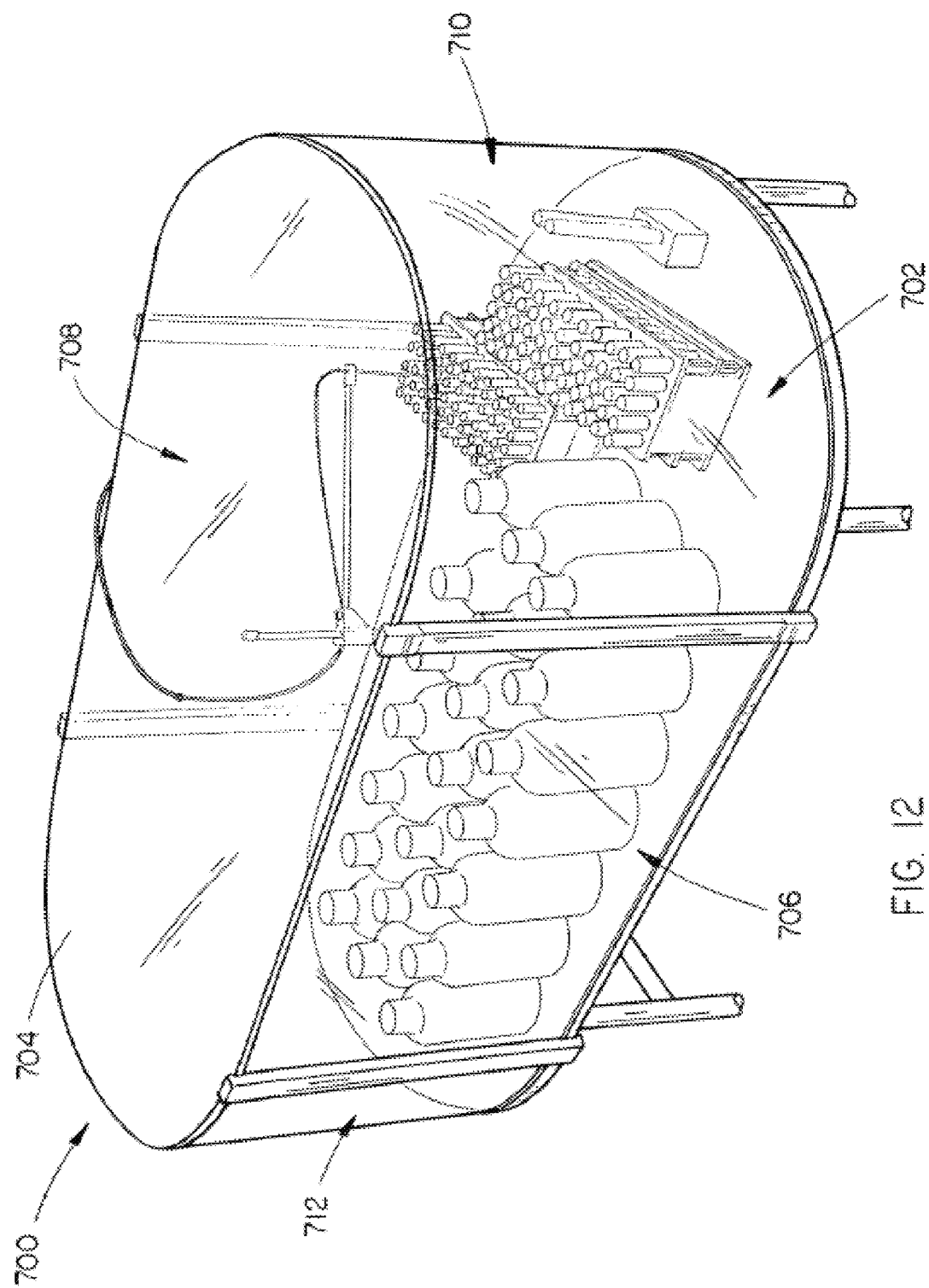
FIG. 12 is an isometric view illustrating an automated sampling or dispensing enclosure in accordance with example implementations of the present disclosure, where the enclosure includes two flexible sheets.

Referring to FIG. 12, an enclosure 700 for an automated sampling/dispensing device is provided in which the enclosure 700 surrounds an automated sampling/dispensing device mounted to a circular support surface 702. In an example implementation, the enclosure 700 includes a lid 704 for covering the support surface 702 on which the automated sampling/dispensing device is mounted. In such implementation, the lid 704 is generally equivalent in shape and size to that of the support surface 702 allowing the entire support surface 702 to be enclosed and available for use by a user. Further, an aperture for allowing the automated sampling/dispensing device to be connected with devices external to the enclosure may be defined within the lid. As illustrated in FIG. 12, an aperture defined within the lid 704 of the enclosure 700 allows a supply tube to the automated sampling/dispensing device to be connected with external laboratory analysis equipment. In another implementation, the enclosure 700 is designed to be airtight, allowing the enclosure 700 to contain potentially hazardous chemicals without requiring unnecessary exposure to laboratory personnel during sample preparation or analysis.

As illustrated in FIG. 12, the enclosure 700 includes a first support member 706 and a second support member 708. The first and second support members 706 and 708 are generally perpendicular to a support surface 702 on which the automated sampling/dispensing device is mounted. For example, as illustrated in FIG. 12, the first support member 706 and the second support member 708 are centered generally one hundred and eighty degrees (180°) opposite from one another. Moreover, such support members may be mechanically coupled to the lid 704 of the enclosure 700 as well as to the support surface 702. For instance, fasteners such as screws, bolts, nuts, and so forth may be used to fasten the support members to the lid and support surface. In an implementation, all fasteners are either metal-free or coated with an inert plastic coating to prevent interaction of such fasteners with chemical reagents or other substances being used with the automated sampling/dispensing device. In an additional implementation, an aperture may be formed within one or both of the support members to allow tubes, cords, and so forth to be connected to the automated sampling dispensing device contained within the enclosure as well as to external devices (e.g., laboratory analysis equipment), power sources, and so forth. It is contemplated that the lid 704 as well as the first support member 706 and the second support member 708 may be formed of inert, light-weight material including Plexiglas® (generically known as Lucite or polymethyl methacrylate.)

In additional implementations, as illustrated in FIG. 12, a first flexible sheet 710 and a second flexible sheet 712 are operationally coupled to at least one of the lid 708 or the first support member 706 or the second support member 708. In an implementation, the first flexible sheet 710 includes a first end and a second end. The first end of the first flexible sheet 710 includes a finished edge while the second end of the first flexible sheet 710 is fixedly coupled to the second support member 708. For example, the first end of the flexible sheet 710 is finished with a hardened-plastic cover which extends substantially along the length of the first end of the first flexible sheet 710. In addition, at least one guide member is attached to the first end of the first flexible sheet 710 to allow position of the first flexible sheet to be varied.

Figure 13:
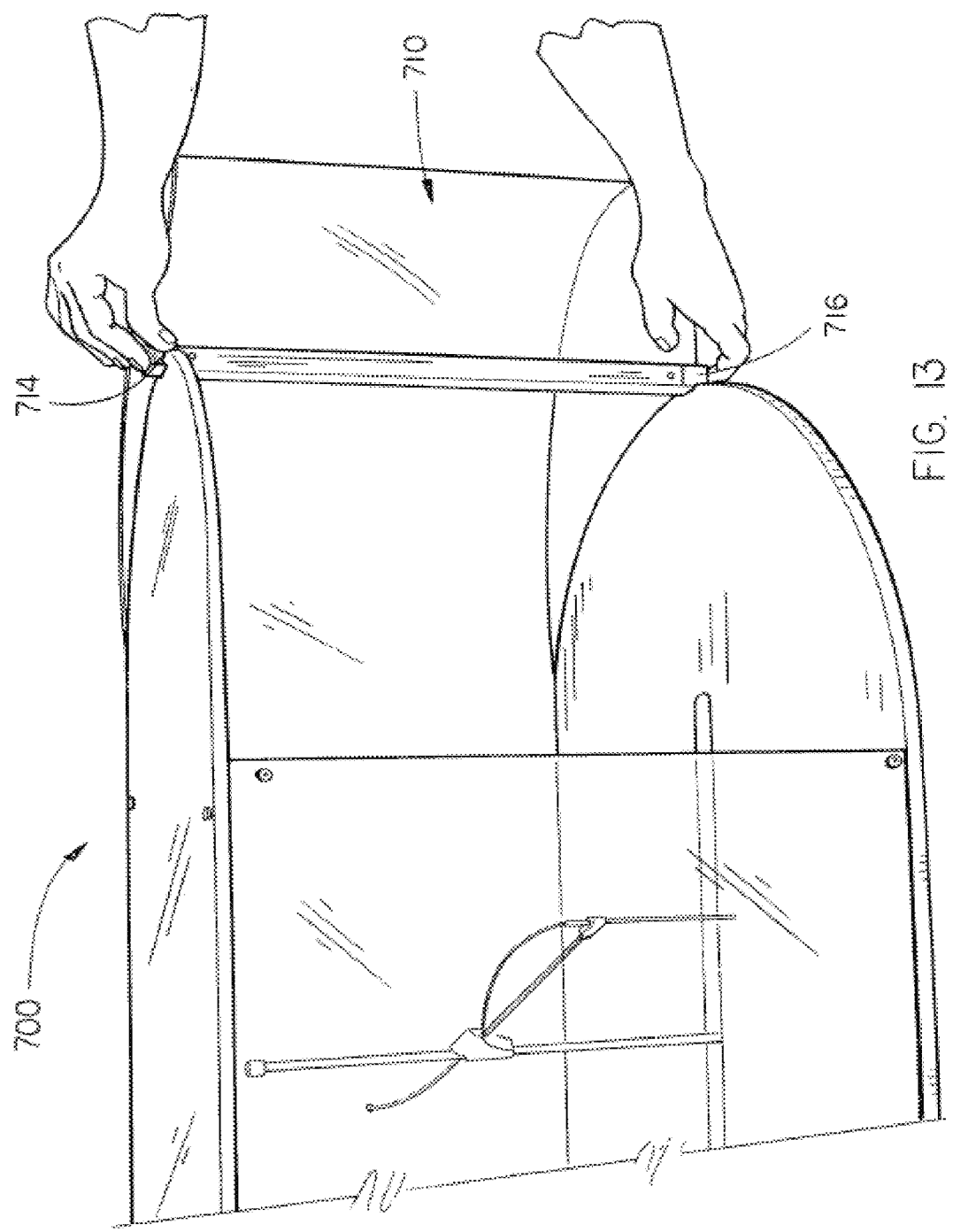
FIG. 13 is a partial front view of the automated sampling or dispensing device enclosure as illustrated in FIG. 12, where one of the flexible sheets of the enclosure is retracted.
Figure 14:
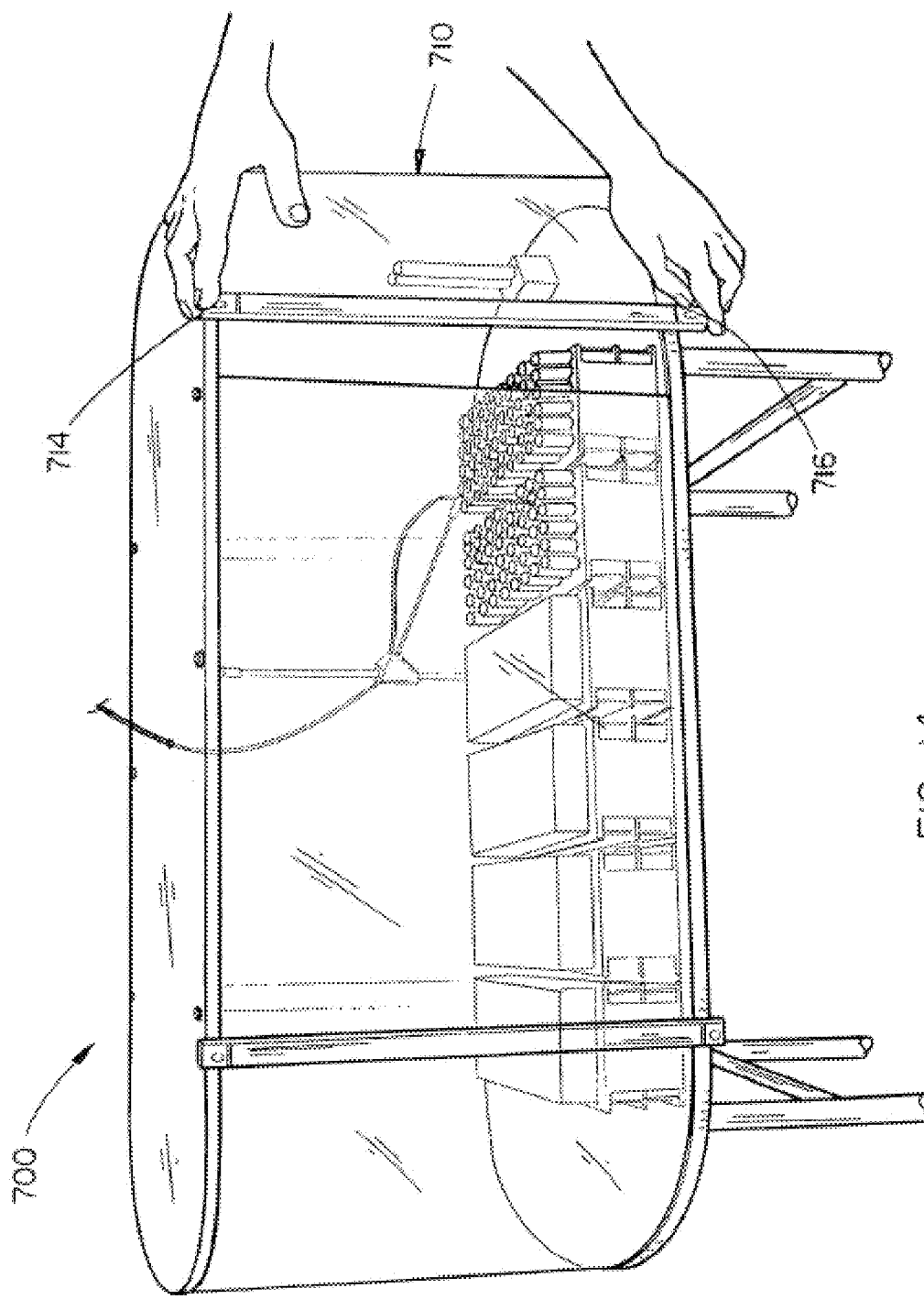
FIG. 14 is a front view of the automated sampling or dispensing device enclosure as illustrated in FIG. 12, where the mechanism of fastening a flexible side shut is demonstrated.

As illustrated in FIGS. 13 and 14, the first end of the first flexible sheet 710 includes a first guide member 714 and a second guide member 716 to allow a user to slide the first flexible sheet 710 along an edge of the support surface 702. In an implementation, the first guide member 714 and the second guide member 716 are press-fit latches allowing a user to secure the flexible sheet at multiple positions along the edge or side of the support surface. For example, a user may release the flexible sheet by applying pressure to the press-fit latches. As illustrated in FIG. 14, a flexible sheet may be moved from a first position to a second position by guiding the first guide member 714 along the edge of the lid 704 while the second guide member is detached from the support surface 710. It is contemplated that additional mechanisms may be employed to guide and secure the flexible sheet at various positions, including fasteners such as clips, pressure-sensitive screws, and so forth. It is further contemplated that a channel may be formed within the support surface to provide an area in which a guide member may slide and be secured.

In the present implementation, the second flexible side 712 includes a first end and a second end. The first end of the second flexible sheet 712 includes a finished edge while the second end of the second flexible sheet 712 is fixedly coupled to the second support member 708. For example, the first end of the second flexible sheet 712 is finished with a hardened-plastic (e.g., Plexiglas®) cover which extends substantially along the length of the first end of the second flexible sheet 712. In addition, at least one guide member is attached to the first end of the second flexible sheet 712 to allow position of the first flexible sheet to be varied. For instance, the first end of the second flexible sheet 712 may include a first guide member 714 and a second guide member 716 to allow a user to slide the second flexible sheet 712 along an edge or side of the support surface 702. In an implementation, the first guide member 714 and the second guide member 716 are press-fit latches allowing a user to secure the flexible sheet at multiple positions along the edge or side of the support surface. It is contemplated that additional mechanisms may be employed to guide and secure the flexible sheet at various positions, including fasteners such as clips, pressure-sensitive screws, and so forth.

Figure 15:
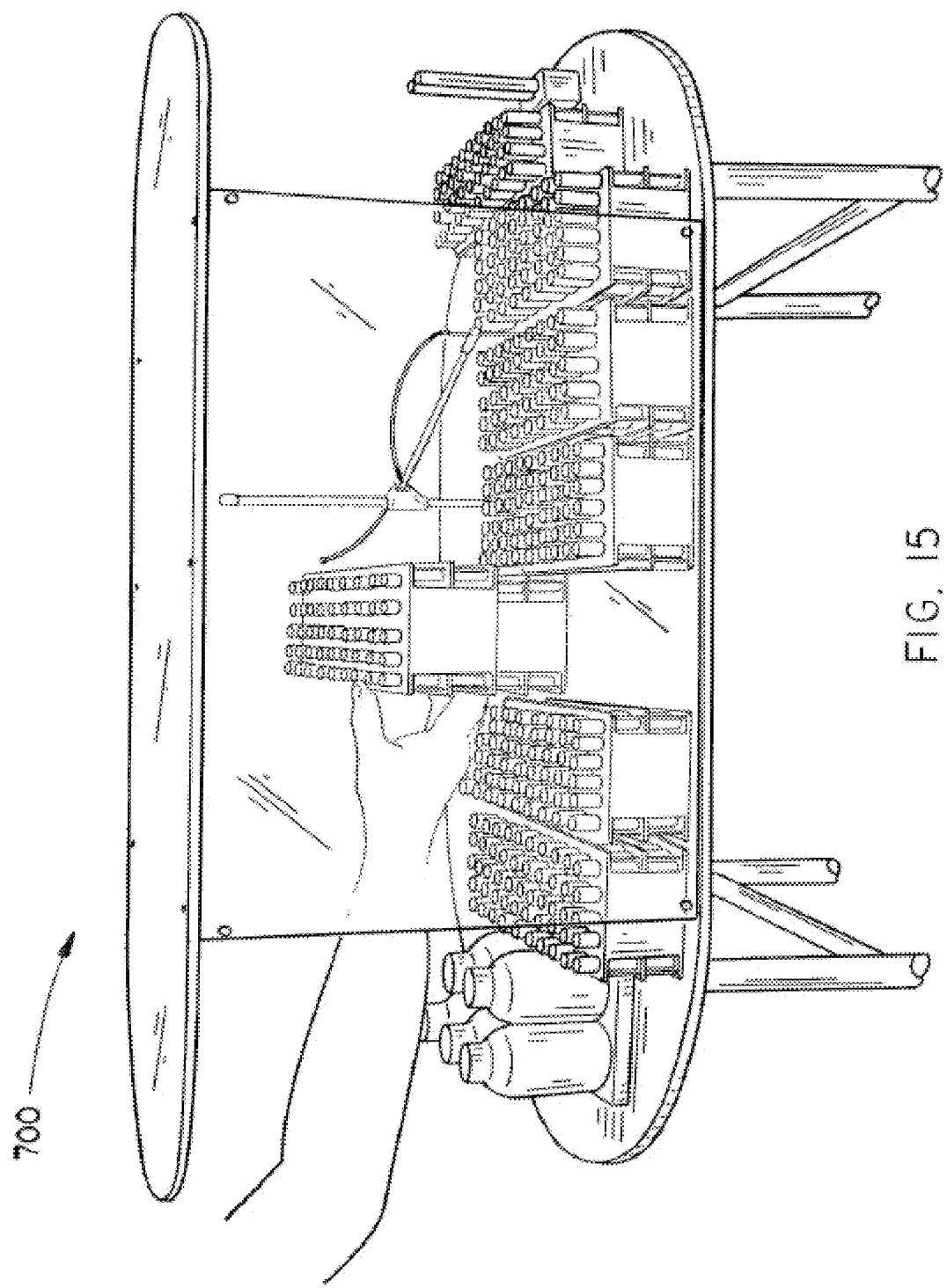
FIG. 15 is a front view of the automated sampling or dispensing device enclosure as illustrated in FIG. 12, where the flexible sheets have been removed.

Referring to FIG. 15, the first and second flexible sheets have been removed to allow access to the support surface 702. In an implementation, the first and second flexible sheets are detachable. The detachable features of such sheets allow a user to load or remove samples efficiently from the support surface 702 so that a user does not have to reposition the sheets in order to gain access to a support surface area. It is contemplated that one or both sheets may be removed depending upon the needs of the user.

Figure 16:
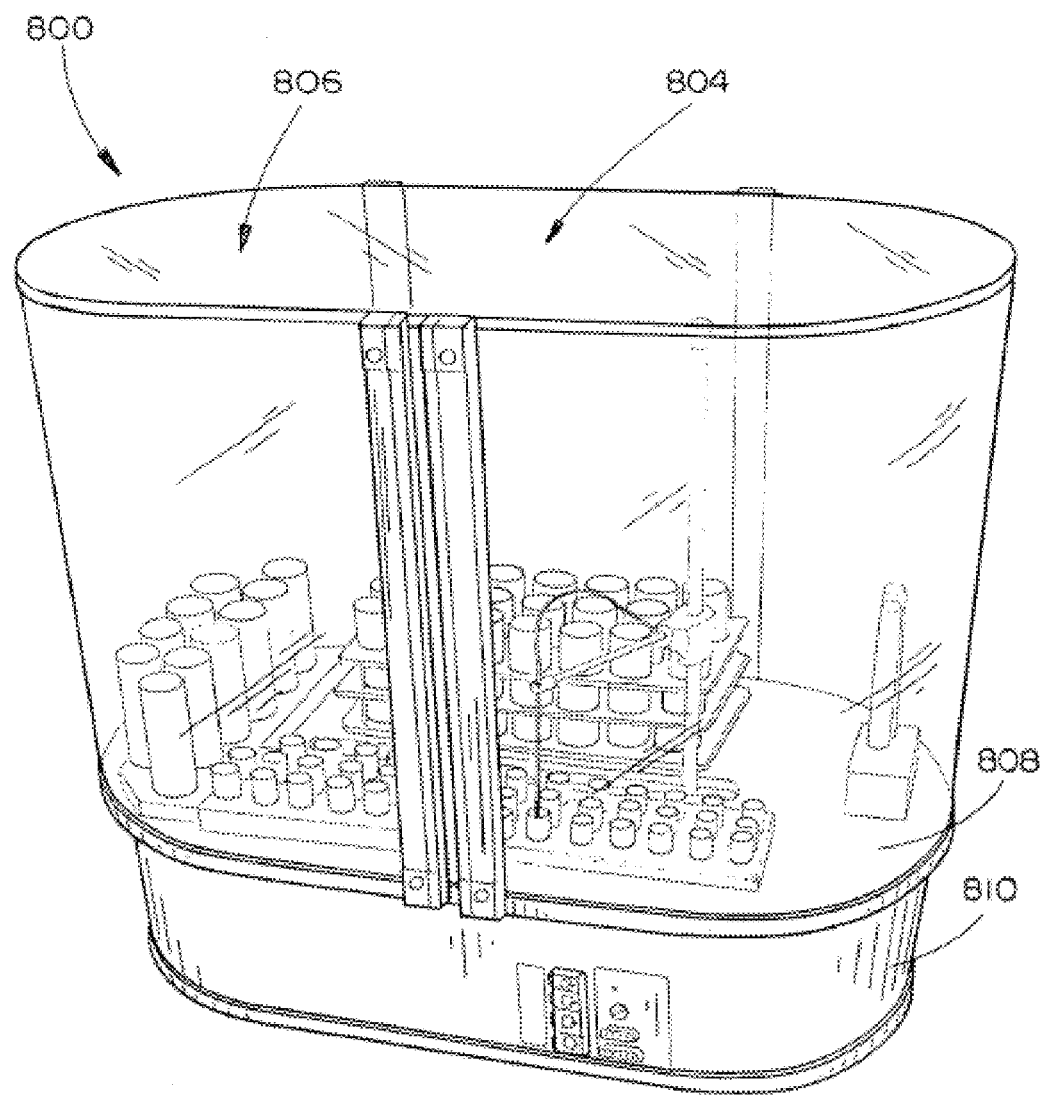
FIG. 16 is an isometric view illustrating an enclosure for a bench top automated sampling or dispensing device in accordance with example implementations of the present disclosure, where the enclosure includes flexible sheets which are in a closed position.
Figure 17:
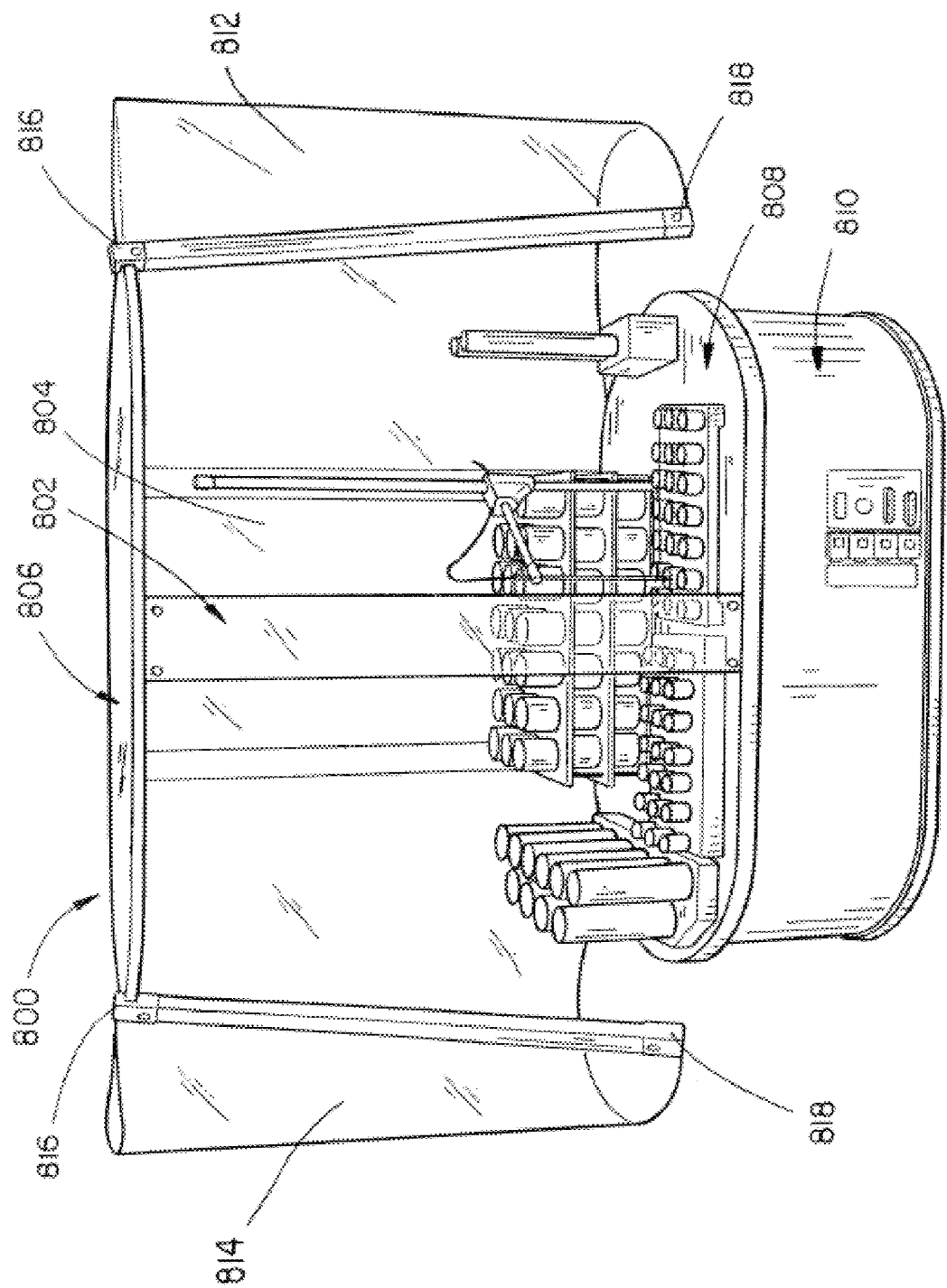
FIG. 17 is a front view of the enclosure for the bench top automated sampling or dispensing device as illustrated in FIG. 16, where the flexible sheets are in an open position.

Referring to FIGS. 16 and 17, an additional example enclosure for enclosing an automated sampling/dispensing device is provided in which the automated sampling/dispensing device is a bench-top automated sampling dispensing device. As illustrated in FIGS. 16 and 17, an enclosure 800 for a bench-top automated sampling dispensing device is configured in a similar manner as the enclosure 700 for a table-top automated sampling/dispensing device. The enclosure 800 includes a first support member 802 and a second support member 804 for supporting a lid 806. In an example implementation, the lid 806 covers a support surface 808 secured to a base 810 of the bench-top automated sampling/dispensing device. In such implementation, the lid 806 is generally equivalent in shape and size to that of the support surface 808, allowing the entire support surface 808 to be enclosed and available for use by a user. Further, the first 802 and second 804 support members are generally perpendicular to the support surface 808.

As illustrated in FIGS. 16 and 17, the first support member 802 and the second support member 804 are centered generally one hundred and eighty degrees (180°) opposite from one another. For example, the first support member 802 is positioned on the front side of the automated sampling/dispensing device (the front side defined as the side including a user power control panel) while the second support member 804 is positioned generally opposite the first support member 802 (e.g., to the rear side of the automated sampling/dispensing device). Moreover, such support members may be mechanically coupled to the lid 806 of the enclosure 800 as well as to the support surface 808. For instance, fasteners such as screws, bolts, nuts, and so forth may be used to fasten the support members to the lid and support surface. In an implementation, all fasteners are either metal-free or coated with an inert plastic coating to prevent interaction of such fasteners with chemical reagents or other substances being used with the automated sampling/dispensing device.

It is contemplated that the lid 806 as well as the first support member 802 and the second support member 804 may be formed of inert, light-weight material including Plexiglas®. It is further contemplated that the enclosure 800 may include an aperture within the lid or at least one of the support members allowing for the automated sampling/dispensing device to be connected with devices external to the enclosure. For example, an aperture may be defined within the lid for allowing a supply tube to the automated sampling/dispensing device to be connected with external laboratory analysis equipment. In another implementation, the enclosure 800 is designed to be airtight allowing the enclosure to contain potentially harmful chemicals without requiring unnecessary exposure to laboratory personal during sample preparation or analysis.

In additional example implementations, as illustrated in FIG. 17, a first flexible sheet 812 and a second flexible sheet 814 are coupled to at least one of the lid 806 or the first support member 802 or the second support member 804. In an implementation, each flexible sheet includes a first and second end. The first end of each flexible sheet includes a finished edge while the second end of each flexible sheet is fixedly coupled to the second support member 804. For example, the first end of the flexible sheet 812 is finished with a hardened-plastic cover (e.g., Plexiglas®) which extends substantially along the length of the first end of the first flexible sheet 812.

In further example implementations, at least one guide member is attached to the first end of each flexible sheet to allow the position of each flexible sheet to be varied. As illustrated in FIG. 17, the first end of each flexible sheet includes a first guide member 816 and a second guide member 818 to allow a user to slide each sheet along an edge of the lid 806 or support surface 808. In an implementation, the first guide member 816 and the second guide member 818 are press-fit latches allowing a user to secure the flexible sheet at multiple positions along the edge or side of the lid or support surface. For example, a user may release the flexible sheet by applying pressure to the press-fit latches. As illustrated in FIG. 17, a flexible sheet may be moved from a first position to a second position by guiding the first guide member 816 along the edge of the lid 806 while the second guide member 818 is detached from the support surface 808. It is contemplated that additional mechanisms may be employed to guide and secure the flexible sheet at various positions, including fasteners such as clips, pressure-sensitive screws, and so forth. It is further contemplated that a channel may be formed within the support surface to provide an area in which a guide member may slide and be secured.

It is contemplated that the first and second flexible sheets may be detachable. The detachable features of such sheets allow a user to load or remove samples efficiently from the support surface 808 so that a user does not have to reposition the sheets in order to gain access to a support surface area. It is contemplated that one or both sheets may be removed depending upon the needs of the user.

Figure 18:
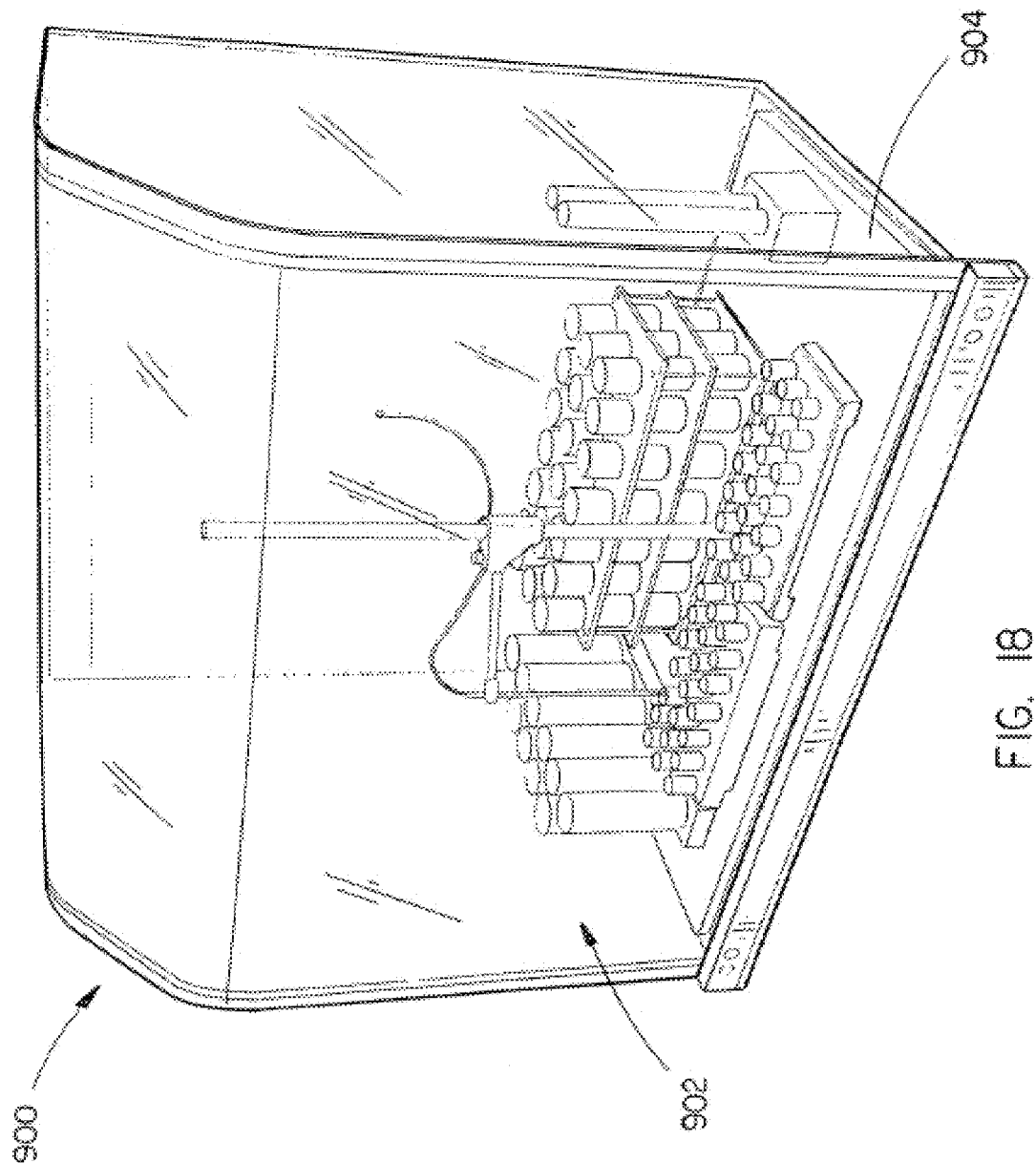
FIG. 18 is an isometric view illustrating an enclosure for an automated sampling or dispensing device in accordance with example implementations of the present disclosure, where the enclosure includes a single flexible front sheet.
Figure 19:
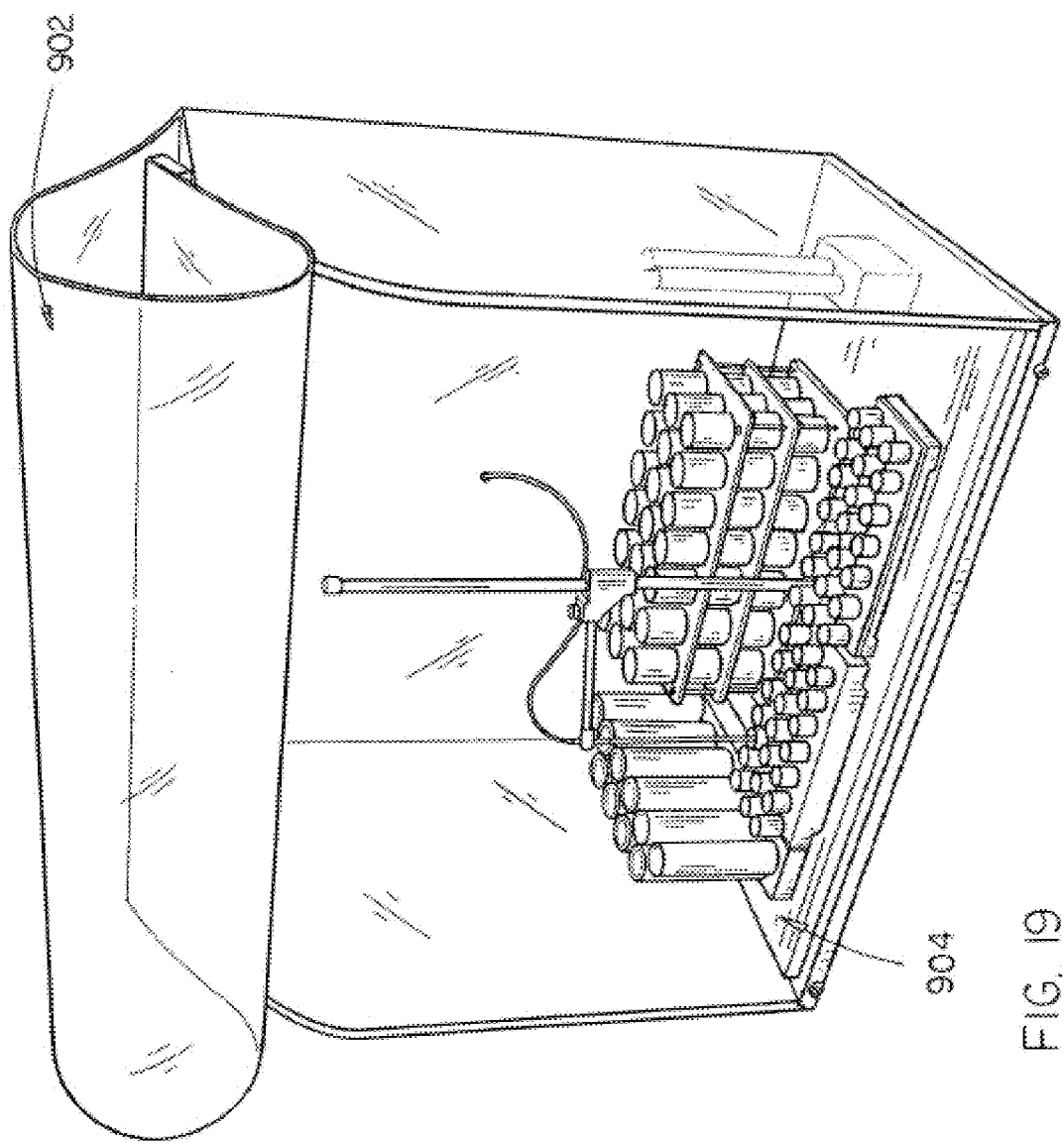
FIG. 19 is an isometric view of the enclosure for the automated sampling or dispensing device as illustrated in FIG. 18, where the front sheet is retracted allowing access to the device.

Referring to FIGS. 18 and 19, a further example enclosure 900 for enclosing an automated sampling/dispensing device is provided in which the enclosure 900 includes a single flexible sheet or panel 902. As illustrated in FIGS. 18 and 19, the enclosure 900 includes a plurality of support walls and a single flexible sheet 902 for enclosing the automated sampling/dispensing device mounted on a support surface 904. For example, the enclosure 900 may include three support walls and the single flexible sheet 902. In such example, a first side support wall and a second side support wall provide support to a rear support wall in which the rear support wall is secured to an edge of the first side support wall and an edge of the second side support wall. The rear support wall is generally opposite to that of the front of the enclosure (e.g., where the front of the enclosure includes the flexible sheet and is used to gain access to the automated sampling/dispensing device). The first and second side support walls are configured to allow the flexible sheet to be rolled along an outer edge of the first side support wall and an outer edge of the second side support wall. It is contemplated that an aperture may be defined within at least one of the plurality of walls for allowing the enclosed apparatus to be connected with external devices or power sources.

With continued reference to FIGS. 18 and 19, the single flexible sheet 902 includes a first and second edge. The first end of the flexible sheet 902 includes a finished edge while the second end of the flexible sheet 902 is fixedly coupled to the rear support wall. For example, the first end of the flexible sheet 902 is finished with a hardened-plastic cover which extends substantially along the length of the first end of the flexible sheet 902. To gain access to the interior of the enclosure 900, the single flexible sheet 902 may be retracted with a first end of the first edge of the single flexible sheet 902 being secured to the outer edge of the first side support wall and a second end of the first edge being secured to the outer edge of the second side support wall. It is contemplated that various mechanisms may be employed to secure the first edge of the flexible sheet 902 to the side support edges including press fit latches, clips, screws, and so forth. In addition, the enclosure 900 may be mounted to an automated sampling/dispensing device for laboratory analysis equipment in which the enclosure may be positioned to enclose such device by securing the enclosure to a support area supporting the device. Moreover, the single flexible sheet may be detachable allowing a user access to the entire support surface area as well as to the over-head support surface area.

Although the presently described enclosure focuses upon the use of such enclosure with an automated sampling/dispensing device, it is contemplated that such enclosure may be employed with a variety of laboratory equipment in accordance with the present disclosure. It is further contemplated that example enclosures may be ventilated to prevent the entry of contaminates such as bacteria or air-borne substances into the external environment. For instance, the air drawn into the enclosure can be passed through a HEPA filter.

Figure 20:
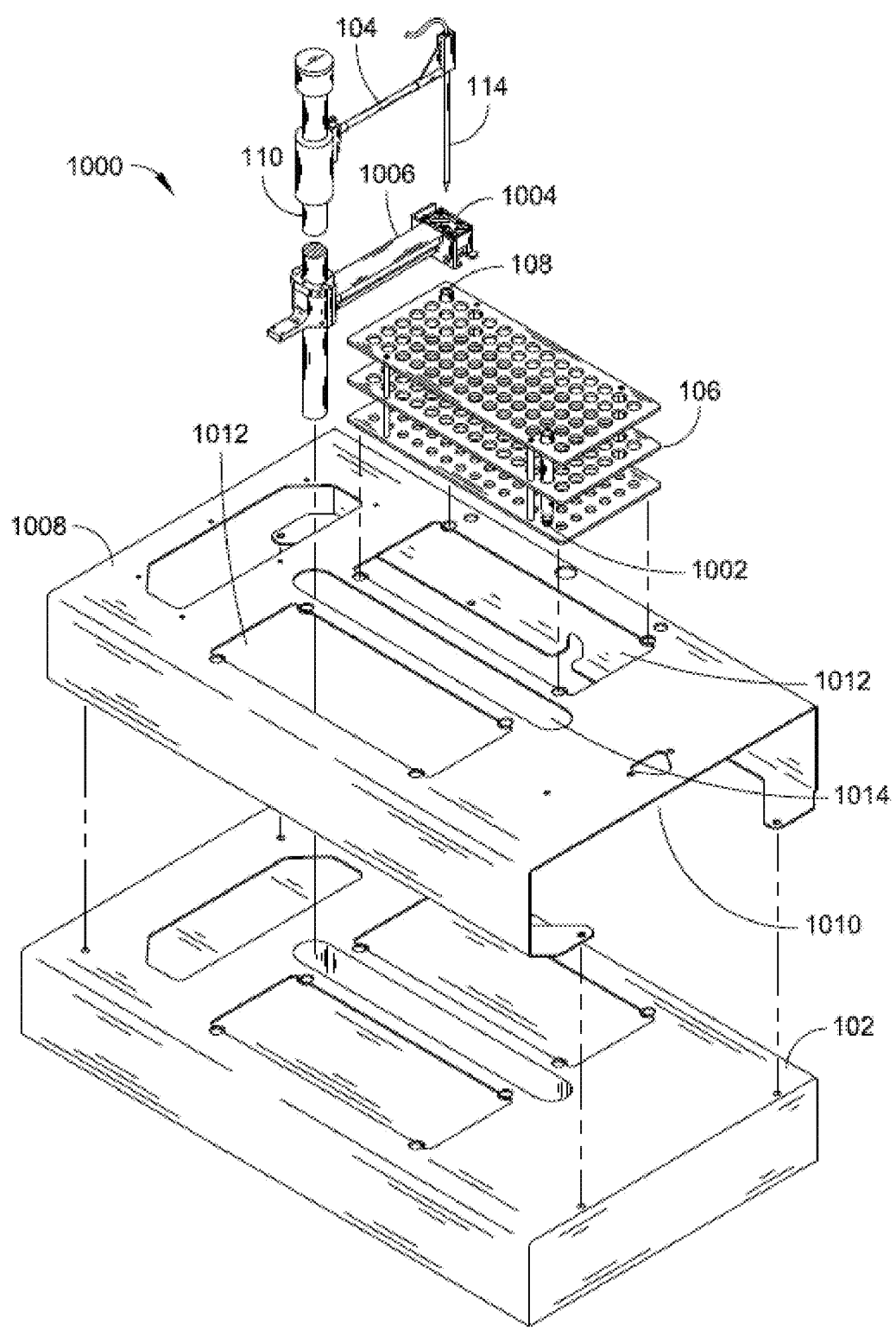
FIG. 20 is a partially exploded isometric view of an automated sampling or dispensing device having a sample identification system in accordance with example implementations of the present disclosure.

Referring now to FIG. 20, a sample identification system 1000 for an automated sampling or dispensing device is shown in accordance with an example implementation of the pressure disclosure. The sample identification system 1000 is configured to verify a sample identity before, during, and/or after sampling and/or dispensing by the automated sampling or dispensing device occurs. As illustrated, the sample identification system 1000 includes a sample identifier 1002 and an identifier capture device 1004. The sample identifier 1002 is configured to provide indicia of the sample, such as a sample positioned in a particular location with respect to the autosampler table top (e.g., table top 102). The sample identifier 1002 may be configured for placement on the autosampler table top, on a sample holder (e.g., sample holder 106), on a sample vessel (e.g., sample vessel 108), or another location for reading by the identifier capture device 1004. In an implementation, the sample identifier 1002 is located on a base or bottom of a sample vessel (e.g., sample vessel 108), such as on the bottom of a test tube, such that the identifier capture device 1004 can access the sample identifier 1002 for processing/imaging of the sample identifier 1002 from a position beneath the sample vessel. In an implementation, the sample identifier 1002 includes a barcode configured for recognition by an optical reader (e.g., a barcode reader), where the barcode is configured to represent a particular sample according to one or more identifiers, including but not limited to, a position within a test rack, a position with respect to a table top, a particular identification number corresponding to a predetermined sampling order of sample vessels, and so forth. The barcode can include a data matrix two-dimensional (2D) barcode, such as a 12×12 matrix, a 13×13 matrix, a 14×14 matrix, or any other suitable matrix. While square matrices are provided as example data matrix barcodes, it is contemplated that rectangular matrices also may be utilized. The sample identifier 1002 can include other identification indicia including, but not limited to: characters and/or patterns configured for recognition by an optical camera or sensor; raised surfaces for recognition by touch sensors, optical sensors, and the like; illumination sources configured to generate a particular color (or wavelength), pattern of light, etc.; other identification indicia configured for recognition by the identifier capture device 1004; and so forth.

In an example implementation, the sample identification system 1000 includes an identifier arm assembly 1006 (which may be separate from or include the sample arm assembly 104) supported by a z-axis support (which may be separate from or include the z-axis support 110). In an implementation, the identifier arm assembly 1006 is configured to move vertically with respect to the z-axis support (shown as 110 in FIG. 20). As illustrated in FIG. 1, the z-axis is aligned with gravity or a vertical axis. The identifier arm assembly 1006 may include the identifier capture device 1004 mounted thereto, such that the identifier capture device 1004 can move to capture/image the sample identifier 1002 of various samples supported by the autosampler table top 102, a sample holder (e.g., sample holder 106), or other support surface. In use, identifier arm assembly 1006 is configured to be moved through space in three dimensions, or about an axis having y-motion that is a substantially rotary motion and along an axis having x-motion which is an at least substantially horizontal linear motion or translation, and along a z-axis that is an at least substantially vertical, linear motion or translation. As such, the identifier arm assembly 1006 may be configured for movement through an R-theta range of motion, an x-y range of motion, and the like, such as between a rest position and an operating position configured to image sample vessels including sample identifiers 1002. In an implementation, the identifier arm assembly 1006 is configured to move independently from the sample arm assembly 104.

Figure 21A:
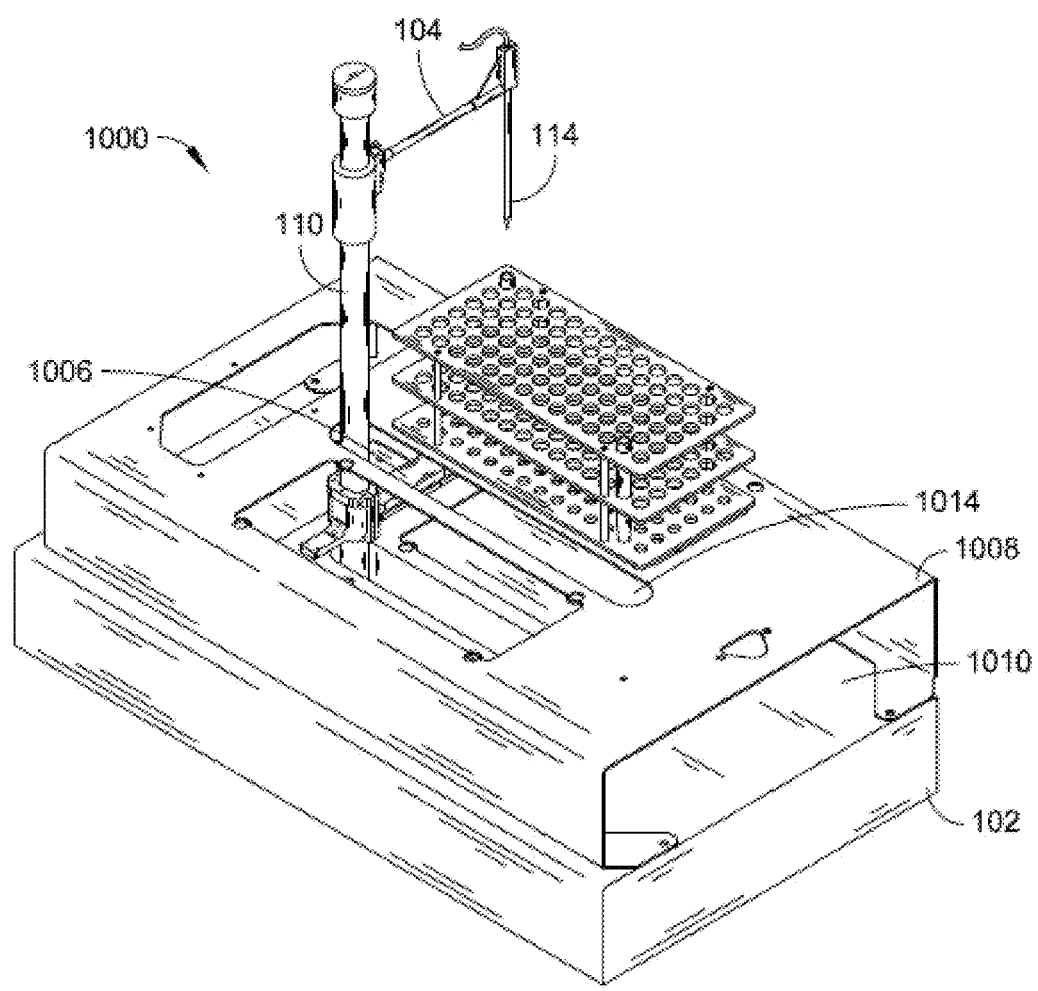
FIG. 21A is an isometric view of the automated sampling or dispensing device of FIG. 20.
Figure 21B:
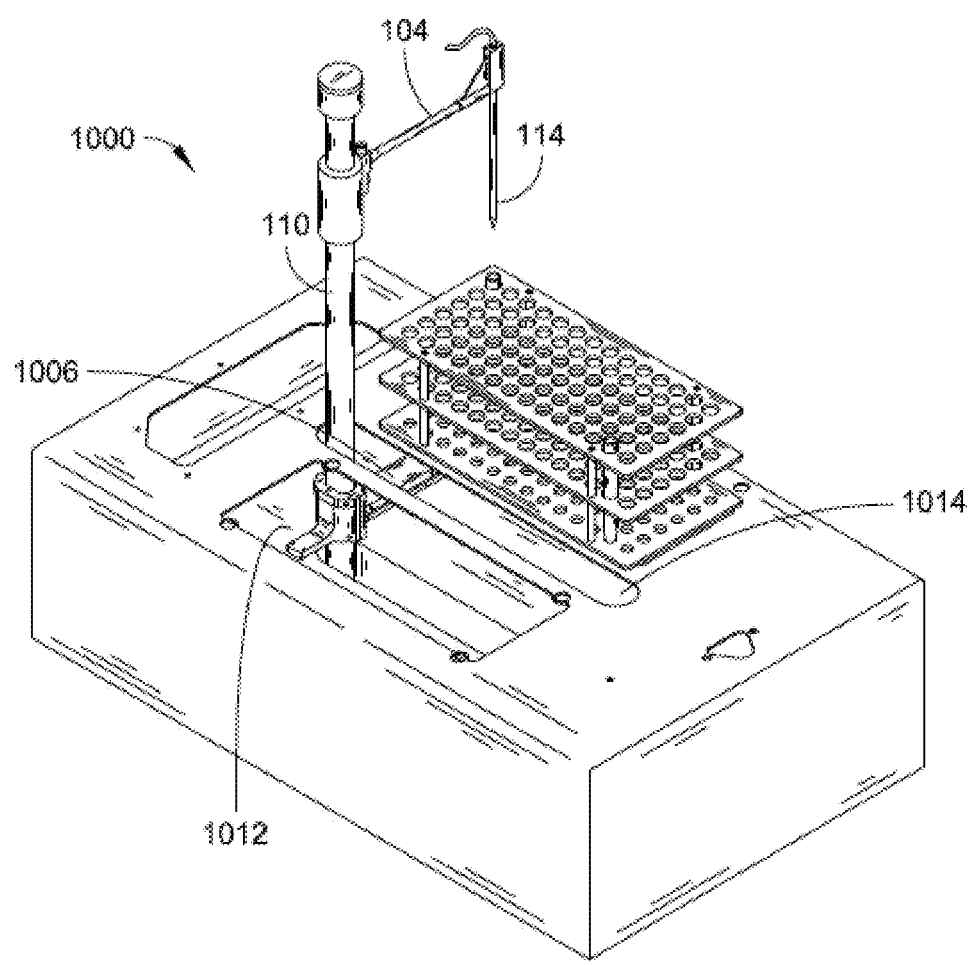
FIG. 21B is an isometric view of an automated sampling or dispensing device having a sample identification system in accordance with example implementations of the present disclosure.
Figure 21C:
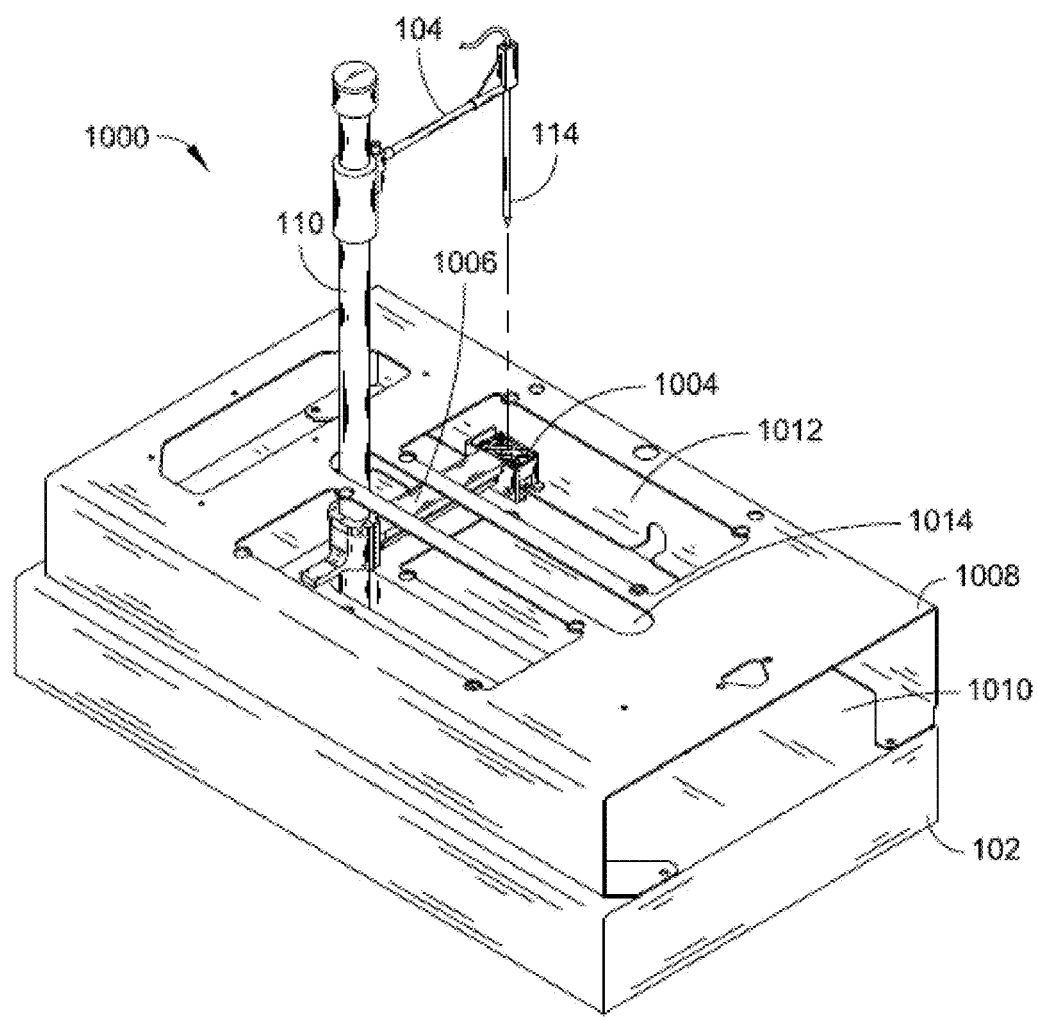
FIG. 21C is an isometric view of the automated sampling or dispensing device of FIG. 20 shown in an operating position.
Figure 22:
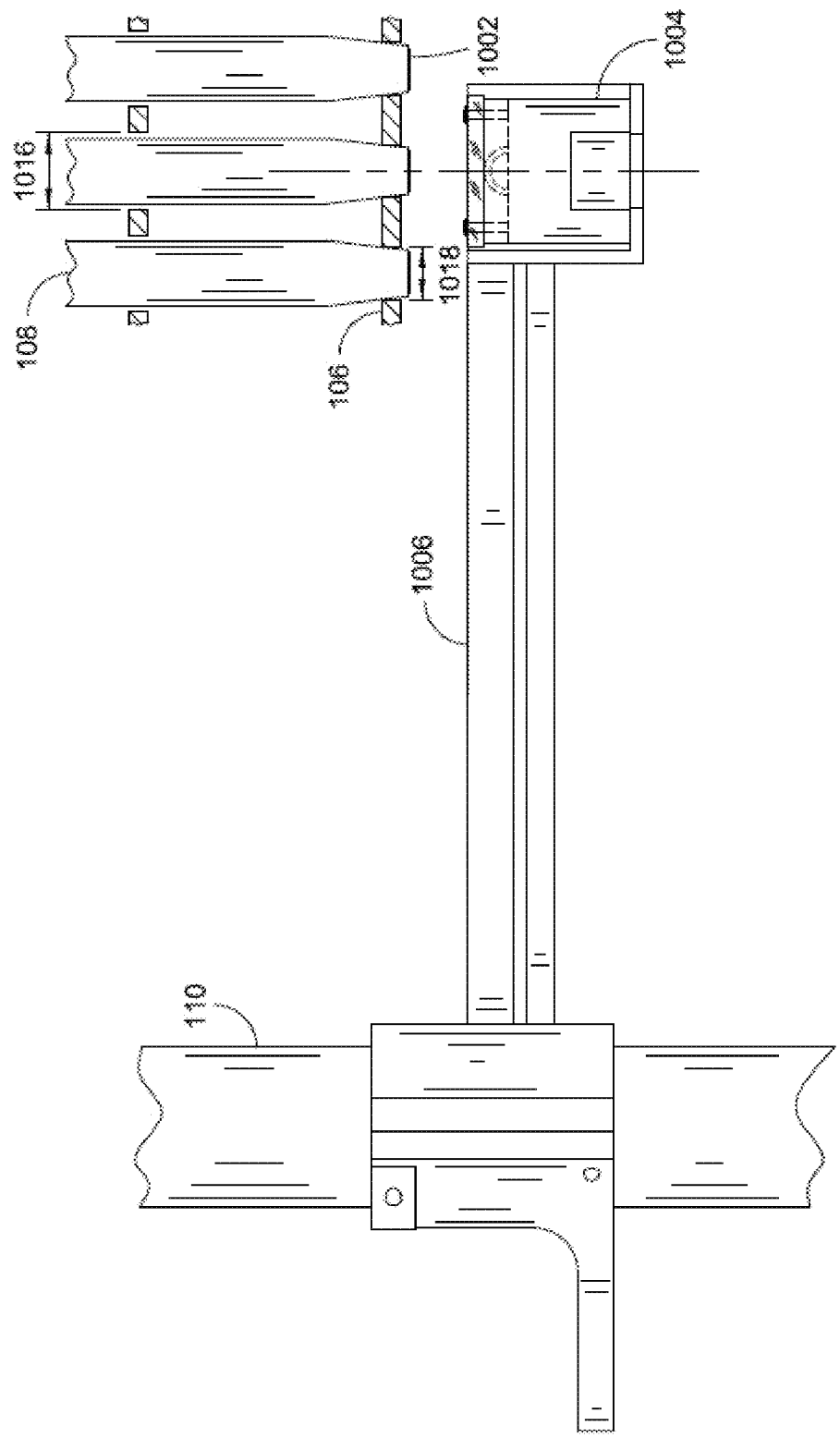
FIG. 22 is a partial side view of an identifier arm assembly in position beneath a sample holder having sample vessels with sample identifiers.

In an implementation, as shown in FIG. 20, the autosampler includes a raised surface 1008 configured to be supported by the autosampler table top 102. The raised surface 1008 can support sample holders and sample vessels for access by the sample probe 114. The raised surface 1008 may be positioned with respect to the table top 102 such that the raised surface 1008 and the table top 102 define a gap 1010 into which the identifier arm assembly 1006 and identifier capture device 1004 can enter for access to the underside of the sample vessels (e.g., sample vessels 108) and associated sample identifiers 1002. For instance, in implementations, the raised surface 1008 defines gaps 1012 in the surface over which the sample vessels 108 having sample identifiers 1002 positioned on a bottom surface are situated. In this manner, the sample identifiers 1002 at the base or bottom of the sample vessels 108 are accessible to the identifier capture device 1004 when positioned beneath the raised surface 1008 in the gap 1010 (such as shown in FIG. 22). The raised surface 1008 can also define a center slot 1014 to correspond to at least a portion of the center slot 120 of the table top 102 to permit motion of the sample arm assembly 104 across the raised surface 1008 and the corresponding portion of the table top 102 (such as shown in FIGS. 21A through 21C).

Figure 23A:
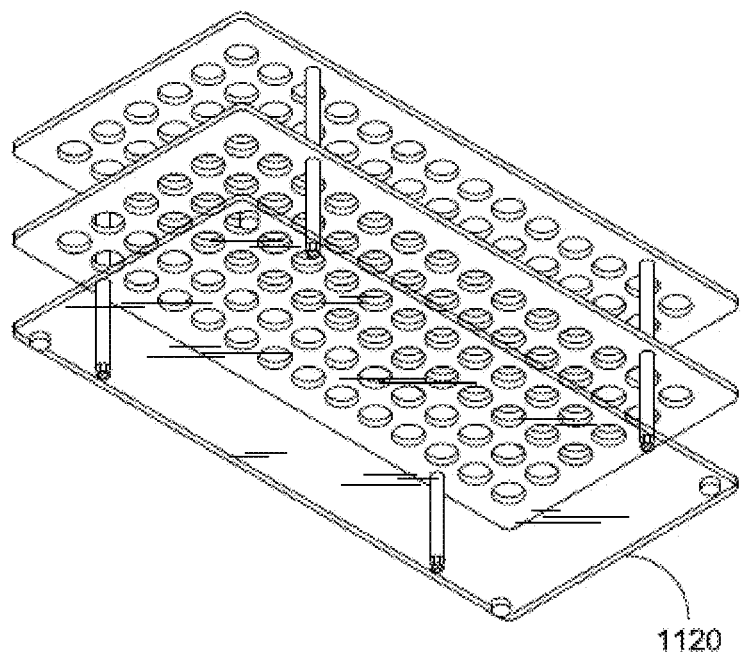
FIG. 23A is an isometric view of a sample holder including a substantially transparent bottom.
Figure 23B:
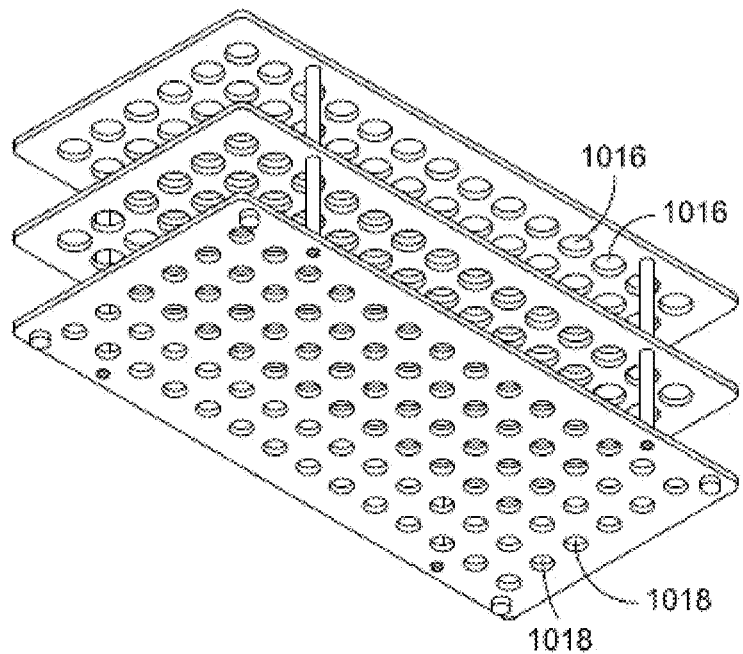
FIG. 23B is an isometric view of a sample holder including a first set of apertures configured to hold sample vessels and a second set of apertures on a bottom portion of the sample holder.

In example implementations, the autosampler includes sample holders (e.g., sample racks 106) configured to permit the identifier capture device 1004 to read the sample identifier 1002. For example, a base of the sample holders 106 may be constructed from a substantially clear, light transmissive, or transparent material. In other embodiments, the sample holder 106 may be constructed with an open bottom. Use of a light transmissive or transparent material may protect the identifier capture device 1004 from inadvertent contact with sample fluids within the sample vessels 108. In an implementation, the sample holders are formed of, or are coupled with, a material configured to reduce or eliminate glare associated with light when utilizing the identifier capture device 1004. Alternatively or additionally, the identifier capture device 1004 can include a protective coating or covering to protect the identifier capture device 1004 from inadvertent contact with the sample fluids. Such coating or covering of may be configured to reduce or eliminate glare associated with light when utilizing the identifier capture device 1004. In an implementation (such as shown in FIG. 23A), the sample holder 106 includes a substantially transparent bottom 1120, through which the image capture device 1004 can recognize the sample identifier 1002 on a base of a sample vessel 108 supported by the sample holder 106. In an implementation (such as shown in FIGS. 22 and 23B), the sample holder 106 defines a first set of apertures 1016, through which the sample vessels 108 may pass, and a second set of apertures 1018 which prohibit at least a portion of the sample vessels 108 from completely passing through. For instance, the first set of apertures 1016 can have a larger cross-sectional area (e.g., larger diameter with larger circular cross-sectional area) than the second set of apertures 1018, where the second set of apertures 1018 have a cross-sectional area that is smaller than a cross-sectional area of the sample vessels 108 (e.g., the diameter of the second set of apertures 1018 is less than the diameter of a portion of the sample vessels 1018). Such a configuration of apertures may provide an exposed bottom portion of the sample vessel 108 such that the sample identifier 1002 is unobstructed with respect to the identifier capture device 1004. In an example implementation, the sample holder 106 includes a raised base, such that the sample vessels 108 within the holder 106 are positioned over the autosampler table top 102 with a gap between the base of the sample holder 106 and the autosampler table top 102. Such a configuration may permit the identifier capture device 1004 access beneath the sample holder to read the sample identifier 1002. It is contemplated that the size, shape, and materials comprising the sample holder 106 may vary depending on the type, size, and shape of the identifier capture device 1004 used in the sample identification system 1000, and the type of samples to be analyzed (e.g., corrosive, inert, and so forth).

Figure 24:
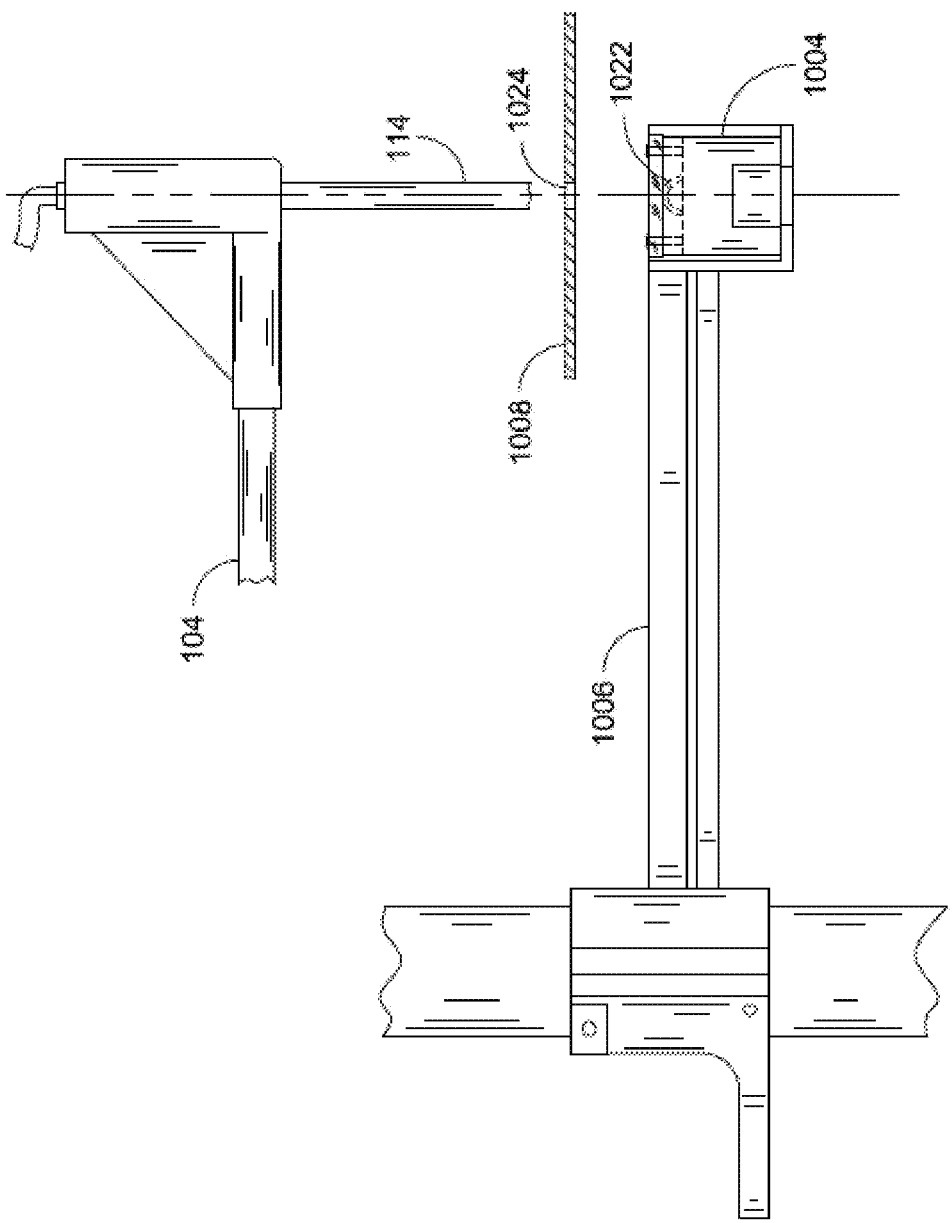
FIG. 24 is a partial side view of an identifier capture device and a sample probe, where the identifier capture device is aligned with the sample probe.

The autosampler may be configured to align the identifier capture device 1004 with the sample probe 114. For example, as shown in FIG. 24, the identifier capture device 1004 includes an alignment light source 1022 configured to project light (e.g., a light beam) toward the sample probe to provide a visual indication of an alignment of the identifier capture device 1004 with the sample probe 114. In an implementation, the raised surface 1008 defines an aperture 1024 through which the alignment light source 1022 can project the light toward the sample probe 114. Where the positioning of the sample probe 114 with respect to the identifier capture device 1004 is not aligned, one or more of the sample arm assembly 104 and the identifier arm assembly 1006 can be repositioned until the alignment is satisfactory. The repositioning can be accomplished through an automatic, motorized movement of the sample arm assembly 104 and the identifier arm assembly 1006 (e.g., through control of drive assembly 100) or through manual means. For example, one or more of the sample arm assembly 104 and the identifier arm assembly 1006 can be secured with a set screw, with press fit, with a friction clamp, and so forth. The alignment may assist in accuracy of the correspondence between the imaged sample identifier 1002 by the identifier capture device 1004 and the actual sample drawn by the sample probe 114 from the sample vessel 108.

Figure 25:
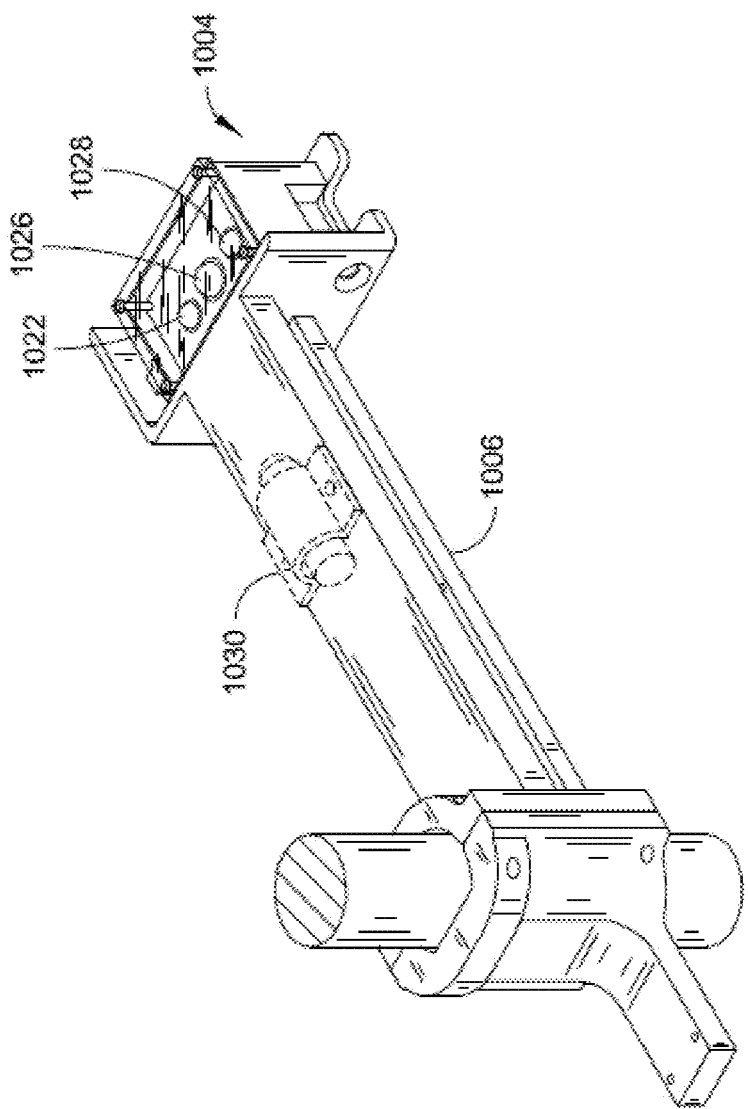
FIG. 25 is an isometric view of an identifier arm assembly having an identifier capture device.

The identifier capture device 1004 is configured to capture, image, or otherwise recognize the sample identifier 1002. Accordingly, in an implementation such as shown in FIG. 25, the identifier capture device 1004 includes an imaging device 1026, a light source 1028 (e.g., a flash source), and the alignment light source 1022. The imaging device 1026 can capture video images of the sample identifiers 1002 and surrounding areas, such that the imaging device 1026 can be associated with a display for displaying the captured images, such as on a live or continuous basis. In an implementation, the imaging device is configured to provide still images of a target. The light source 1028 may be configured to illuminate the bottom of the sample vessels 108 such that the sample identifier 1002 has increased visibility to the imaging device 1026 in order to image the sample identifier 1002. In an implementation, the identifier capture device 1004 is aided by an external light source 1030 to provide illumination in addition to or instead of the light source 1028. For example, the external light source 1030 can be mounted on the identifier arm assembly 1006.

Figure 26A:
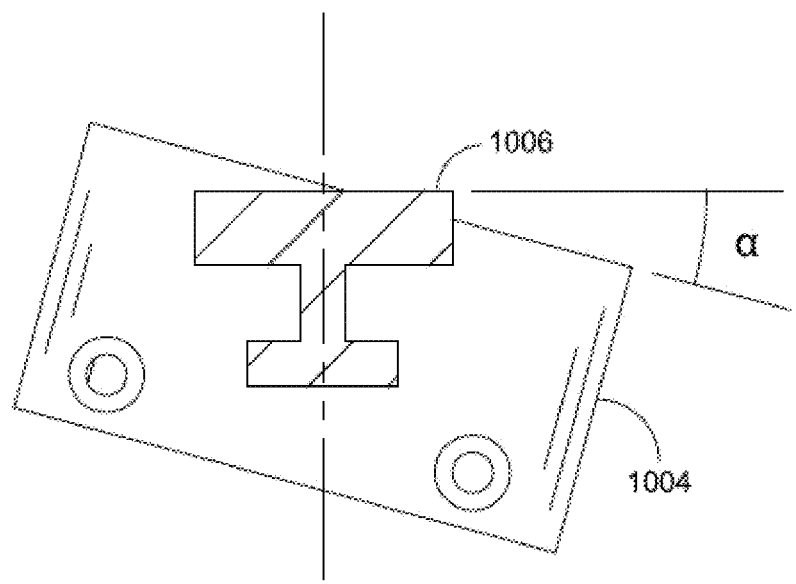
FIG. 26A is a side view of an identifier arm assembly relative to an identifier capture device for a system, such as the system shown in FIG. 20, where the identifier arm assembly is positioned substantially perpendicular to the alignment axis, and where the identifier capture device is positioned at an angle from perpendicular to the alignment axis.
Figure 26B:
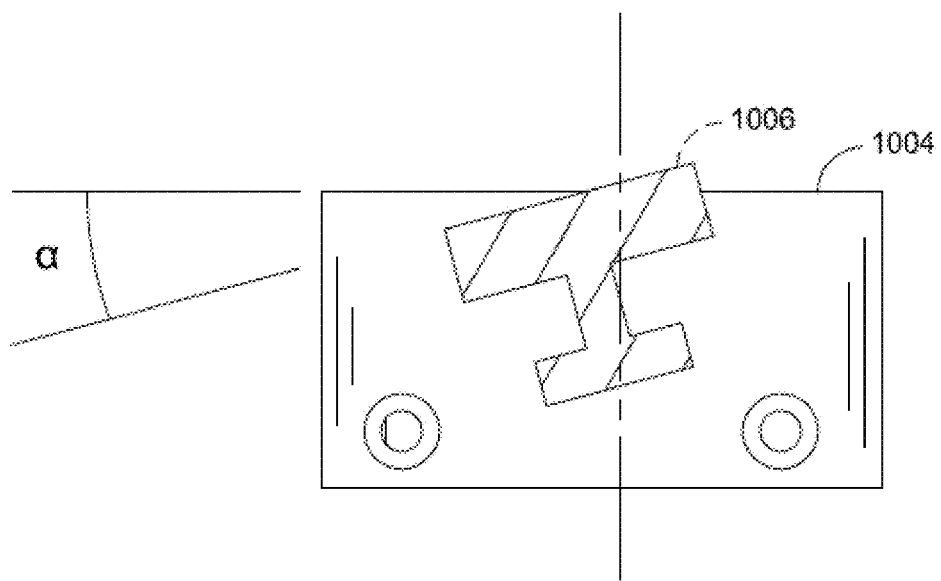
FIG. 26B is a side view of an identifier arm assembly relative to an identifier capture device for a system, such as the system shown in FIG. 20, where the identifier capture device is positioned substantially perpendicular to the alignment axis, and where the identifier arm assembly is positioned at an angle from perpendicular to the alignment axis.

In implementations, the identifier capture device 1004 is angled relative to the identifier arm assembly 1006, such that the imaging device 1026 views the sample identifier 1002 on the base of the sample vessel 108 at an angle from the horizontal or with respect to the orientation of the autosampler table top. For example, as shown in FIG. 26A, the identifier capture device 1004 and the identifier arm assembly 1006 are oriented at an angle of alpha (α) (e.g., 15 degrees) relative to each other, where a top surface of the identifier arm assembly 1006 is substantially perpendicular to the alignment axis (e.g., substantially parallel to the surface of table top). In FIG. 26B, the identifier capture device 1004 and the identifier arm assembly 1006 are oriented at an angle of alpha (α) (e.g., 15 degrees) relative to each other, where a top surface of the identifier capture device 1004 is substantially perpendicular to the alignment axis (e.g., substantially parallel to the surface of table top). Various configurations of the angle are contemplated, where the angle utilized may depend on the particular imaging device 1026 utilized in the identifier capture device 1004.

The sample identification system 1000 is configured to verify data associated with the sample identifier 1002, and correspondingly, the sample uniquely associated with the sample identifier 1002, before, during, or after sampling of the sample by the autosampler sampling probe (e.g., sample probe 114). The sample identification system 1000 may collect and process data associated with the sample identifier 1002, where the data can include, but is not limited to, the location of a sample (e.g., a location on the autosampler table top 102, a location within a sample rack 106, a particular sample vessel 108, and so forth), a timestamp of when a sample is taken (e.g., by the sample probe 114), presence or absence of a sample, type or extent of analysis to be performed on a sample, dilution factor, and the like. In an implementation, the sample identifier 1002 is read by the identifier capture device 1004 for conversion to a serial number, where data associated with the serial number is associated with the particular sample vessel that includes the sample identifier 1002. In this manner, the sample identifier 1002 can associate data including, but not limited to, the location of a sample, timestamp of when a sample is taken, presence or absence of a sample, type or extent of analysis to be performed on a sample, dilution factor, and the like with a particular sample in the vessel, where the data can be stored in a memory device of a data system to be correlated with the serial number stored by the sample identifier 1002. In an implementation, the sample identification system 1000 can be configured for dilution factor control of a sample. For example, the data associated with a particular sample identifier 1002 can include a dilution factor for offline or online dilution of a sample. In an implementation, the sample identification system 1000 is configured to populate data of prepared samples, such as by filling in standards data into data tables automatically, based on the sample identifier 1002 and the results of a sample analysis by an analyzer (e.g., mass spectrometer, gas chromatograph, liquid chromatograph, and the like) of the particular sample.

The sample identifier 1002 can be associated with and/or comprise information including, but not necessarily limited to: a sample vial identification number, a destination vial identification number, a dilution factor (DF), a final volume, a sample volume, a diluent volume, a diluent location, and so forth. For example, a first barcode is placed on a sample vial and associated with a desired dilution factor and a desired final volume. A destination vial includes a second barcode associated with the first barcode. The system 1000 uses information obtained from the first barcode to dilute a portion of a sample contained in the sample vial. For instance, the system 1000 identifies the destination vial using the second barcode and deposits a portion of the sample into the destination vial. The system 1000 also deposits an amount of diluent sufficient to provide the DF and final volume specified by the first barcode.

In another embodiment, the first barcode is representative of a sample vial identification number, and the sample identification number is associated with a desired dilution factor and a desired final volume. In some embodiments, a user interface (e.g., a graphical user interface) included with an information handling system device operatively coupled with the sample identification system 1000 via a communications interface is used to associate the first barcode with the desired dilution factor and the desired final volume. For instance, the desired dilution factor and the desired final volume can be stored in an electronic database with the first barcode. A destination vial includes a second barcode associated with the first barcode (e.g., via the electronic database). The system 1000 uses information associated with the first barcode in the electronic database to dilute a portion of the sample contained in the sample vial. For instance, the system 1000 identifies the destination vial using the association with the second barcode and deposits a portion of the sample into the destination vial. The system 1000 also deposits an amount of diluent sufficient to provide the DF and final volume specified in the electronic database.

However, these off-line embodiments are provided by way of example only and are not meant to limit the present disclosure. In other embodiments, dilution of a sample can be performed on-line. For example, the system 1000 uses information obtained from a barcode to dilute a portion of a sample contained in the sample vial by mixing the sample portion with an amount of diluent sufficient to provide a desired DF and a desired final volume as specified by a first barcode, associated with the first barcode in an electronic database, and so forth.

The data collected by the sample identification system 1000 may be transferred to another system for identity verification. In an example implementation, the data collected by the sample identification system 1000 is transferred to a laboratory information management system (LIMS) and/or a laboratory instrument to verify the identity of a measured sample. The identifier capture device 1004 may be configured for wired or wireless data transfer between the sample identification system 1000 and the LIMS, laboratory instrument, or other device. In an example embodiment, the identifier capture device 1004 is configured for fiber optic data transfer. The identifier capture device 1004 may be configured for control by the sample identification system 1000 via wired or wireless control mechanisms.

A sample identification system 1000, including some or all of its components, can operate under computer control. For example, a processor can be included with or in a sample identification system 1000 to control the components and functions of systems 1000 described herein using software, firmware, hardware (e.g., fixed logic circuitry), manual processing, or a combination thereof. The terms "controller," "functionality," "service," and "logic" as used herein generally represent software, firmware, hardware, or a combination of software, firmware, or hardware in conjunction with controlling the systems 1000. In the case of a software implementation, the module, functionality, or logic represents program code that performs specified tasks when executed on a processor (e.g., central processing unit (CPU) or CPUs). The program code can be stored in one or more computer-readable memory devices (e.g., internal memory and/or one or more tangible media), and so on. The structures, functions, approaches, and techniques described herein can be implemented on a variety of commercial computing platforms having a variety of processors.

A processor provides processing functionality for the system 1000 and can include any number of processors, micro-controllers, or other processing systems, and resident or external memory for storing data and other information accessed or generated by the system 1000. The processor can execute one or more software programs that implement techniques described herein. The processor is not limited by the materials from which it is formed or the processing mechanisms employed therein and, as such, can be implemented via semiconductor(s) and/or transistors (e.g., using electronic integrated circuit (IC) components), and so forth.

The system 1000 also includes a memory. The memory is an example of tangible, computer-readable storage medium that provides storage functionality to store various data associated with operation of the system 1000, such as software programs and/or code segments, or other data to instruct the processor, and possibly other components of the system 1000, to perform the functionality described herein. Thus, the memory can store data, such as a program of instructions for operating the system 1000 (including its components), and so forth. It is noted that while a single memory is described, a wide variety of types and combinations of memory (e.g., tangible, non-transitory memory) can be employed. The memory can be integral with the processor, can comprise stand-alone memory, or can be a combination of both. The memory can include, but is not necessarily limited to: removable and non-removable memory components, such as random-access memory (RAM), read-only memory (ROM), flash memory (e.g., a secure digital (SD) memory card, a mini-SD memory card, and/or a micro-SD memory card), magnetic memory, optical memory, universal serial bus (USB) memory devices, hard disk memory, external memory, and so forth. In implementations, the system 1000 and/or the memory can include removable integrated circuit card (ICC) memory, such as memory provided by a subscriber identity module (SIM) card, a universal subscriber identity module (USIM) card, a universal integrated circuit card (UICC), and so on.

The system 1000 includes a communications interface. The communications interface is operatively configured to communicate with components of the system 1000. For example, the communications interface can be configured to transmit data for storage in the system 1000, retrieve data from storage in the system 1000, and so forth. The communications interface is also communicatively coupled with the processor to facilitate data transfer between components of the system 1000 and the processor (e.g., for communicating inputs to the processor received from a device communicatively coupled with the system 1000 and/or communicating output to a device communicatively coupled with the system 1000. It is noted that while the communications interface is described as a component of a system 1000, one or more components of the communications interface can be implemented as external components communicatively coupled to the system 1000 via a wired and/or wireless connection. The system 1000 can also comprise and/or connect to one or more input/output (I/O) devices (e.g., via the communications interface) including, but not necessarily limited to: a display, a mouse, and so on.

The communications interface and/or the processor can be configured to communicate with a variety of different networks including, but not necessarily limited to: a wide-area cellular telephone network, such as a 3G cellular network, a 4G cellular network, or a global system for mobile communications (GSM) network; a wireless computer communications network, such as a WiFi network (e.g., a wireless local area network (WLAN) operated using IEEE 802.11 network standards); an internet; the Internet; a wide area network (WAN); a local area network (LAN); a personal area network (PAN) (e.g., a wireless personal area network (WPAN) operated using IEEE 802.15 network standards); a public telephone network; an extranet; an intranet; and so on. However, this list is provided by way of example only and is not meant to limit the present disclosure. Further, the communications interface can be configured to communicate with a single network or multiple networks across different access points.

Figure 27:
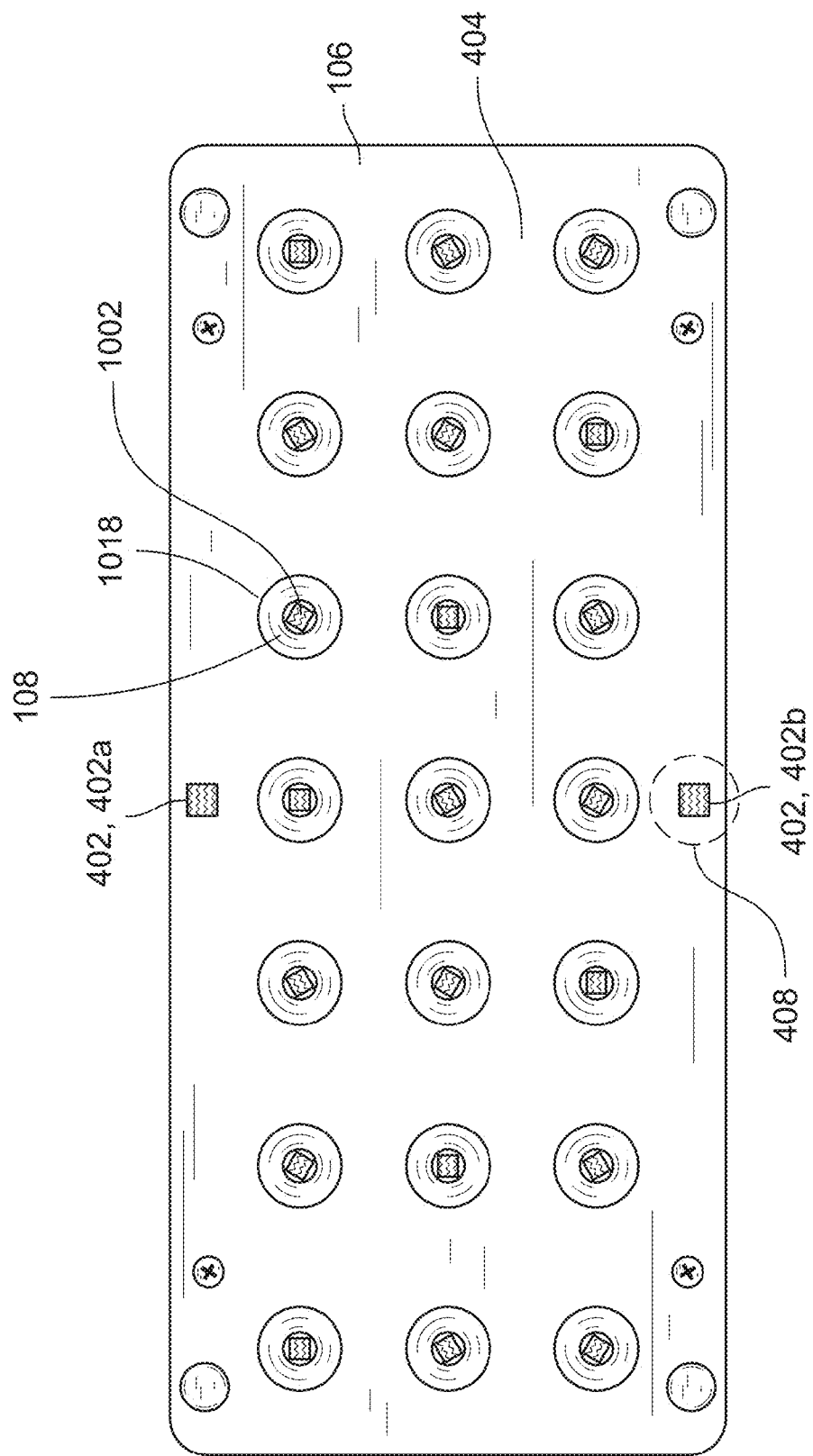
FIG. 27 is a bottom perspective view of a sample holder including sample holder identifiers in accordance with example implementations of the present disclosure.

In an implementation, as shown in FIG. 27, the sample holder 106 includes a sample holder identifier 402 positioned on a bottom portion 404 of the sample holder 106. The bottom portion 404 can correspond to a side of the sample holder 106 that is opposite or distal a side of the sample holder 106 that receives the sample vessels 108 via the first set of apertures 1016 (e.g., for holding the sample vessels upright for access by the sample probe 114). For example, the bottom portion 104 can define the second set of apertures 1018, the bottom portion can include the transparent bottom 1120, or so forth. The sample holder identifier 402 is identifiable by an identifier capture device, such as the identifier capture device 1004 of the sample identification system 1000. The sample holder identifier 402 provides a unique identification of the sample holder 106, where such unique identification can correspond to identification information including, but not limited to, sample identities, analysis methods associated with samples held in sample vessels 108 in the sample holder 106, elements/species associated with samples held in sample vessels 108 in the sample holder 106, dilution factors associated with samples held in sample vessels 108 in the sample holder 106, weights associated with samples held in sample vessels 108 in the sample holder 106, final volumes associated with samples held in sample vessels 108 in the sample holder 106, and the like. Such corresponding identification information can be stored in a memory device accessible by one or more components of the automated sampling device or associated scientific instrumentation coupled thereto. For example, the sample holder identifier 402 may include one or more of a barcode or a QR code associated with the unique identification of the sample holder 106. In an implementation, the sample holder identifier 402 includes a data matrix two-dimensional barcode in a square matrix form (e.g., a 12×12 matrix, a 13×13 matrix, a 14×14 matrix, a 144×144 matrix etc.). While square matrices are provided as example data matrix barcodes, it is contemplated that rectangular matrices (e.g., a 8×18 matrix, a 16×48 matrix, etc.), or any other suitable matrix also may be utilized. The sample holder identifier 402 can include other identification indicia including, but not limited to: characters and/or patterns configured for recognition by an optical camera or sensor; raised surfaces for recognition by touch sensors, optical sensors, and the like; illumination sources configured to generate a particular color (or wavelength), pattern of light, etc.; other identification indicia configured for recognition by the identifier capture device 1004; and so forth.

While the sample holder identifier 402 is shown in FIG. 27 on the bottom portion 404 of the sample holder 106, other configurations of the sample holder identifier 402 with respect to the sample holder 106 can be utilized, including, but not limited to, the sample holder identifier 402 being located on a top portion, a side portion, a support post portion, or the like, such that an identifier capture device can recognize the sample holder identifier 402. For example, in an implementation, the sample holder identifier 402 is positioned on a top portion of the sample holder 106 (e.g., proximate the first set of apertures 1016), for access by an identifier capture device associated with the sample arm assembly 104, the z-axis support 110, the sample probe 114, or other perspective above the table top 102.

In an implementation, the sample holder identifier 402 includes more than one sample holder identifier (e.g., FIG. 27 shows two sample holder identifiers, labeled 402a and 402b), where each sample holder identifier corresponds to a different orientation of the sample holder 106. For example, sample holder identifier 402a can include identification information that corresponds to a top, front, or side orientation of the sample holder 106, whereas sample holder identifier 402b can include identification information that corresponds to a bottom, back, or different side orientation of the sample holder 106. As used herein, the orientation of the sample holder 106 can refer to a placement orientation used to align the sample holder 106 on a surface of an autosampler or sample identification device for processing of samples (e.g., on raised surface 1008, on table top 102, etc.). For example, the placement orientation can identify an orientation and/or position of the sample holder 106 relative to the center slot 1014, the sample arm assembly 104, the z-axis support 110, the sample probe 114, or other component or portion of the automated sampling device 100.

Figure 28A:
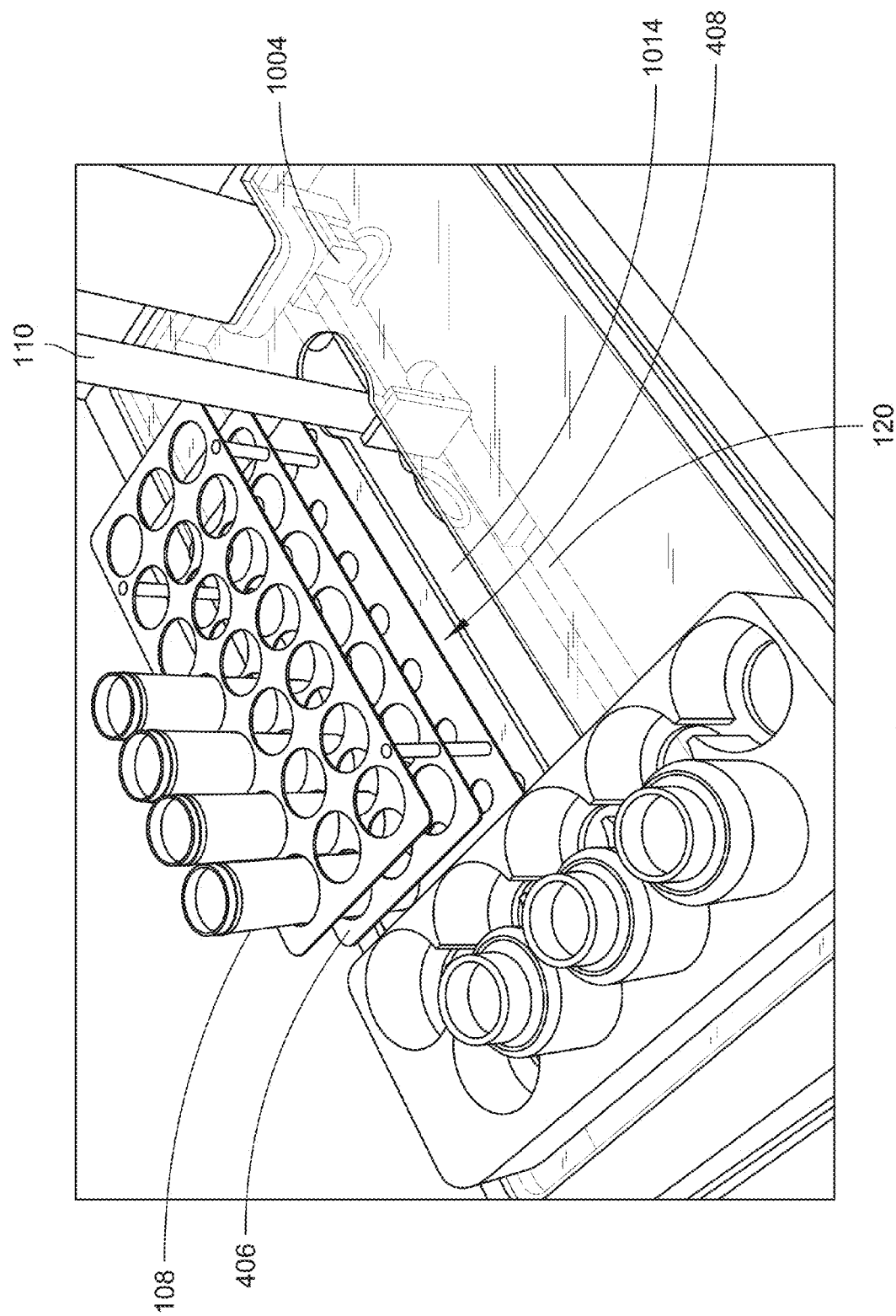
FIG. 28A is an isometric view of an automated sampling or dispensing device having sample vessels positioned in slots, numbers one to four, distal to a z-axis support.
Figure 28B:
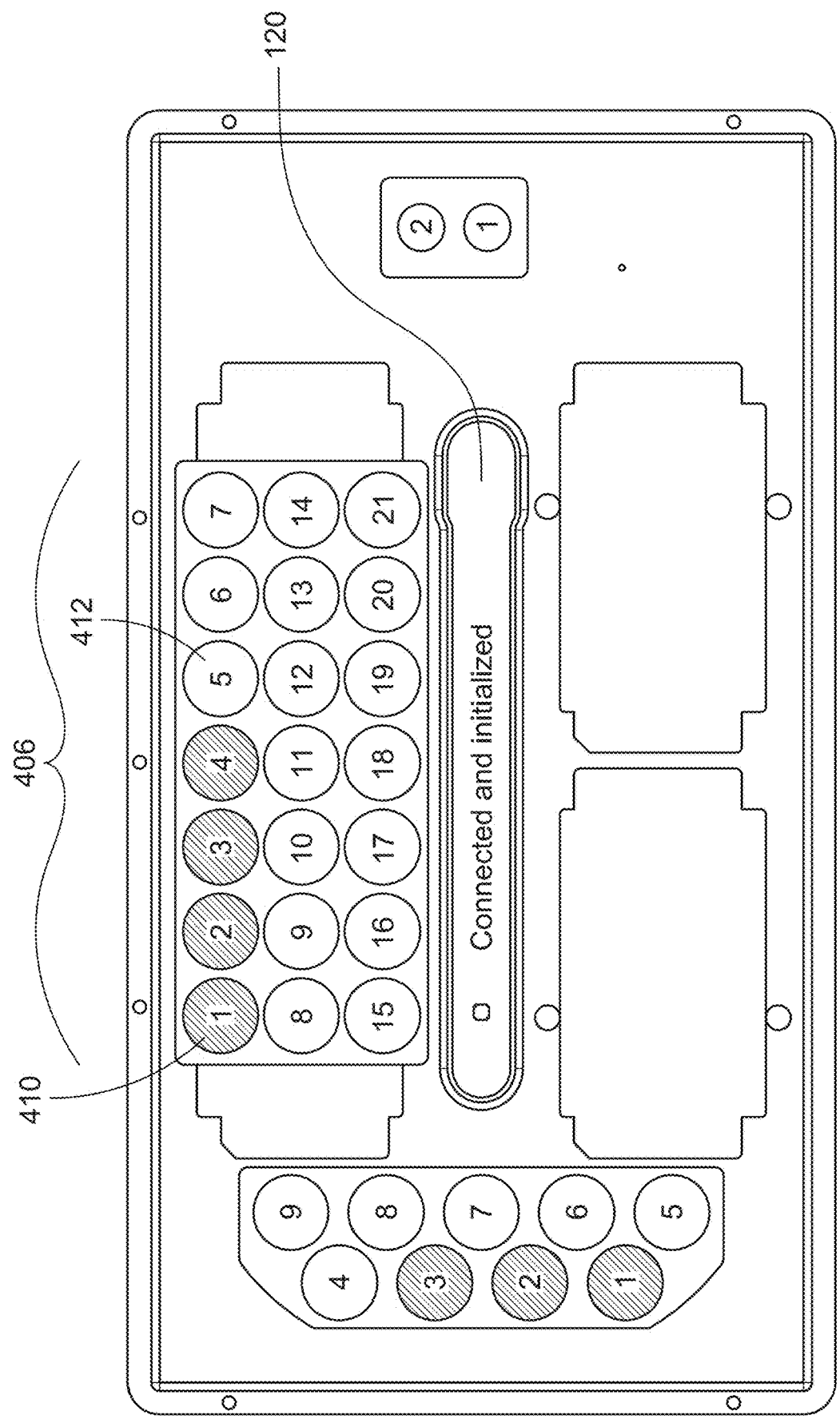
FIG. 28B is a diagrammatic top view showing the automated sampling or dispensing device detecting sample vessels positioned in slots, numbers one to four, distal to a center slot through which a z-axis support can pass.
Figure 29A:
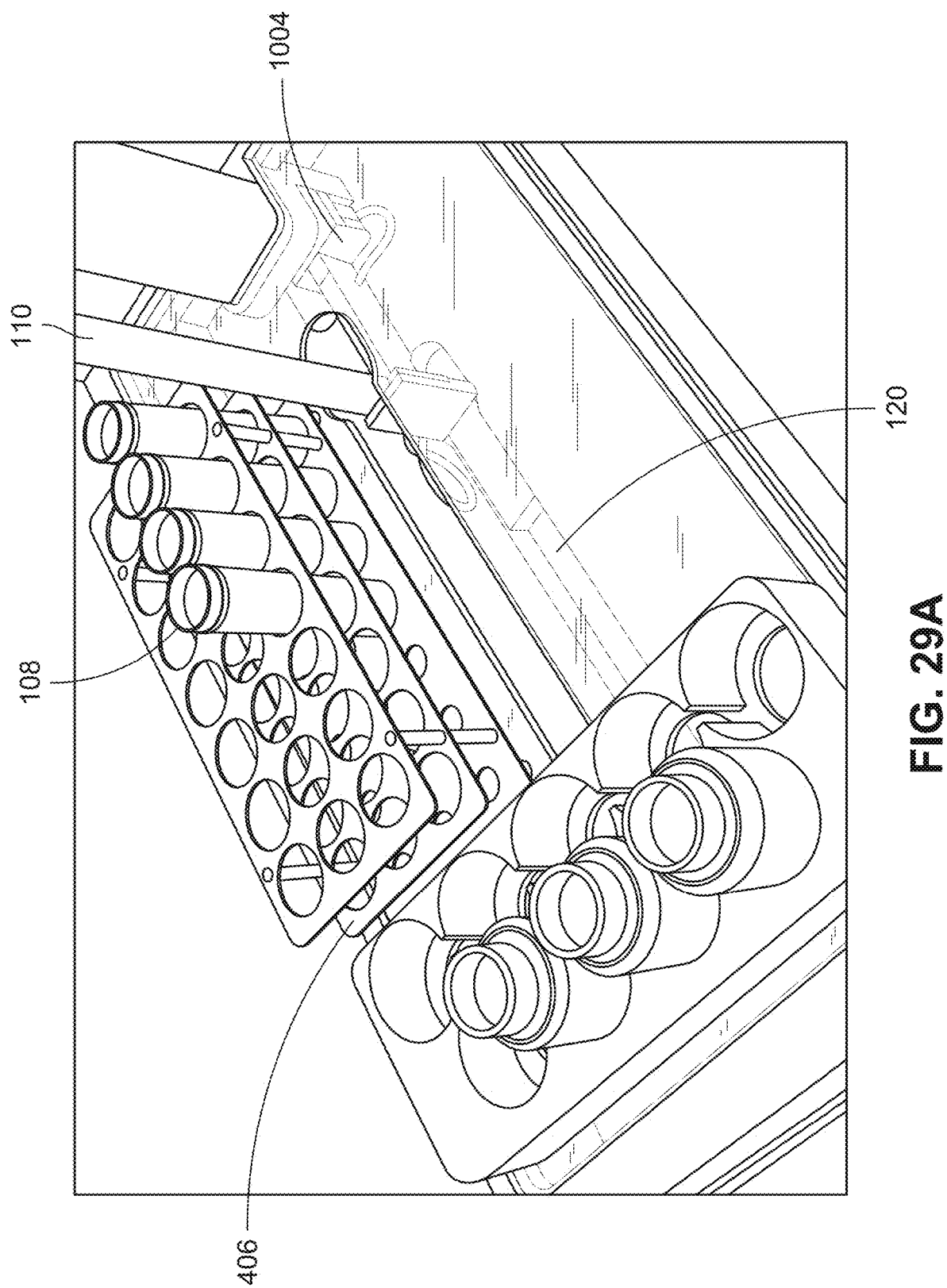
FIG. 29A is an isometric view of an automated sampling or dispensing device with sample vessels positioned in slots, numbers one to four, adjacent to a z-axis support.

In an implementation, as depicted in FIGS. 28A and 28B, sample vessels 108 are positioned in slots 406 (or apertures), numbers one to four, distal to a z-axis support 110 of an automated sampling or dispensing device, where the slots correspond to positions in the sample holder 106 configured to hold sample vessels 108. The sample holder 106 can include labels to identify the particular slots 406 to a user, such as to provide an order in which to place the sample vessels within the slots 406. For example, the sample holder 106 can include labels to identify the slots 406 with the numbers corresponding to those diagrammatically shown in FIG. 28B. In an implementation, the sample holder identifier 402b is positioned on the same side of the sample holder 106 as the slot 406 labeled with position one, such that when the sample holder 106 is placed in the reverse or flipped orientation, each of the sample holder identifier 402b and the side of the sample holder 106 having the slot 406 labeled with position one will be adjacent the center slot 120 (e.g., as shown in FIG. 29A). For example, the sample holder identifier 402a can be positioned on the opposite side of the sample holder 106 (e.g., on the bottom portion of the sample holder 106) as the slot 406 labeled with position one (e.g., the first designation in a series, such as the numbering series of slots 406), such that when the sample holder 106 is placed in the standard orientation, the sample holder identifier 402a will be adjacent the center slot 120, and the side of the sample holder 106 having the slot 406 labeled with position one will be distal the center slot 120 (e.g., as shown in FIG. 28A). The sample holder 106 can include a sample holder identifier 402 configured to provide dynamic data associated with the sample holder 106 including, but not limited to, a unique rack identification (ID), a position of the sample holder 106, an orientation of the sample holder 106 (e.g., a standard orientation, a reverse or flipped orientation, etc.), an alignment of the sample holder 106, and the like. For example, the sample holder identifier 402 can correspond to the dynamic data stored in memory, whereby a data controller, system processor, or the like can assign and/or update the dynamic data, such as responsive to user input, responsive to automatic implementation by the system 100, or the like. In an implementation, the system 1000 determines an orientation a sample holder 106 (e.g., standard orientation shown in FIGS. 28A, 28B; reverse or flipped orientation shown in FIGS. 29A, 29B) by positioning the identifier capture device 1004 in a sample holder read position (shown as 408 in FIGS. 27 and 28A) that corresponds to a position underneath the sample holder identifier 402 when the sample holder 106 is placed on the table top 102, the raised surface 1008, or otherwise positioned for allowing access to the sample vessels 108 by the sample probe 114. Generally, the sample holder reader position corresponds to the positioning of the identifier capture device 1004 to read the sample holder identifier 402. The system 1000 can include a plurality of sample holder read positions when multiple sample holders 106 are present on the on the table top 102, the raised surface 1008, etc. In an implementation, a user can input information associated with the placement of the sample holders 106, including location and number of the individual sample holders 106, whereby the system 1000 can automatically scan only the relevant sample holder read positions to identify the orientation of the sample holders 106 present (e.g., by ignoring sample holder read positions at locations where no sample holder 106 is present).

The sample holder identifier 402 can then inform the system 1000 about whether the sample holder 106 is in a standard orientation or a reverse or flipped orientation. The system 1000 can manipulate the operational positioning of the sample probe 114 based on the detected orientation of the sample holder 106. For example, when the sample holder 106 is determined to be in the standard orientation (e.g., the identifier capture device 1004 detects the sample holder identifier 402A in the sample holder read position), the system 1000 can operate according to a standard orientation protocol. The standard orientation protocol can involve, for example, initially positioning the sample probe 114 to measure the sample vessel 108 in position one of slots 406, shown in FIG. 28B, where position one is distal to the center slot 120, and proceeding to position the sample probe 114 to sequentially measure the remaining sample vessels 108 based on slot number (e.g., continuing to slots two, three, and four). When the sample holder 106 is determined to be in the reverse or flipped orientation (e.g., the identifier capture device 1004 detects the sample holder identifier 402B in the sample holder read position), the system 1000 can operate according to a reverse orientation protocol. The reverse orientation protocol can involve, for example, initially positioning the sample probe 114 to measure the sample vessel 108 in position one of slots 406, shown in FIG. 29B, where position one is adjacent to the center slot 120, and proceeding to position the sample probe 114 to sequentially measure the remaining sample vessels 108 based on slot number (e.g., continuing to slots two, three, and four). In implementations, the system 1000 can provide an alert (e.g., via a display device) based upon detection of the particular orientation of the sample holder 106. For example, when a reverse orientation of the sample holder 106 is detected, the system 1000 can display an alert to an operation, notifying that the sample holder 106 is in the reverse orientation. The system 1000 can receive user input to continue operation with the sample holder 106 in the reverse orientation (e.g., by implementing the reverse orientation protocol), or alternatively, can receive user input to delay operation, such as to permit repositioning of the sample holder 106 and/or sample vessels 108. When user input is received to delay operation, the system 1000 may scan any sample holder identifiers 402 at the sample holder read position and/or may scan the sample identifiers 1002 of any sample vessels 108 present in the sample holder upon resuming operation, such as to determine whether the user placed the sample holder 106 in the standard orientation, in the reverse orientation, changed the order of sample vessels 108 within the sample holder 106, change the number of sample vessels 108 within the sample holder 106, or the like.

In implementations, the sample vessel positions shown in FIG. 28A correspond with a graphical representation of the sample vessels positions within the sample holder 106 shown on a communications interface operably coupled to the automated sampling or dispensing device 100, as shown in FIG. 28B. The communications interface can also show the presence (shown as 410) or absence (shown as 412) of the sample vessel 108 within a particular sample slot 406, whereby detection of the sample vessel 108 within a particular slot 406 is automatically shown as the presence 410 of the sample vessels 108 via the communications interface. For example, the automated sampling or dispensing device (e.g., via identifier capture device 1004) can detect sample vessels 108 positioned in the slots 406 via the sample identifiers 1002, where the communications interface can provide a graphical representation (e.g., as shown in FIG. 28B) of the presence of the sample vessels 108 relative to the orientation of the sample holder 106 (e.g., via detection of the sample holder identifier 402 information), such that the sample vessels 108 are shown distal the center slot 120 in the proper order/configuration. The presence of the particular sample vessels 108 in the slots 406 and the orientation of the sample holder 106 provide the system 1000 with the information as to which slots 406 the sample probe 114 should position above during its operation protocol. The communications interface can generate a sample list based on sample identifiers 1002 associated with the sample vessels 108 positioned in the sample holder 106 and based on the sample holder identifier 402 positioned on the sample holder 106. Such sample list can be generated after scanning the sample identifiers 1002 and the sample holder identifier 402, and can be populated with data associated with the analysis of the samples once completed, or on an individual sample vessel basis.

Figure 29B:
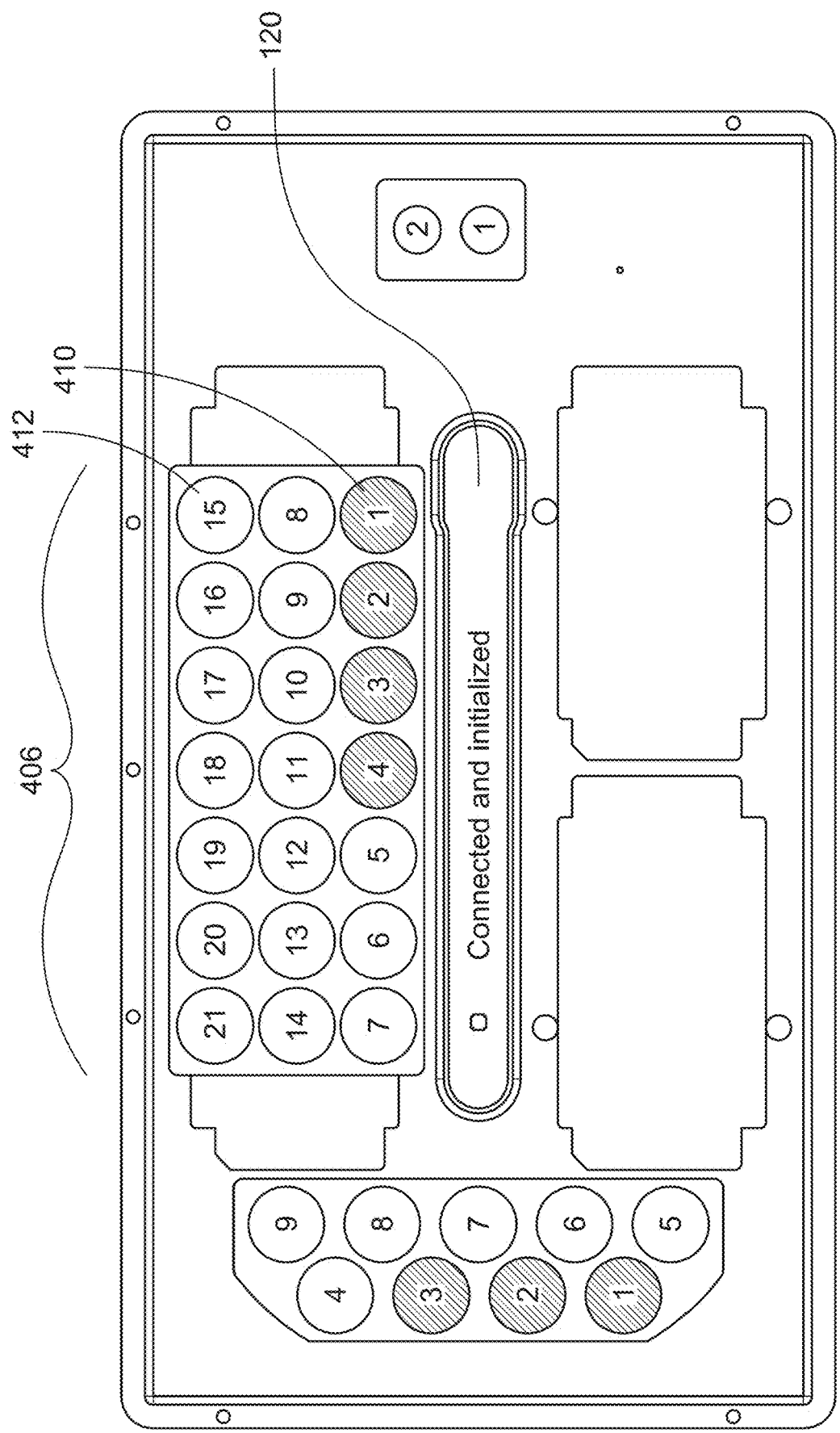
FIG. 29B is a diagrammatic top view showing the automated sampling or dispensing device detecting sample vessels positioned in slots, numbers one to four, adjacent to a center slot through which a z-axis support can pass.

In an implementation, as depicted in FIG. 29A, an automated sampling or dispensing device is shown with sample vessels 108 positioned in slots 406, numbers one to four, adjacent to a z-axis support 110. For instance, the sample rack is in the reverse or flipped orientation, where the samples vessels 108 are positioned in a reverse or flipped orientation as compared to the positioning in FIGS. 28A and 28B. By including one or more sample holder identifier 402, the automated sampling or dispensing device can detect the reverse or flipped orientation of the samples and maintain an accurate accounting for the samples and the analyses of the samples. For example, the communications interface can provide a graphical representation (e.g., as shown in FIG. 29B) of the presence of the sample vessels 108 in the slots, relative to the sample holder identifier 402 information, such that the sample vessels 108 are shown adjacent the center slot 120 in the proper order/configuration.

While sample holder identifiers 402 and sample identifiers 1002 have been described herein, it is noted that other aspects or components of the automated sampling or dispensing device can include labels configured for detection by identifier capture device 1004. For example, diluents, diluent holders, standards, standard holders, eluents, eluent holders, buffers, buffer holders, waste vessels, and the like can include identifiers (e.g., data matrix two-dimensional barcode) for tracking of the positioning of the respective items.

Figure 30A:
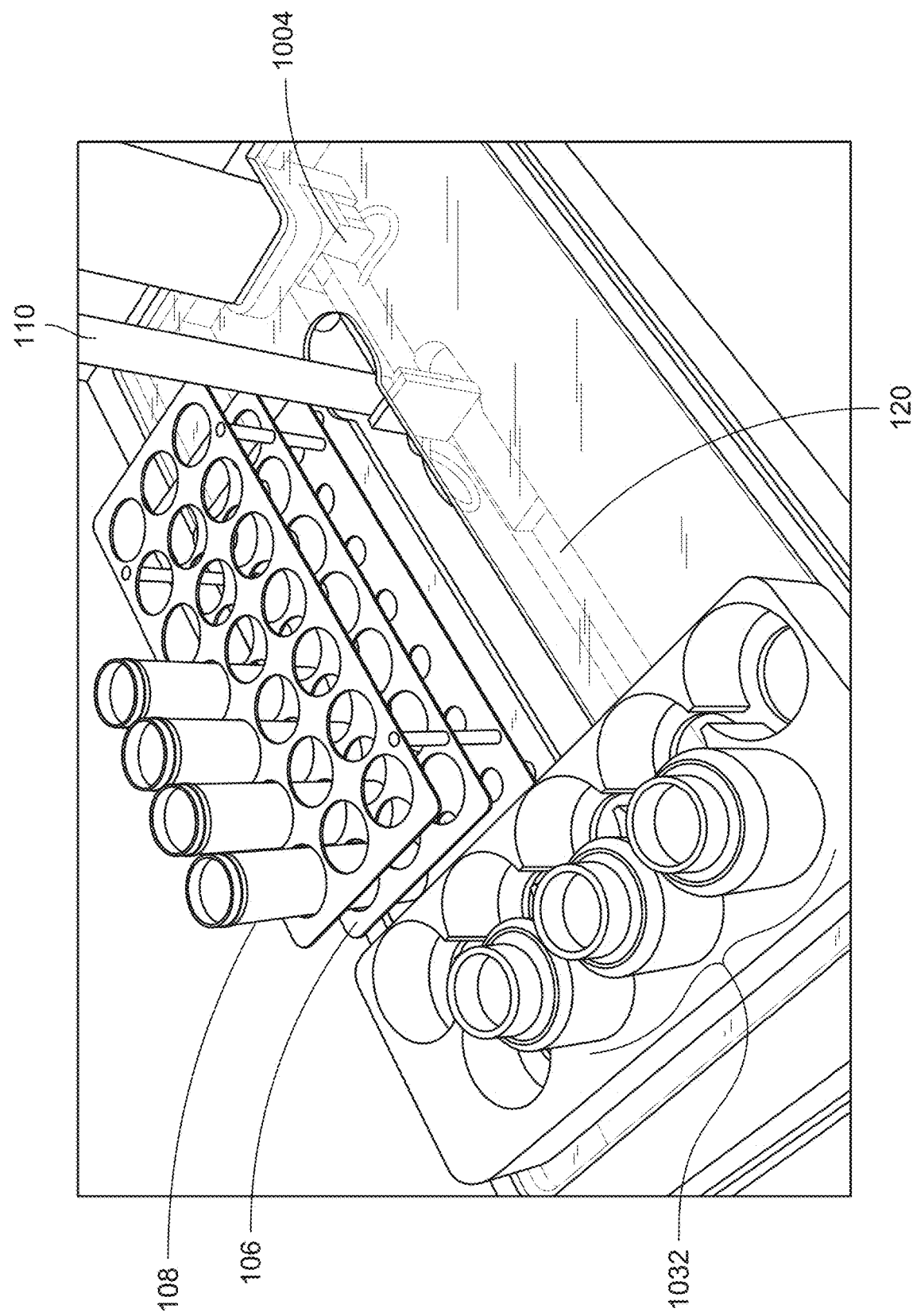
FIG. 30A is an isometric view of an automated sampling or dispensing device having a plurality of scientific standard solution vessels positioned in slots accessible by a probe of the automated sampling or dispensing device in accordance with an example implementation of the present disclosure.
Figure 30B:
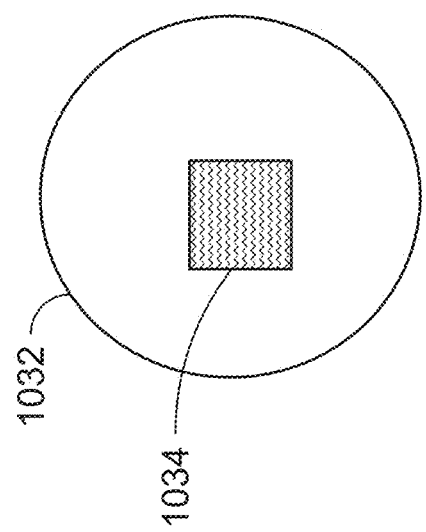
FIG. 30B is a diagrammatic bottom view of a scientific standard solution vessel having a standard identifier associated therewith in accordance with an example implementation of the present disclosure.

In an implementation, as shown in FIG. 30A, a plurality of scientific standard solution vessels 1032 are positioned relative to an automated sampling or dispensing device (e.g., sample identification system 1000), where the scientific standard solution vessels 1032 and any scientific standard solutions contained therein are accessible by a sample probe (e.g., sample probe 114). The scientific standard solution vessels 1032 each include one or more standard identifiers 1034 positioned on the scientific standard solution vessels 1032. For example, the standard identifiers can be positioned on a portion (e.g., bottom portion, top portion, side portion, etc.) of the scientific standard solution vessels 1032 for access by the identifier capture device 1004. FIG. 30B shows the standard identifier 1034 positioned on a bottom portion of a scientific standard solution vessel 1032. The standard identifier 1034 can include, but is not limited to, one or more of a barcode or a QR code. In an implementation, the standard identifier 1034 includes a data matrix two-dimensional barcode in a square matrix form (e.g., a 12×12 matrix, a 13×13 matrix, a 14×14 matrix, a 144×144 matrix etc.). While square matrices are provided as example data matrix barcodes, it is contemplated that rectangular matrices (e.g., a 8×18 matrix, a 16×48 matrix, etc.), or any other suitable matrix also may be utilized. The standard identifier 1034 can include other identification indicia including, but not limited to: characters and/or patterns configured for recognition by an optical camera or sensor; raised surfaces for recognition by touch sensors, optical sensors, and the like; illumination sources configured to generate a particular color (or wavelength), pattern of light, etc.; other identification indicia configured for recognition by the identifier capture device 1004; and so forth. The standard identifier 1034 is identifiable by an identifier capture device, such as the identifier capture device 1004 of the sample identification system 1000. The standard identifier 1034 can provide a unique identification of the scientific standard solution vessel 1032 and/or the scientific standard solution contained therein, where such unique identification can correspond to identification information including, but not limited to, standard identity, expiration status associated with the standard, analysis methods associated with the standard, matrices associated with the standard, elements/species associated with the standard, concentrations of the standard, and the like. Such corresponding identification information can be stored in a memory device accessible by one or more components of the automated sampling device or associated scientific instrumentation coupled thereto. In an implementation, the standard identifier 1034 is associated with an expiration status associated with a scientific standard solution located in the scientific standard solution vessel 1032 on which the standard identifier 1034 is positioned. The expiration status can include, but is not limited to, an expiration date, an indication that the scientific standard solution is expired, an indication that the scientific standard solution is about to expire (the current date is within a threshold time period (e.g., one day, one week, one month, etc.) of the expiration date), an initial preparation date, and so forth.

Figure 30C:
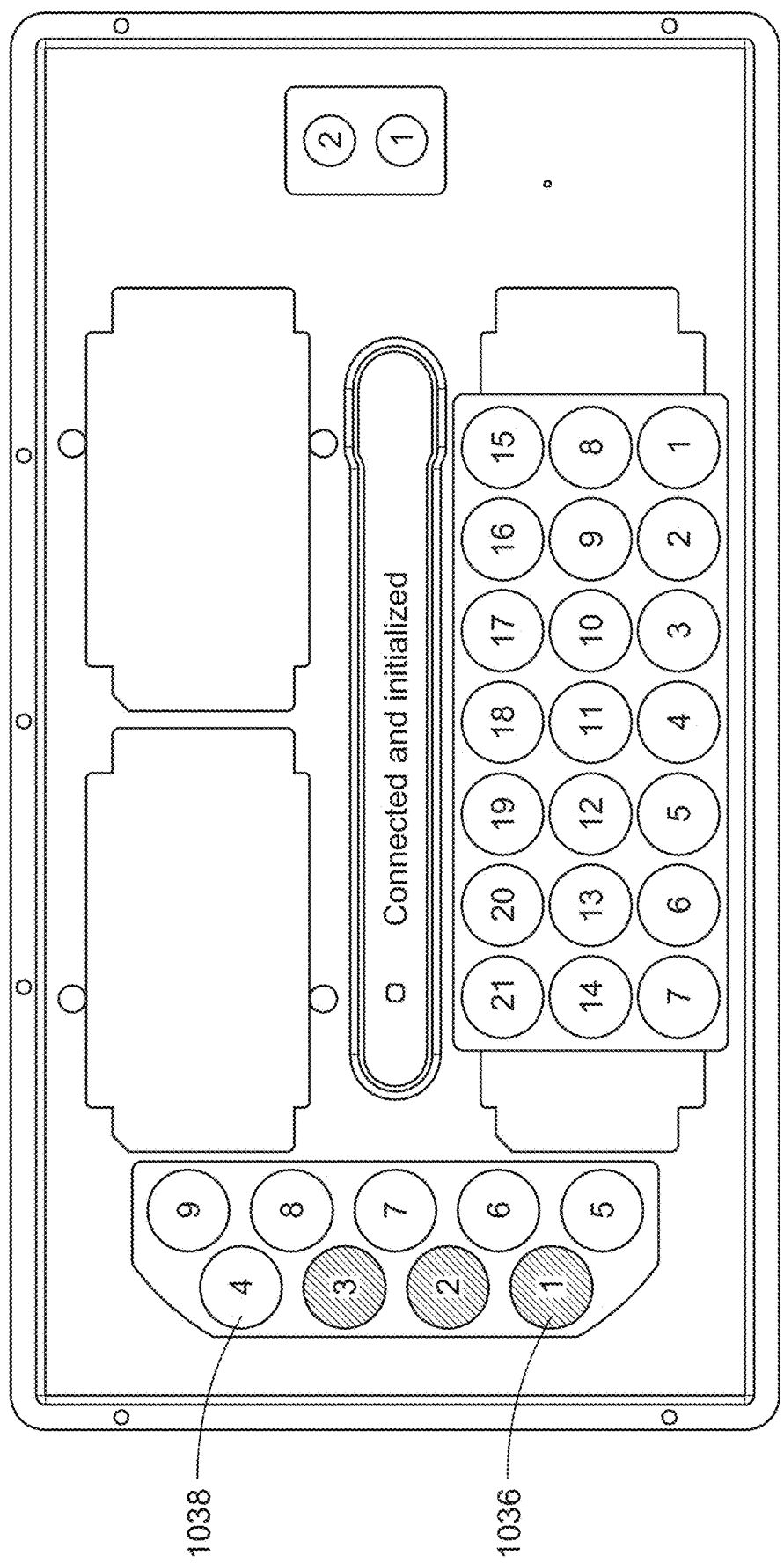
FIG. 30C is a diagrammatic top view showing the automated sampling or dispensing device detecting scientific standard solution vessels positioned in slots, numbers one to three, in accordance with an example implementation of the present disclosure.
Figure 30D:
FIG. 30D is a table showing information associated with scientific standard solutions, where a standard identifier associated with one of the scientific standard solutions corresponds to an expired scientific standard solution.

In an implementation, when the standard identifier 1034 is scanned and/or observed by the identifier capture device 1004, the identifier capture device 1004 can generate one or more data signals associated with the standard identifier 1034 that is associated with the expiration status of the scientific standard solution contained in the particular scientific standard solution vessel 1032. For example, the system 1000 can initiate a standard identifier protocol whereby the identifier capture device 1004 passes underneath the scientific standard solution vessels 1032 in a sequential manner (e.g., beginning at position 1 shown in FIG. 30C, continuing on to position 2, then continuing onto position 3, then continuing onto position 4, then, continuing onto position 5, etc.) to detect the presence (shown as 1036 in FIG. 30C) or absence (shown as 1038 in FIG. 30C) of a scientific standard solution vessel 1032 in a particular standard position. For instance, when the identifier capture device 1004 recognizes the standard identifiers 1034 associated with the scientific standard solution vessels 1032, the location of the scientific standard solution vessels 1032 can be shown via a communications interface, as depicted in FIG. 30C. Further, data associated with the scientific standard solutions contained in the scientific standard solution vessels 1032, provided by the standard identifiers 1034, can be displayed via the communications interface, such as shown in FIG. 30D (e.g., in tabular form). The communications interface can provide an expiration status of the individual scientific standard solutions, which can be displayed relative to the positions of the scientific standard solution vessels 1032. For example, FIG. 30D includes an expiration date or an expiration status 1040 of each of the three scientific standard solutions identified by the identifier capture device 1004, where the communications interface provides an indication that the scientific standard solution associated with position or vial 3 has expired (e.g., such as by comparing an expiry date with a current date). In an implementation, the system 1000 can provide an alert (e.g., via a display device) based upon detection of an expired scientific standard solution present in a scientific standard solution vessels 1032 via the standard identifier 1034 (e.g., the expiration status is indicative of an expired scientific standard solution). The system 1000 can automatically stop operation of the sample probe 114 upon detection of the expired scientific standard solution to prevent addition of the expired scientific standard solution to any of the sample vessels 108. The system 1000 can receive user input to delay operation, such as to permit placement of a new scientific standard solution vessel 1032 in the position occupied by the expired scientific standard solution. When user input is received to delay operation, the system 1000 may scan the standard identifiers 1034 of any scientific standard solution vessels 1032 present upon resuming operation, such as to determine whether the user changed the order of scientific standard solution vessels 1032, change the number of scientific standard solution vessels 1032, introduced new scientific standard solution vessel(s) 1032 having new standard identifier(s) 1034, or the like.

Figure 31:
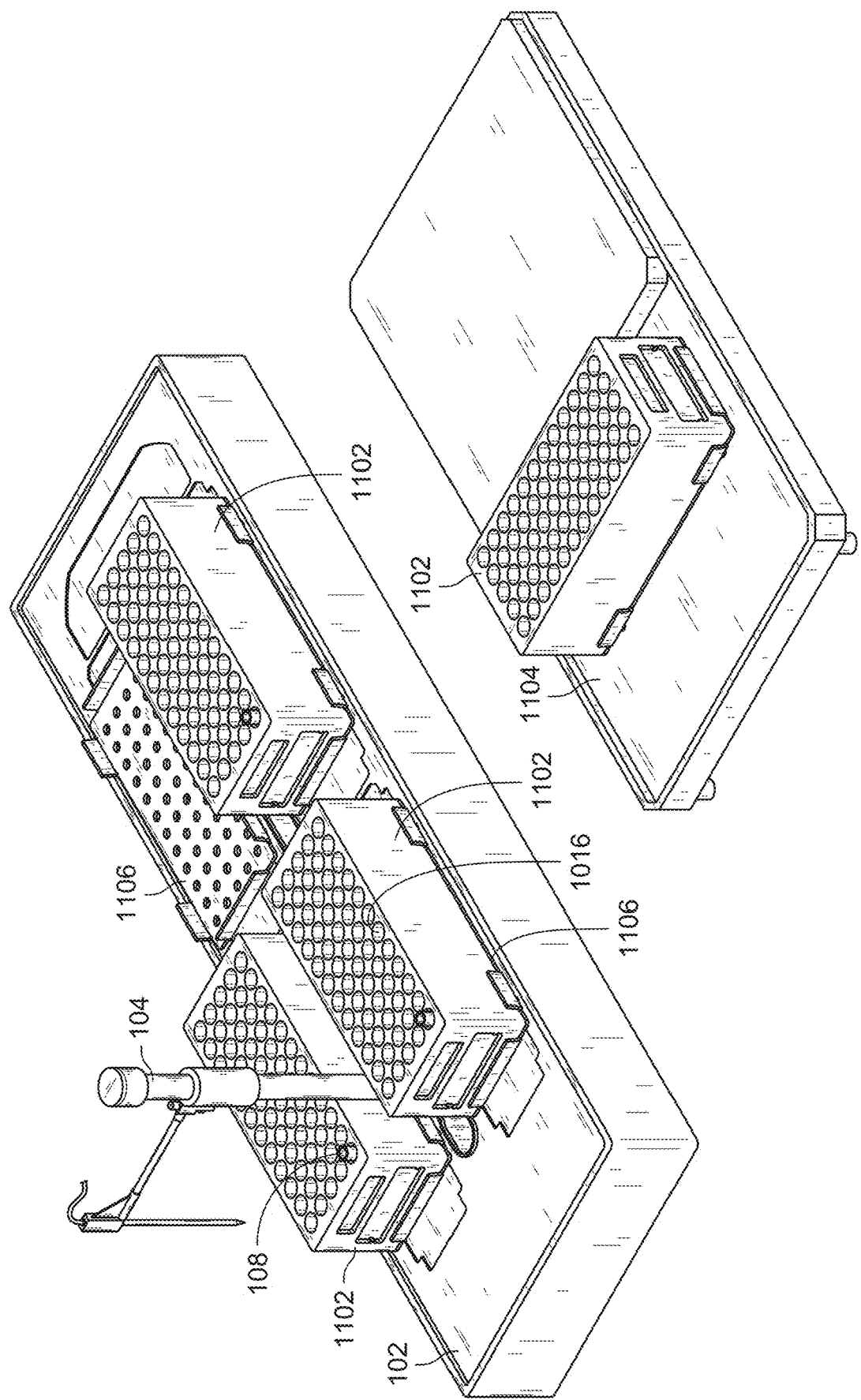
FIG. 31 is an isometric view of an automated sampling or dispensing device including an enclosed sample holder and a heating element in accordance with example implementations of the present disclosure.
Figure 32:
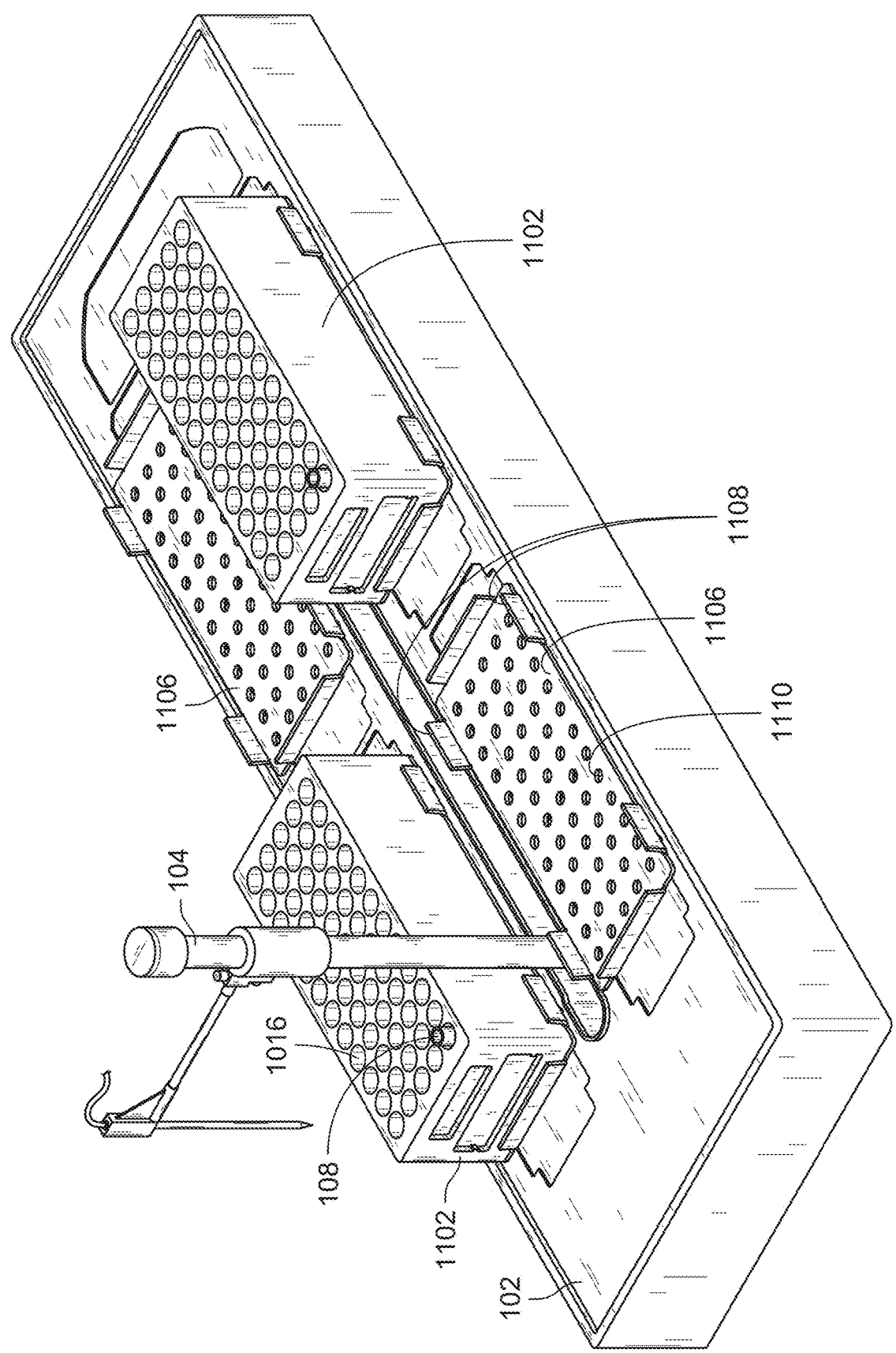
FIG. 32 is an isometric view of an automated sampling or dispensing device including an enclosed sample holder and a sampling base in accordance with example implementations of the present disclosure.
Figure 33:
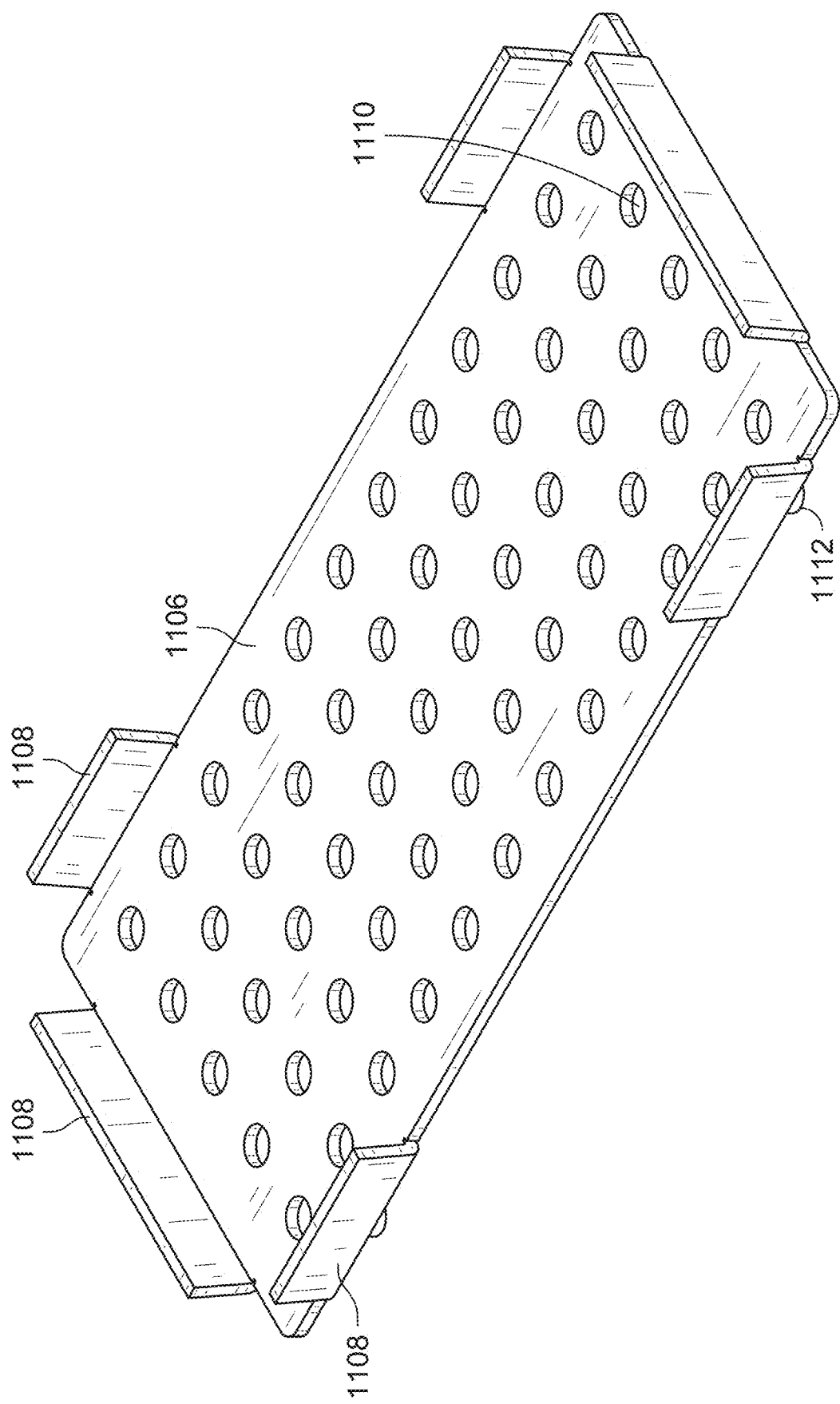
FIG. 33 is an isometric view of a sampling base of an enclosed sample holder, where the sampling base includes one or more protrusions for mating with a support surface.

In an implementation, as depicted in FIGS. 31 through 34, the autosampler/dispensing device includes an enclosed sample holder 1102. For example, the enclosed sample holder 1102 can have solid side portions, forming a block. The enclosed sample holder 1102 may be constructed from a heat resistive and/or heat retentive material including, but not necessarily limited to: aluminum, tungsten, nickel, titanium, graphite, heat resistant plastic, and so forth. The enclosed sample holder 1102 can be configured to heat the samples by dispersing heat throughout the sample vessels 108. For example, the enclosed sample holder 1102 can be removably coupled to a heating element 1104 (such as shown in FIG. 31). In some implementations, the heating element 1104 comprises a relatively flat platform configured to receive the enclosed sample holder 1102 (e.g. a bottom portion of the enclosed sample holder 1102 rests on the platform). However other types of heating elements may be utilized. Heating the samples vessels 108 can reduce the viscosity of the samples (e.g., to improve the accuracy of the automated sampling or dispensing device, to facilitate transfer of a viscous sample through an analytical instrument and/or sample preparation system, or so forth). Alternatively, the enclosed sample holder 1102 can be utilized to reduce exposure of high sensitivity samples (e.g., light-sensitive samples). In some implementations, the enclosed sample holder 1102 defines a first set of apertures 1016, through which the sample vessels 108 may pass, and a second set of apertures 1018 which prohibit at least a portion of the sample vessels 108 from completely passing through, as described above. In an implementation (such as shown in FIGS. 31 through 33), the enclosed sample holder 1102 includes a sampling base 1106. The sampling base 1106 can be removably coupled to the enclosed sample holder 1102 so that the bottom portion of the enclosed sample holder 1102 sits within the sampling base 1106. For example, the sampling base can include one or more rim portions 1108 configured to retain the enclosed sample holder 1102. In some implementations, the sampling base 1106 can include a third set of apertures 1110 that correspond to the second set of apertures 1018 (e.g., the diameter of the third set of apertures 1110 is approximately equal to the diameter of the second set of apertures 1018). Such a configuration of apertures may provide an exposed bottom portion of the sample vessel 108 such that a sample identifier 1002 positioned on the base of the sample vessel 108 is unobstructed with respect to an identifier capture device 1004. Alternatively, a bottom portion of the enclosed sample holder 1102 and/or the sampling base 1106 may be constructed from a substantially clear, light transmissive, or transparent material to expose the bottom portion of the sample vessels 108. It is contemplated that the size, shape, and materials comprising the enclosed sample holder 1102 and/or the sampling base 1106 may vary depending on the type, size, and shape of the identifier capture device 1004 used in the automated sampling/dispensing device, and the type of samples to be analyzed (e.g., corrosive, inert, and so forth).

Figure 34:
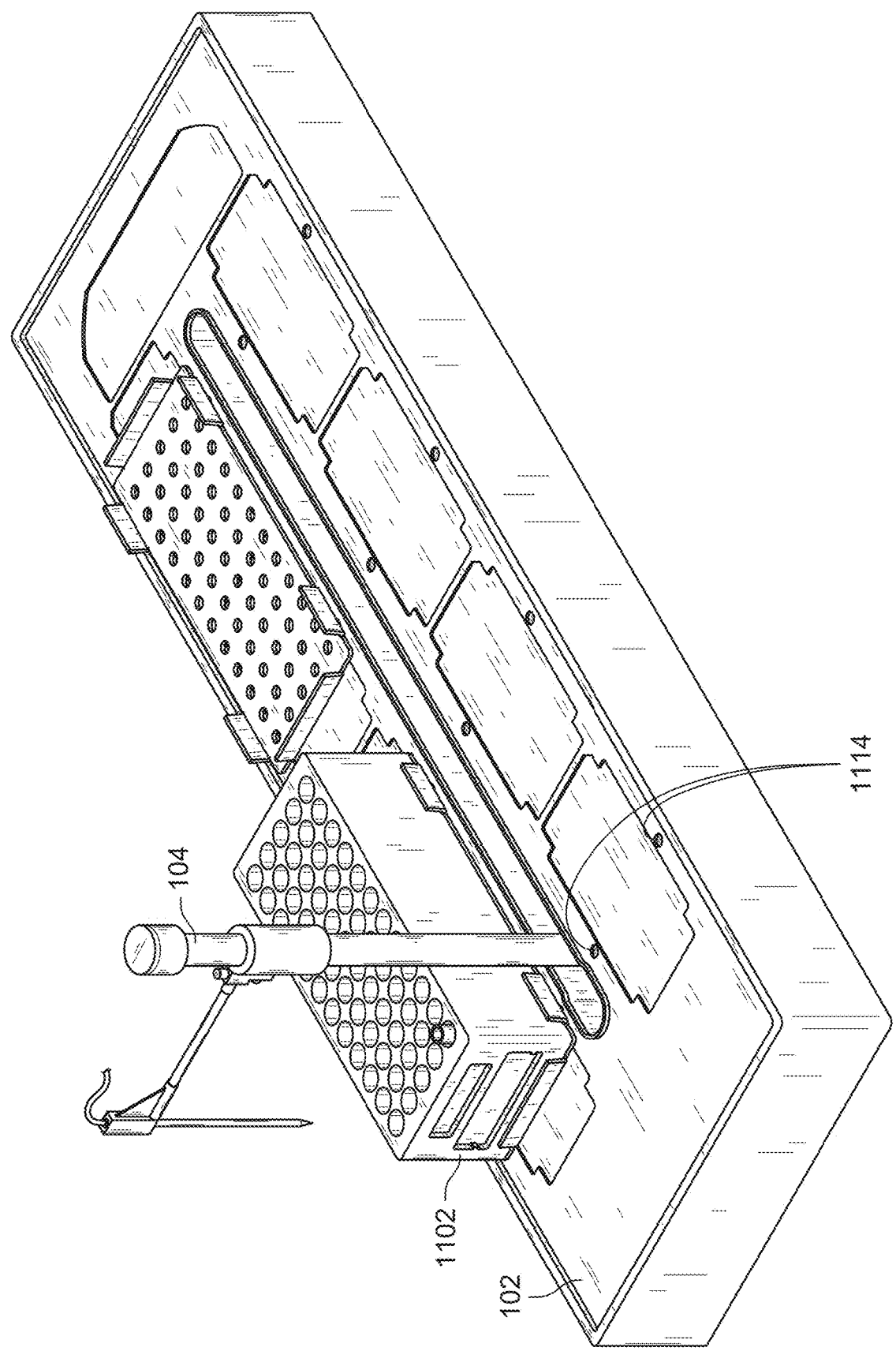
FIG. 34 is an isometric view illustrating a support surface for use with an automated sampling or dispensing device, where the support surface includes recesses for mating with a sampling base in accordance with example implementations of the present disclosure

In example implementations, the support surface (e.g., table top 102) of the automated sampling/dispensing device can be configured to mate with the sample holder 1102 (such as shown in FIGS. 33 and 34). For example, the sampling base 1106 can include one or more protrusions 1112 (e.g., feet). The table top 102 can be keyed with corresponding recesses 1114 configured to mate with the protrusions 1112. Alternatively, the protrusions 1112 can be located on the bottom portion of the enclosed sample holder 1102. By configuring the table top 102 to mate with the sampling base 1106 and/or the enclosed sample holder 1102, the sampling base 1106 and/or sample holder 1102 is properly oriented for detection by the sample arm assembly 104 and/or the identifier capture device 1004). For example, the front portion or top portion of the sample holder 1102 is directionally oriented with respect to the sample arm assembly 104 and/or the identifier capture device 1004.

In some implementations, the enclosed sample holder 1102 can include a sample holder identifier 402 configured to provide dynamic data associated with the enclosed sample holder 1102 including, but not limited to, a unique rack identification (ID), a position of the enclosed sample holder 1102, an orientation of the enclosed sample holder 1102 (e.g., a standard orientation, a reverse or flipped orientation, etc.), an alignment of the enclosed sample holder 1102, and the like, as described above. In some implementations, the sample holder identifier 402 can be located on the sampling base 1106. Alternatively, the sample holder identifier 402 can be located on a top portion, a bottom portion, a side portion, a support post portion, or the like, of the enclosed sample holder 1102, such that the identifier capture device 1004 can recognize the sample holder identifier 402. For example, the sampling base 1106 can include an aperture configured to expose a sample holder identifier 402 located on a bottom portion of the enclosed sample holder 1102. In some implementations, the enclosed sample holder 1102 can be directionally keyed to fit within the sampling base 1106 in a particular orientation. By keying the enclosed sample holder 1102, the automated sampling or dispensing device can detect the orientation of the enclosed sample holder 1102 and/or the proper order/configuration of sample vessels 108 from sample holder identifiers 402 located on the sampling base 1106. For example, a sample holder identifier 402a including identification information that corresponds to a front orientation of the enclosed sample holder 1102 will correspond to the orientation of both the enclosed sample holder 1102 and the sampling base 1106.

In some implementations, the identifier capture device 1004 can be positioned beneath the table top 102, as described above. For example, the autosampler can include a raised surface 1008 configured to be supported by the autosampler table top 102 (such as shown in FIGS. 21A through 21C). For instance, in implementations, the raised surface 1008 defines gaps 1012 in the surface over which the enclosed sample holders 1102 and/or sample vessels 108 having sample holder identifiers 402 and sample identifiers 1002, respectively, positioned on a bottom surface are situated. In this manner, the sample holder identifiers 402 and/or sample identifiers 1002 at the base or bottom of the sample vessels 108 are accessible to the identifier capture device 1004 when positioned beneath the raised surface 1008 in the gap 1010 (such as shown in FIG. 22). Alternatively, the table top 102, or a portion thereof, may be constructed from a substantially clear, light transmissive, or transparent material to expose the bottom portion of the sample vessels 108 and/or a bottom portion of the enclosed sample holder 102. In other implementations, the identifier capture device 1004 can be positioned above the table top 102 (e.g., mounted to the sample arm assembly 104). Alternatively, the enclosed sample holders 1102 can be detected by sensors coupled to the table top 102.

Although particular embodiments of this invention have been illustrated, it is apparent that various modifications and embodiments of the invention may be made by those skilled in the art without departing from the scope and spirit of the foregoing disclosure. Accordingly, the scope of the invention should be limited only by the claims appended hereto.

While the subject matter has been described in language specific to structural features and/or process operations, it is to be understood that the subject matter defined in the appended claims is not necessarily limited to the specific features or acts described above. Rather, the specific features and acts described above are disclosed as example forms of implementing the claims.

What is claimed is:

1. A sample identification system for an automated sampling or dispensing device, comprising:
a sample holder having a plurality of apertures configured to receive a plurality of sample vessels therein, the sample holder having one or more corresponding sample holder identifiers positioned proximate to the sample holder;
a surface structure supporting at least a portion of the sample holder, the surface structure defining a slot extending a length across the surface structure;
a sample arm assembly including a support extending through the slot, the support coupled with a drive assembly configured to provide translation of the support along the length of the slot, the sample arm assembly further including a sample probe coupled to the support with at least a portion of the sample holder positioned between the sample probe and the surface structure, the sample probe configured to couple with a tube to receive a fluid from a sample vessel of the plurality of sample vessels through the sample probe and into the tube; and
an identifier capture device coupled to the support of the sample arm assembly with the surface structure positioned between the sample holder and the identifier capture device and with the surface structure positioned between the sample probe and the identifier capture device, the identifier capture device configured to detect the one or more sample holder identifiers positioned proximate to the sample holder and generate a data signal in response thereto, the data signal corresponding to at least an orientation of the sample holder relative to the surface structure on which the sample holder is positioned.

2. The sample identification system as recited in claim 1, wherein the one or more sample holder identifiers include at least one of a barcode or a QR code.

3. The sample identification system as recited in claim 1, wherein the one or more sample holder identifiers include at least two sample holder identifiers, each of which correspond to a different orientation of the sample holder.

4. The sample identification system as recited in claim 3, wherein the at least two sample holder identifiers include a first sample holder identifier corresponding to a standard orientation of the sample holder and a second sample holder identifier corresponding to a reverse orientation of the sample holder.

5. The sample identification system as recited in claim 4, wherein the sample holder includes a distinct label for each of the plurality of apertures, wherein the first sample holder identifier is positioned on an opposite side of the sample holder as compared to an aperture of the plurality of apertures having a first designation in a series as the distinct label.

6. The sample identification system as recited in claim 4, wherein the sample holder includes a distinct label for each of the plurality of apertures, wherein the first sample holder identifier is positioned on a same side of the sample holder as compared to an aperture of the plurality of apertures having a first designation in a series as the distinct label.

7. The sample identification system as recited in claim 1, wherein the sample holder includes at least one sample holder identifier positioned on a bottom surface of the sample holder, the bottom surface being opposite of a surface in which the plurality of sample vessels is received into the plurality of apertures.

8. The sample identification system as recited in claim 1, wherein the sample holder includes a distinct label for each of the plurality of apertures.

9. The sample identification system as recited in claim 1, wherein the data signal further corresponds to information regarding position of a sample vessel relative to an aperture of the plurality of apertures.

10. The sample identification system as recited in claim 1, wherein the sample holder comprises an enclosed sample holder.

11. The sample identification system as recited in claim 10, further including a heating element removably coupled to the enclosed sample holder, the heating element configured to disperse heat to the enclosed sample holder.

12. The sample identification system as recited in claim 11, wherein the enclosed sample holder includes a removable sampling base configured to removably mate with the surface.

13. The sample identification system as recited in claim 12, wherein the removable sampling base includes one or more corresponding sample holder identifiers positioned on a portion of the sampling base.

14. The sample identification system as recited in claim 1, wherein the surface structure includes a light transmissive material through which the identifier capture device detects the one or more sample holder identifiers.

* * * * *